(12) United States Patent
Yang et al.

(10) Patent No.: US 10,912,737 B2
(45) Date of Patent: Feb. 9, 2021

(54) NANO COMPLEX COMPRISING A NANO DRUG DELIVERY MATRIX; AND A GINSENG EXTRACT OR A GINSENOSIDE ISOLATED THEREFROM

(71) Applicant: University-Industry Cooperation Group of Kyung Hee University, Gyeonggi-do (KR)

(72) Inventors: Deok Chun Yang, Gyeonggi-do (KR); Yeon-Ju Kim, Gyeonggi-do (KR); Singh Priyanka, Gyeonggi-do (KR); Dong Uk Yang, Gyeonggi-do (KR); Sung Eun Ahn, Gyeonggi-do (KR); Mathiyalagan Ramya, Gyeonggi-do (KR)

(73) Assignee: UNIVERSITY-INDUSTRY COOPERATION GROUP OF KYUNG HEE UNIVERSITY, Gyeonggi-Do (KR)

( * ) Notice: Subject to any disclaimer, the term of this patent is extended or adjusted under 35 U.S.C. 154(b) by 216 days.

(21) Appl. No.: 16/070,305

(22) PCT Filed: Jan. 13, 2017

(86) PCT No.: PCT/KR2017/000489
§ 371 (c)(1),
(2) Date: Dec. 16, 2018

(87) PCT Pub. No.: WO2017/123056
PCT Pub. Date: Jul. 20, 2017

(65) Prior Publication Data
US 2019/0125690 A1 May 2, 2019

(30) Foreign Application Priority Data

Jan. 14, 2016 (KR) .................... 10-2016-0004875
Apr. 8, 2016 (KR) .................... 10-2016-0043664
Apr. 8, 2016 (KR) .................... 10-2016-0043668

(51) Int. Cl.
*A61K 36/258* (2006.01)
*A61K 36/24* (2006.01)
(Continued)

(52) U.S. Cl.
CPC .......... *A61K 9/5115* (2013.01); *A23L 33/105* (2016.08); *A61K 9/5192* (2013.01);
(Continued)

(58) Field of Classification Search
CPC ............................. A61K 36/258; A61K 33/24
See application file for complete search history.

(56) References Cited

FOREIGN PATENT DOCUMENTS

| CN | 103768024 | 5/2014 |
|---|---|---|
| KR | 10-2011-0113228 | 6/2012 |

(Continued)

OTHER PUBLICATIONS

English machine translation of Gwangju Institute of Science and Technology, KR 1014239350000 B, 2014. (Year: 2014).*

(Continued)

*Primary Examiner* — Rosanne Kosson
(74) *Attorney, Agent, or Firm* — Parker Highlander PLLC

(57) ABSTRACT

Provided are a nanocomposite including a nano-drug delivery system; and a ginseng extract or a ginsenoside isolated therefrom, and a preparation method thereof, in which the nanocomposite may be used for the prevention or treatment of cancer and inflammatory diseases.

The metal nanocomposite of the present invention may be prepared in a uniform size without using an additional reducing agent or stabilizing agent in a significantly shortened time, as compared with known metal nanoparticles. Further, since the metal nanocomposite has high solubility in water and high targeting ability for cancer cells, it can be (Continued)

advantageously developed as drugs. Further, the metal nanocomposite exhibits high anti-cancer and anti-inflammatory activities, and thus may be usefully applied to prevention or treatment of cancer and inflammatory diseases. Furthermore, the metal nanocomposite exhibits anti-microbial activity, biofilm-degrading activity, and anti-coagulant activity, and thus may be applied to a variety of industrial fields.

1 Claim, 31 Drawing Sheets

(51) Int. Cl.
    *A61K 9/51*     (2006.01)
    *A23L 33/105*     (2016.01)
    *A61K 31/704*     (2006.01)
    *A61K 47/69*     (2017.01)
    *A61K 47/64*     (2017.01)
    *A61P 29/00*     (2006.01)
    *A61P 35/00*     (2006.01)
    *A61K 36/25*     (2006.01)
    *B82Y 5/00*     (2011.01)

(52) U.S. Cl.
    CPC ............ *A61K 31/704* (2013.01); *A61K 36/25* (2013.01); *A61K 36/258* (2013.01); *A61K 47/643* (2017.08); *A61K 47/6923* (2017.08); *A61K 47/6929* (2017.08); *A61P 29/00* (2018.01); *A61P 35/00* (2018.01); *A23V 2002/00* (2013.01); *B82Y 5/00* (2013.01)

(56) References Cited

FOREIGN PATENT DOCUMENTS

| KR | 10-2014-0043954 | 7/2014 |
|---|---|---|
| KR | 10-2015-0125785 | 3/2016 |
| KR | 10-2016-0029894 | 6/2016 |
| KR | 10-2016-0018974 | 4/2017 |
| KR | 10-2016-0018147 | 8/2017 |

OTHER PUBLICATIONS

Choi, Kyungsun, et al. "Ginsenosides compound K and Rh2 inhibit tumor necrosis factor-α-induced activation of the NF-κB and JNK pathways in human astroglial cells." *Neuroscience letters* 421.1 (2007): 37-41.
Ahmad, Tokeer, et al. "Biosynthesis, structural characterization and antimicrobial activity of gold and silver nanoparticles." *Colloids and Surfaces B: Biointerfaces* 107 (2013): 227-234.
Choo, Min-Kyung, et al. "Antiallergic activity of ginseng and its ginsenosides." *Planta medica* 69.06 (2003): 518-522.
Ganesan, Palanivel, et al. "Recent trends of nano bioactive compounds from ginseng for its possible preventive role in chronic disease models." *RSC Advances* 5.119 (2015): 98634-98642.
Guo, Xiao-Xi, et al. "Giseonside rh2 induces human hepatoma cell apoptosisvia bax/bak triggered cytochrome C release and caspase-9/caspase-8 activation." *International journal of molecular sciences* 13.12 (2012): 15523-15535.
He, Long, et al. "Ginsenoside Rh2 inhibits osteoclastogenesis through down-regulation of NF-κB, NFATc1 and c-Fos." *Bone*50.6 (2012): 1207-1213.
Law, Carmen Ka-Man, et al. "Ginsenoside compound K induces apoptosis in nasopharyngeal carcinoma cells via activation of apoptosis-inducing factor." *Chinese medicine* 9.1 (2014): 11.
Lee, Jae-Young, et al. "Nanocomplexes Based on Amphiphilic Hyaluronic Acid Derivative and Polyethylene Glycol-Lipid for Ginsenoside Rg3 Delivery." *Journal of pharmaceutical sciences* 103.10 (2014): 3254-3262.
Shin, Yong-Wook, and Dong-Hyun Kim. "Antipruritic effect of ginsenoside rb1 and compound k in scratching behavior mouse models." *Journal of pharmacological sciences* 99.1 (2005): 83-88.
Singh, Priyanka, et al. "Biogenic silver and gold nanoparticles synthesized using red ginseng root extract, and their applications." *Artificial cells, nanomedicine, and biotechnology*44.3 (2016): 811-816.
Singh, Priyanka, et al. "The development of a green approach for the biosynthesis of silver and gold nanoparticles by using Panax ginseng root extract, and their biological applications." *Artificial cells, nanomedicine, and biotechnology* 44.4 (2016): 1150-1157.
Singh, Priyanka, Yeon Ju Kim, and Deok Chun Yang. "A strategic approach for rapid synthesis of gold and silver nanoparticles by Panax ginseng leaves." *Artificial cells, nanomedicine, and biotechnology* 44.8 (2016): 1949-1957.
Tang, Xi-Ping, et al. "Effects of ginsenoside Rh2 on growth and migration of pancreatic cancer cells." *World Journal of Gastroenterology: WJG* 19.10 (2013): 1582.
Tohda, Chihiro, et al. "Aβ (25-35)-induced memory impairment, axonal atrophy, and synaptic loss are ameliorated by M1, A metabolite of protopanaxadiol-type saponins." *Neuropsychopharmacology* 29.5 (2004): 860.
Vogler, Erwin A., and Chlistopher A. Siedlecki. "Contact activation of blood-plasma coagulation." *Biomaterials* 30.10 (2009): 1857-1869.
Xu, Yi, et al. "Effect of amino groups of mesoporous silica nanoparticles on CpG oligodexynucleotide delivery." *Science and technology of advanced materials* 16.4 (2015): 045006.
Yang, Rui, et al. "20 (s)-ginsenoside Rg3 -loaded magnetic human serum albumin nanospheres applied to HeLa cervical cancer cells in vitro." *Bio-medical materials and engineering*24.6 (2014): 1991-1998.
Yu, Zhan, et al. "Bovine serum albumin nanopartieles as controlled release carrier for local drug delivery to the inner ear." *Nanoscale research letters* 9.1 (2014): 343.
Zhao et al., "Development of mesoporous silica nanoparticle for enhancing the dissolution of ginsenoside Rg3", *Chinese Traditional Patent Medicine*, Sep. 2014. English Abstract.
Zhao, Lei, et al. "Bovine serum albumin nanoparticles for delivery of tacrolimus to reduce its kidney uptake and functional nepgrotoxicity." *International journal of pharmaceutics* 483.1-2 (2015): 180-187.

* cited by examiner

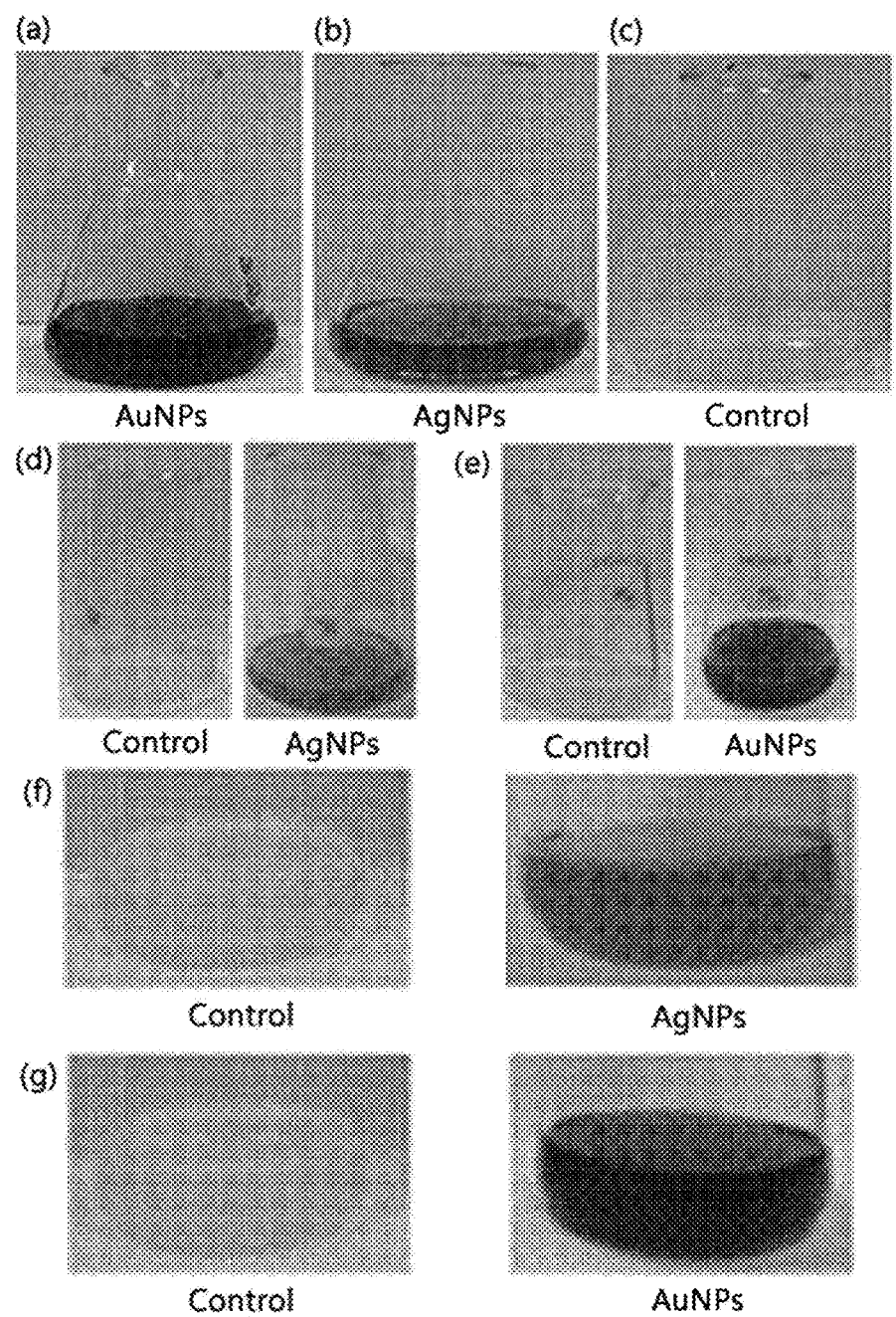
[FIGS. 1A-G]

[FIGS. 2A-B]
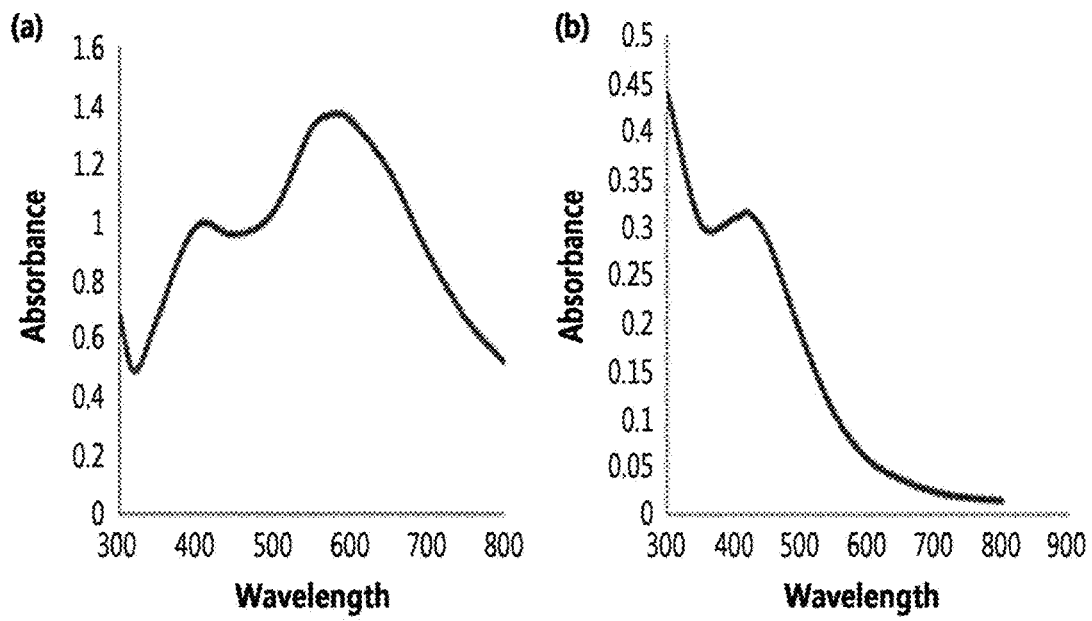
[FIGS. 3A-B]
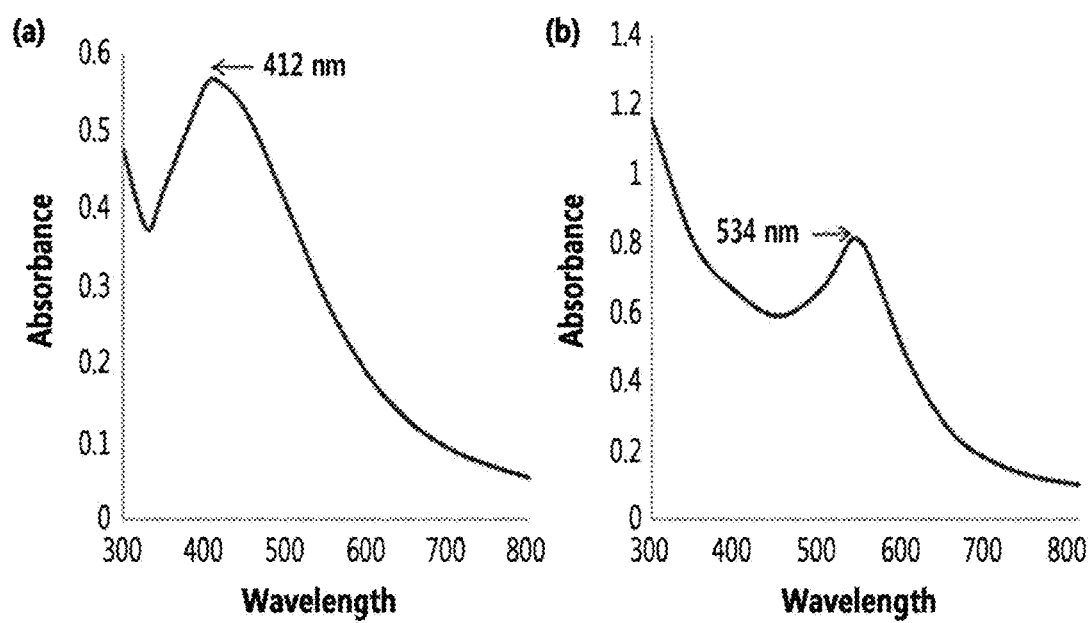

[FIGS. 4A-B]
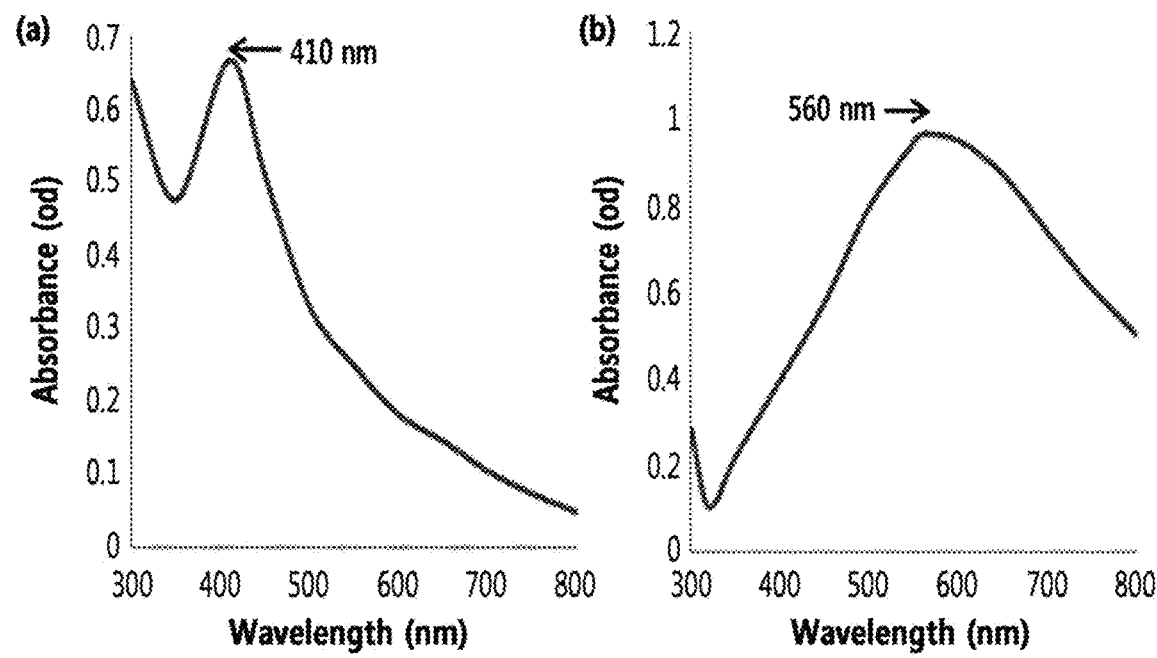

[FIGS. 5A-H]
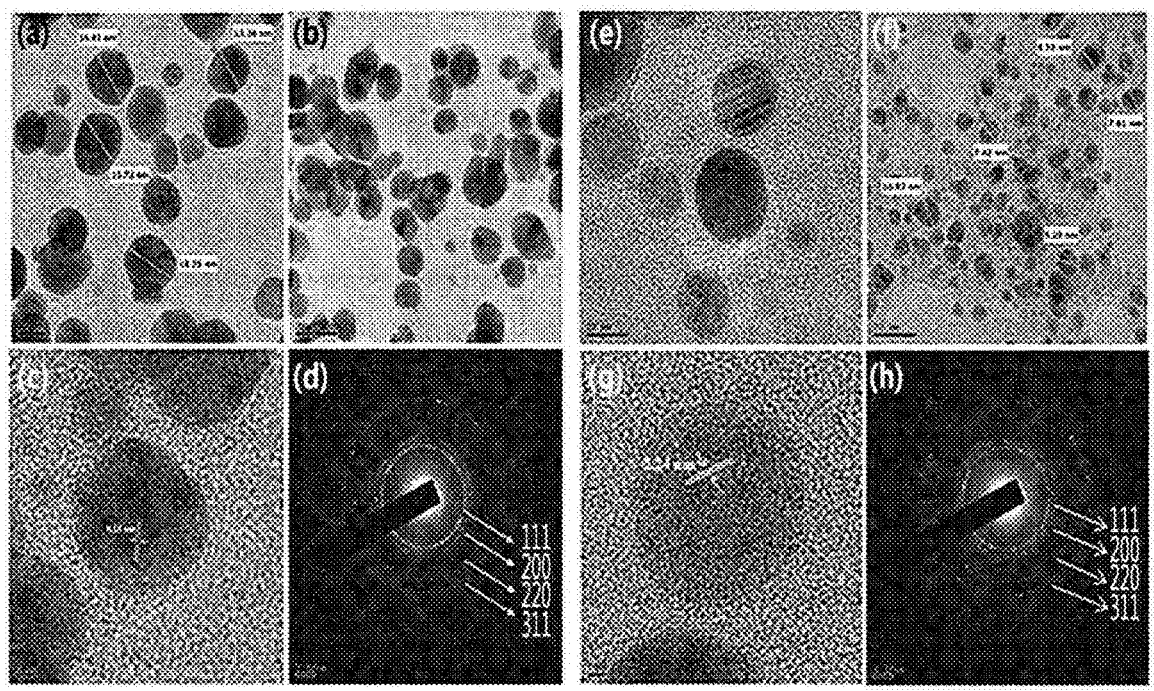

[FIGS. 6A-D]
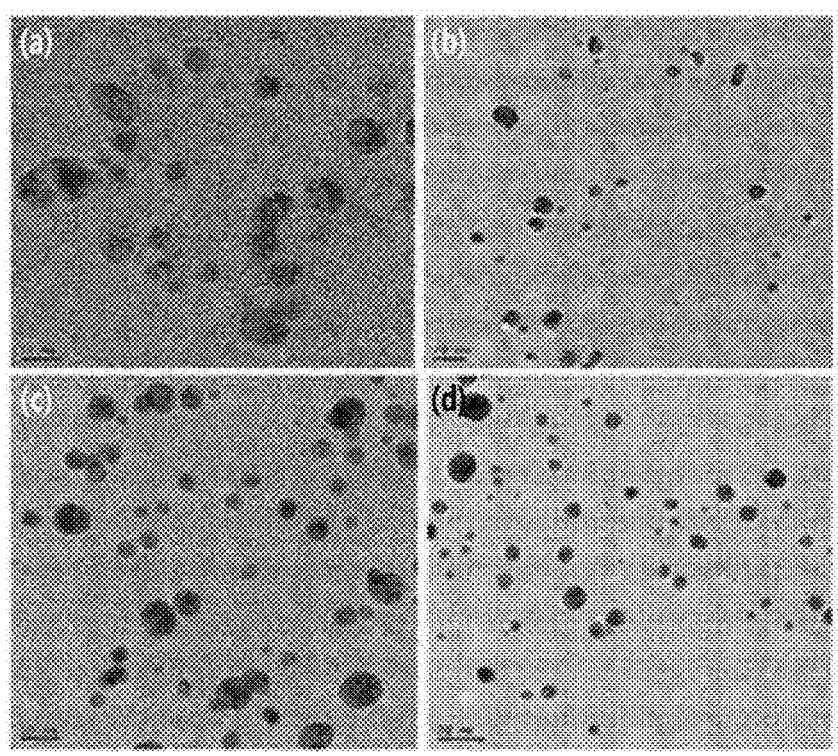

[FIGS. 7A-F]
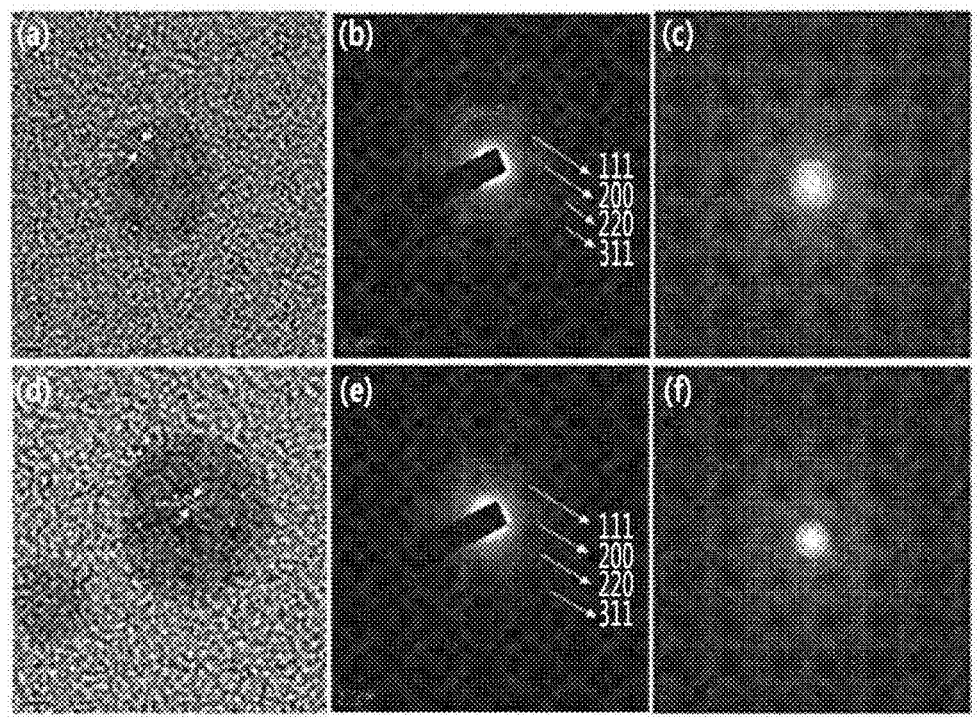
[FIGS. 8A-B]
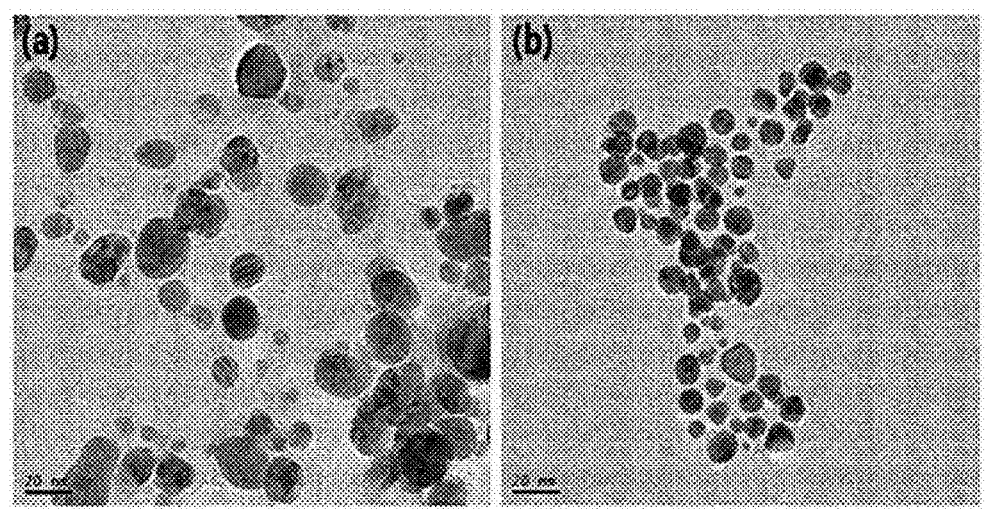

[FIGS. 9A-B]
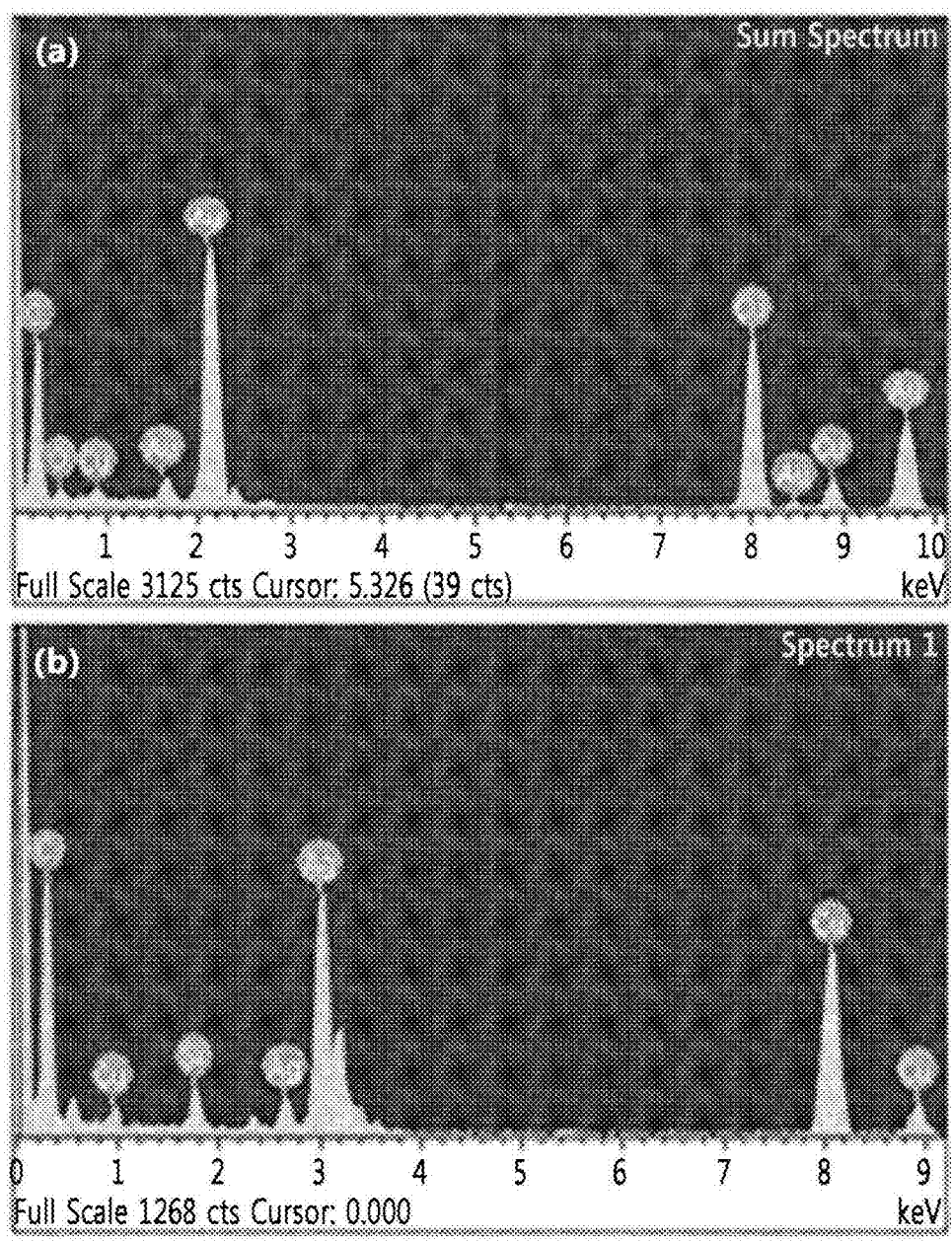

[FIGS. 10A-B]
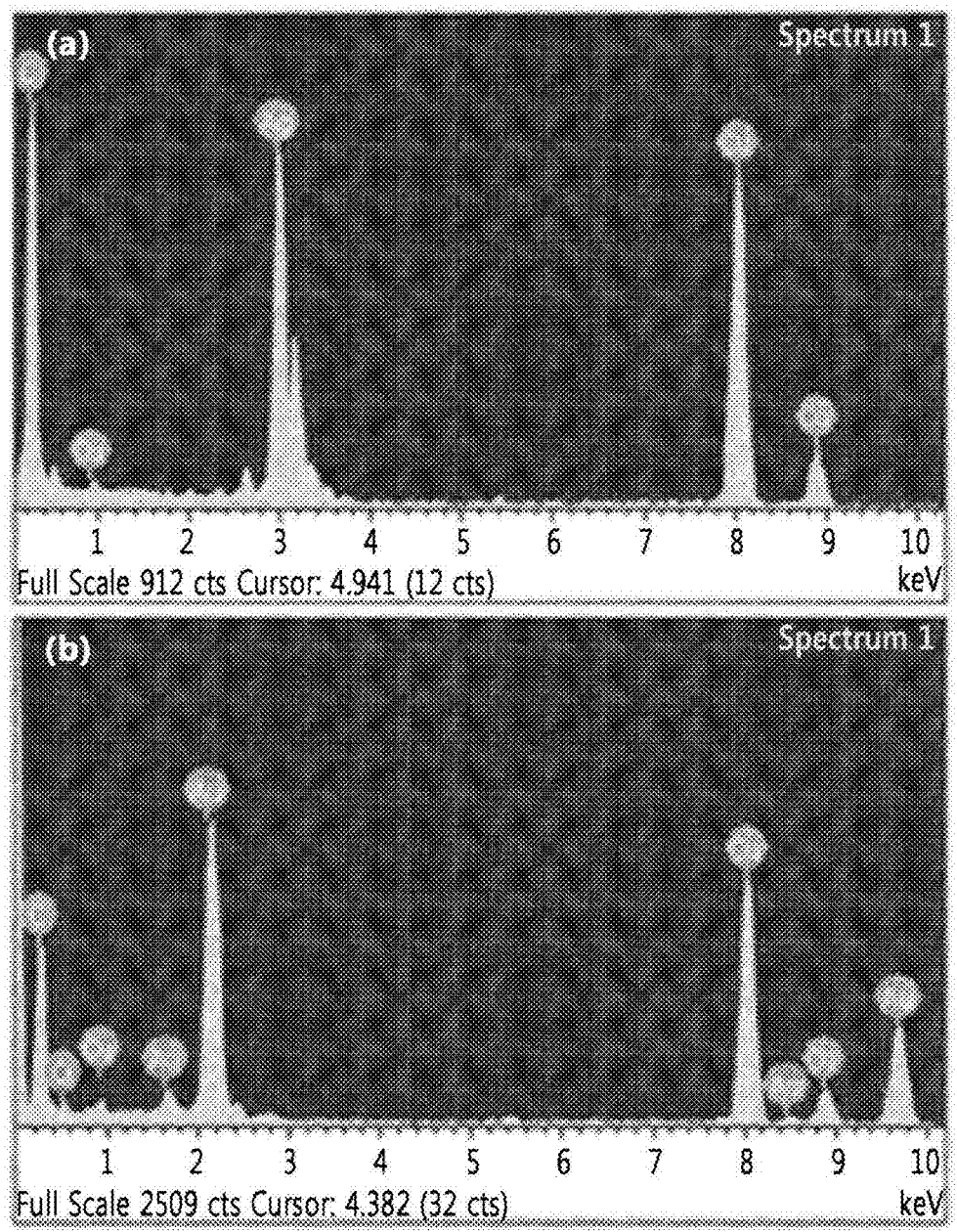

[FIGS. 11A-B]
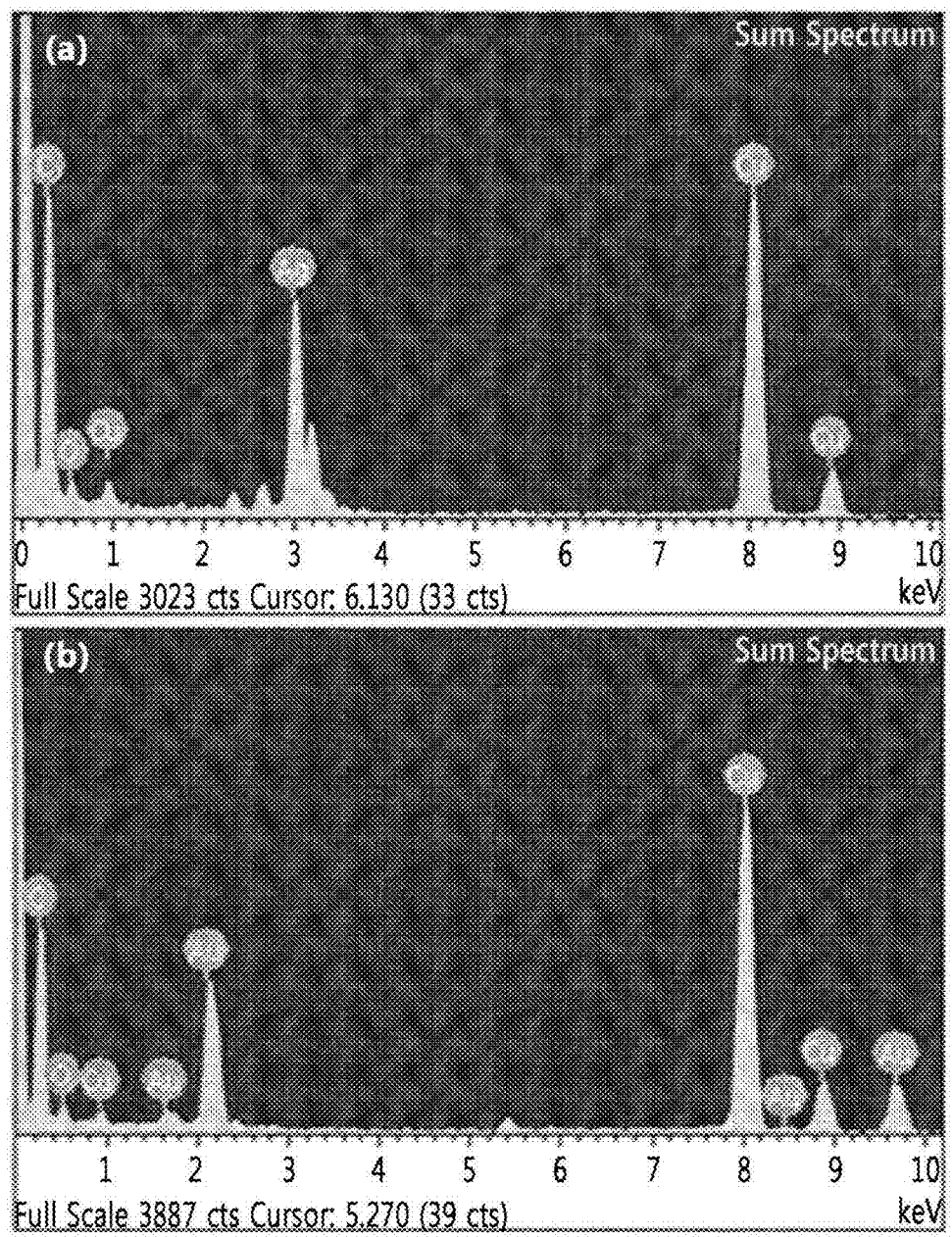

[FIGS. 12A-D]
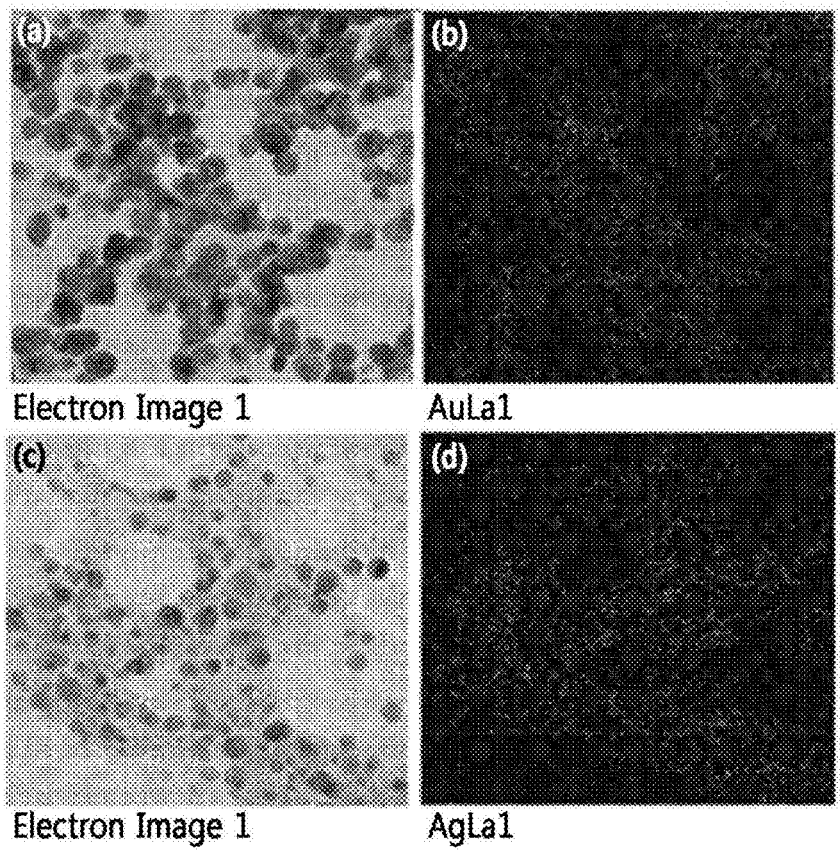

[FIGS. 13A-D]
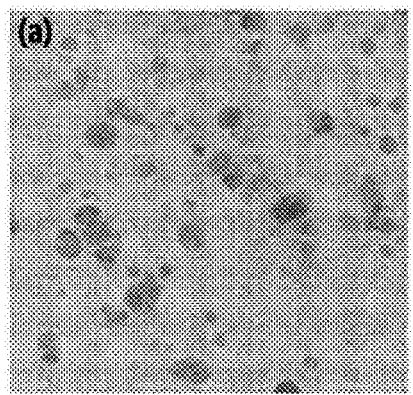 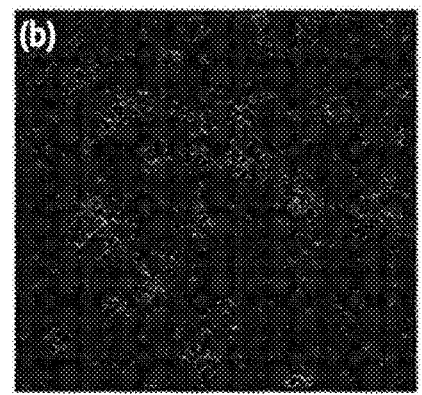
Electron Image 1 | AgLa1
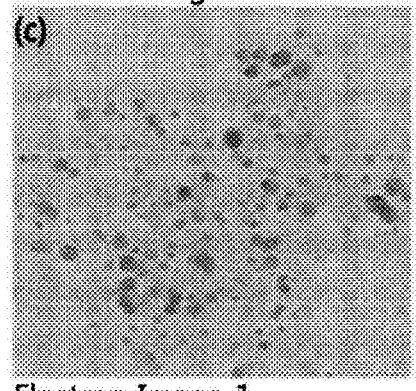 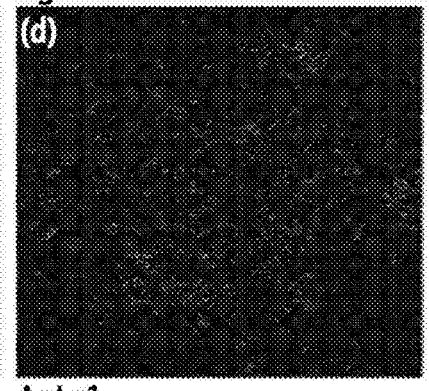
Electron Image 1 | AgLa1

[FIGS. 14A-D]
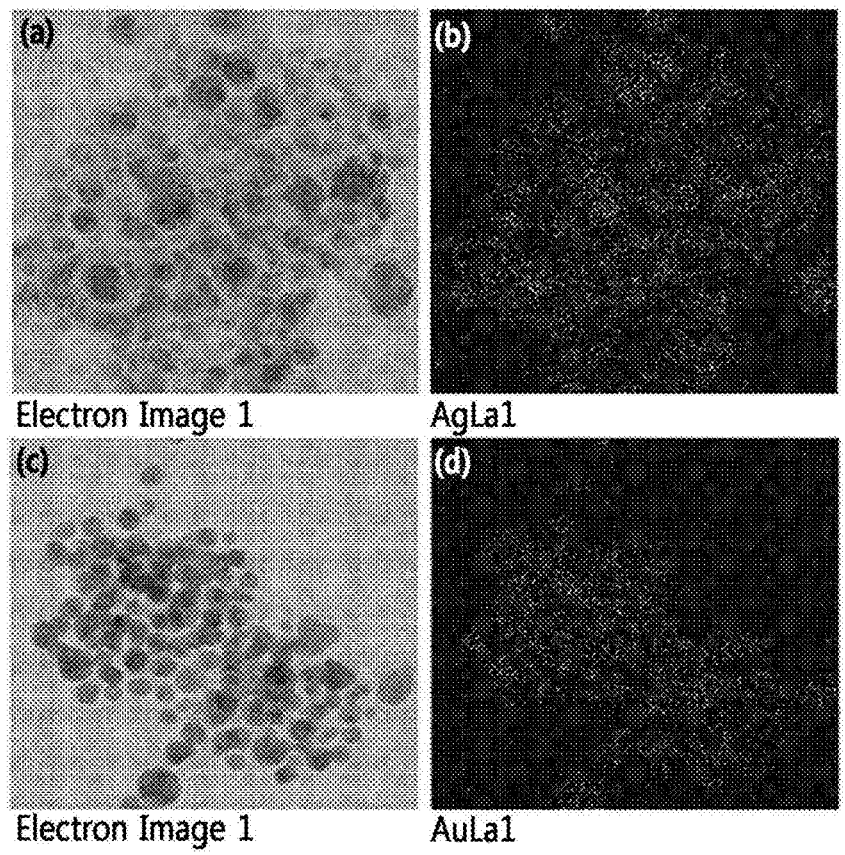

[FIGS. 15A-B]
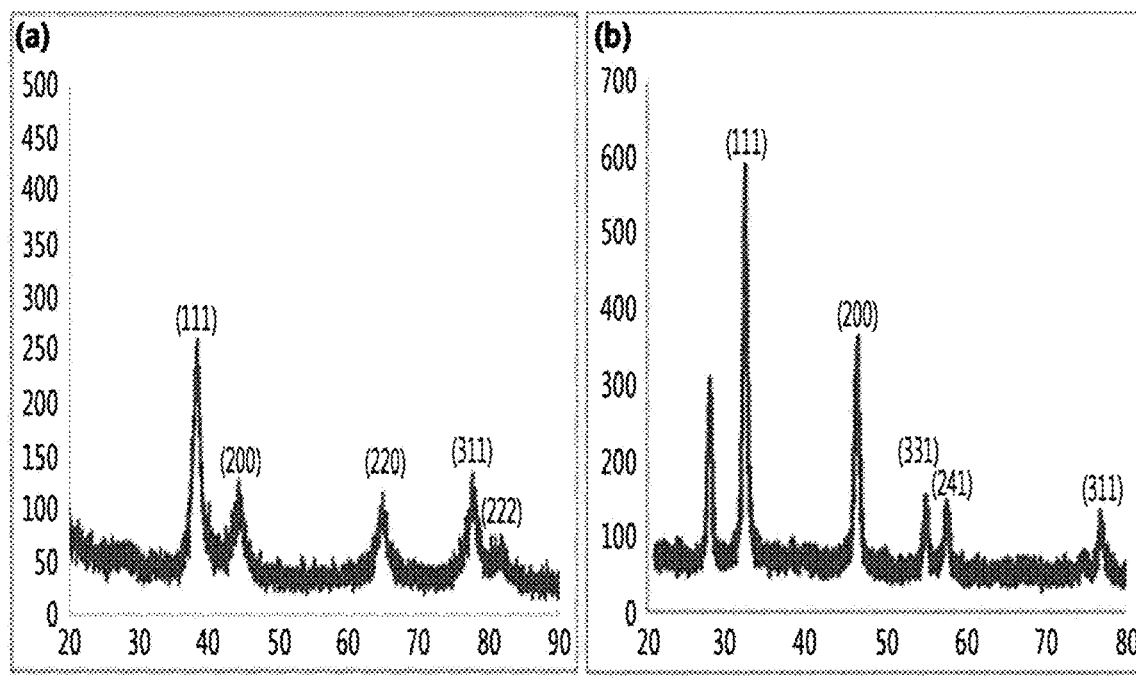
[FIGS. 16A-B]
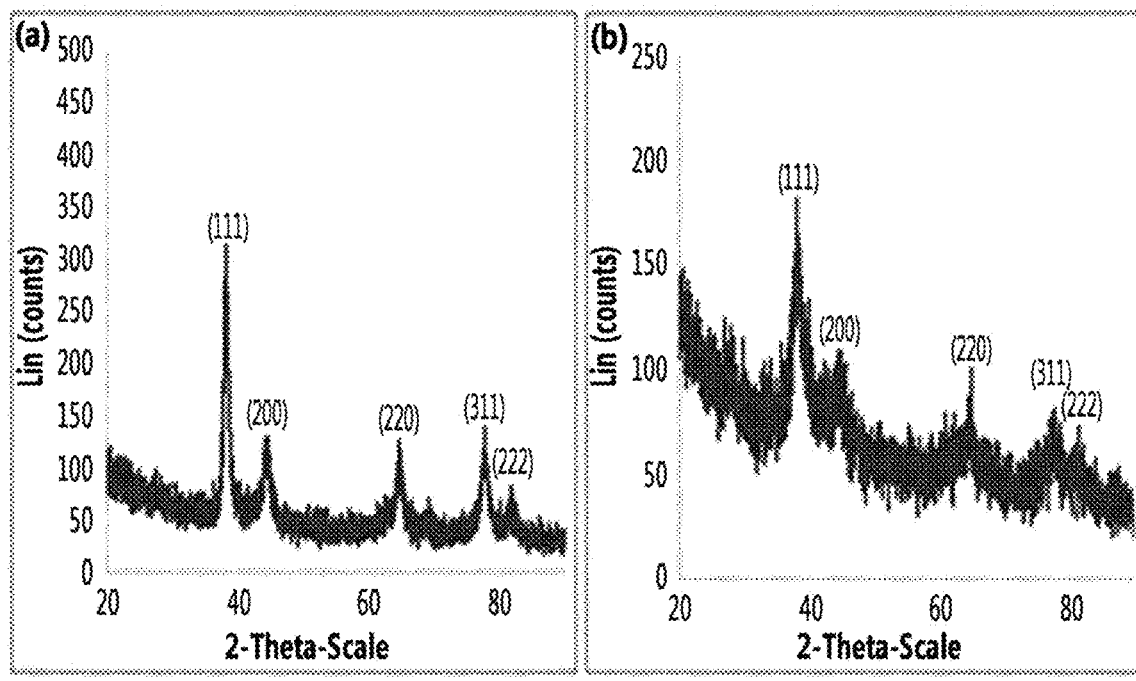

[FIGS. 17A-F]
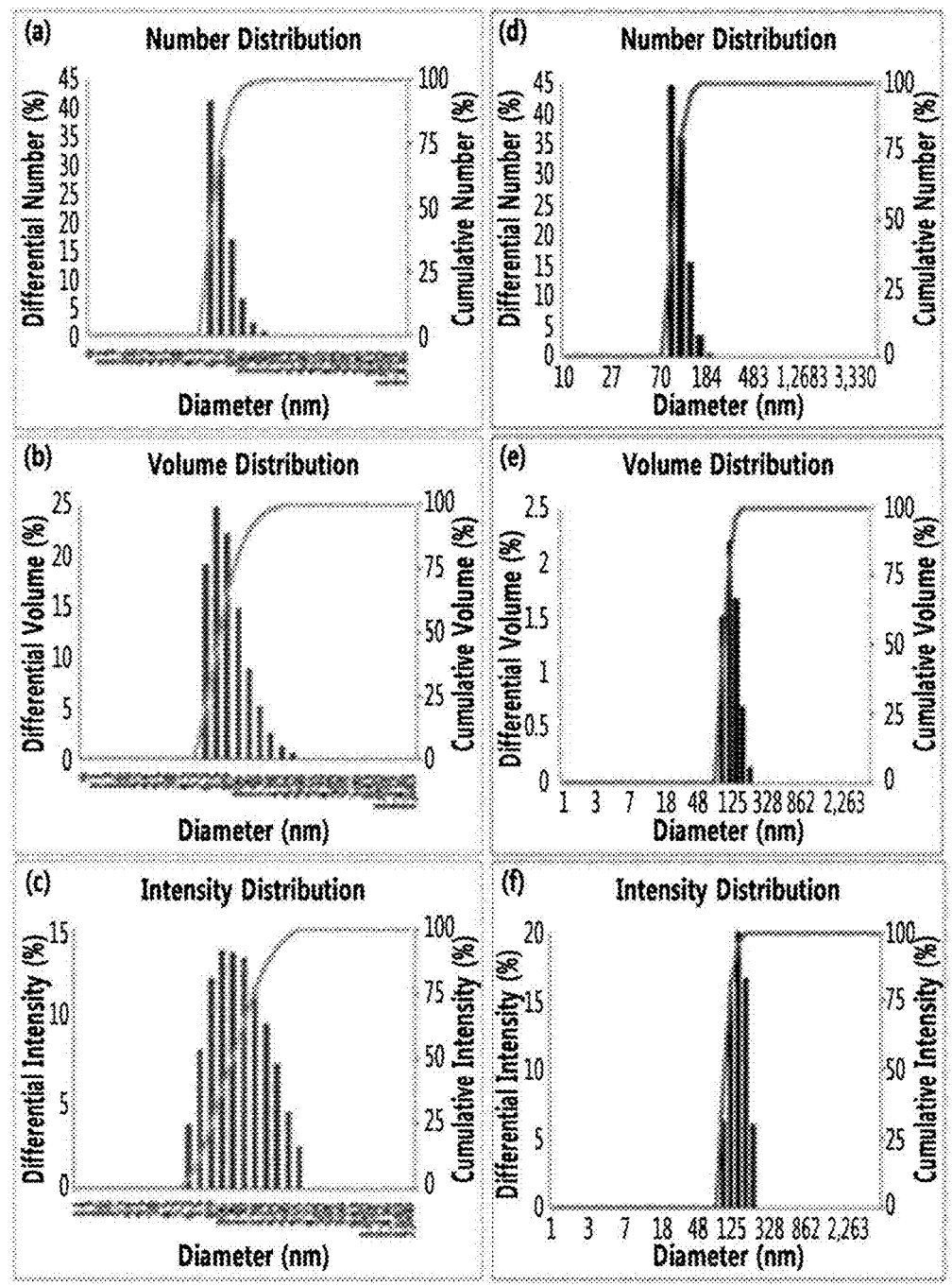

[FIGS. 18A-F]
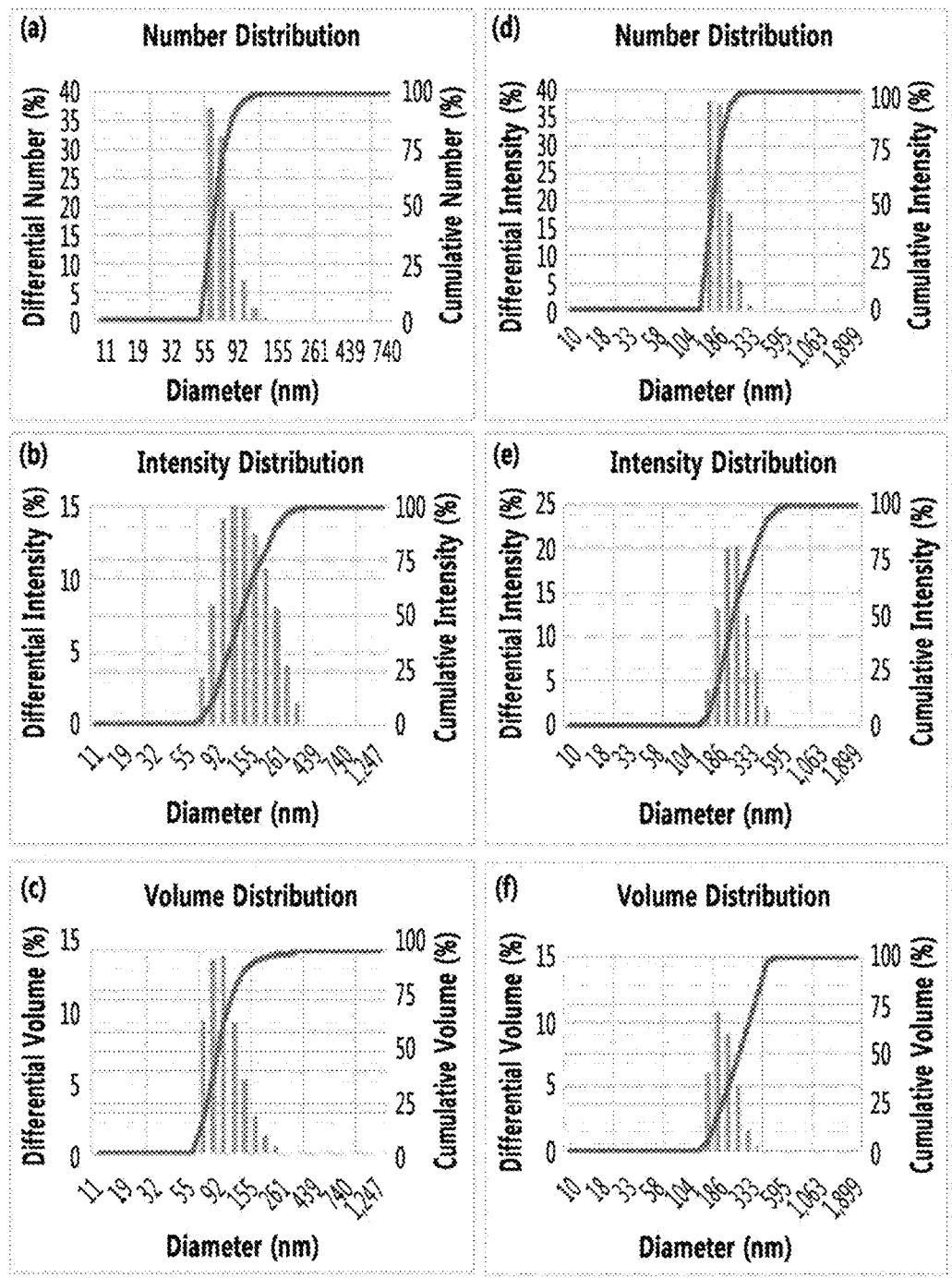

[FIGS. 19A-D]
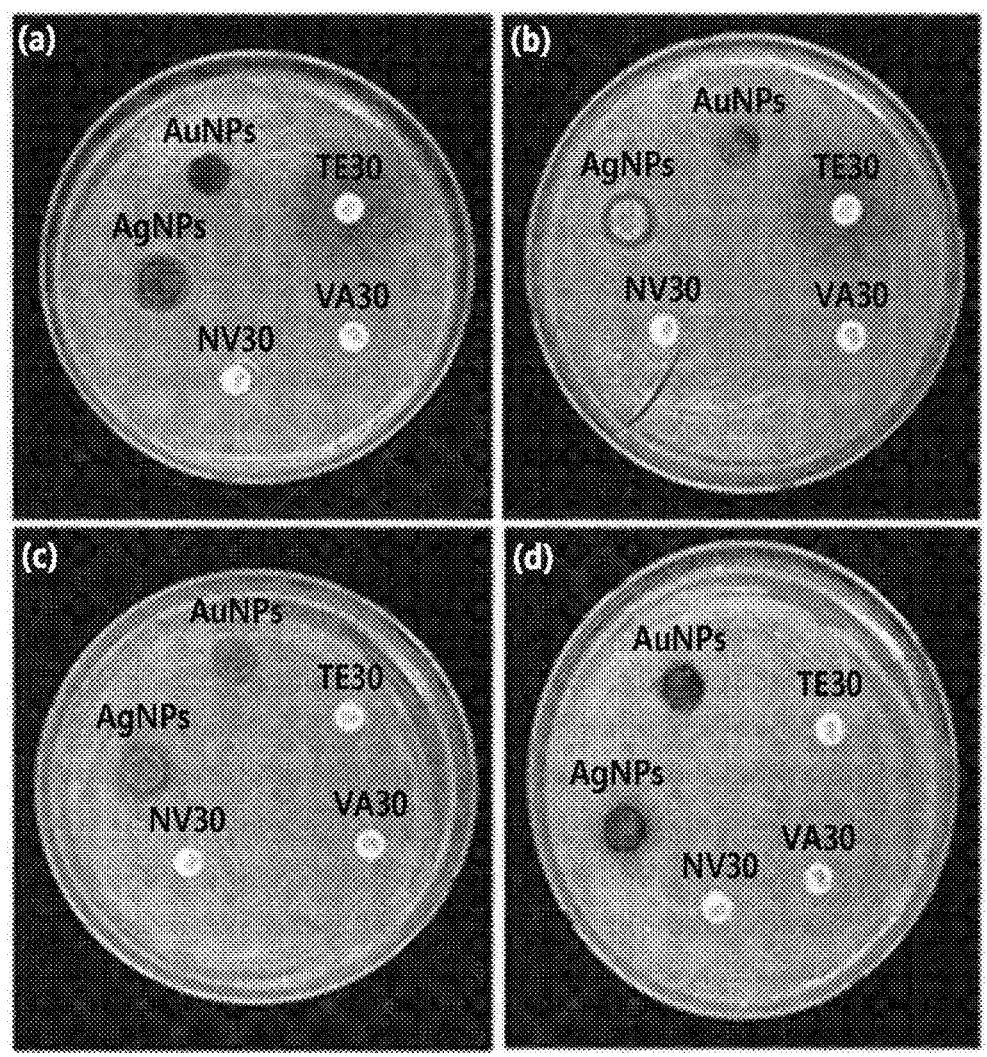

[FIG. 20]
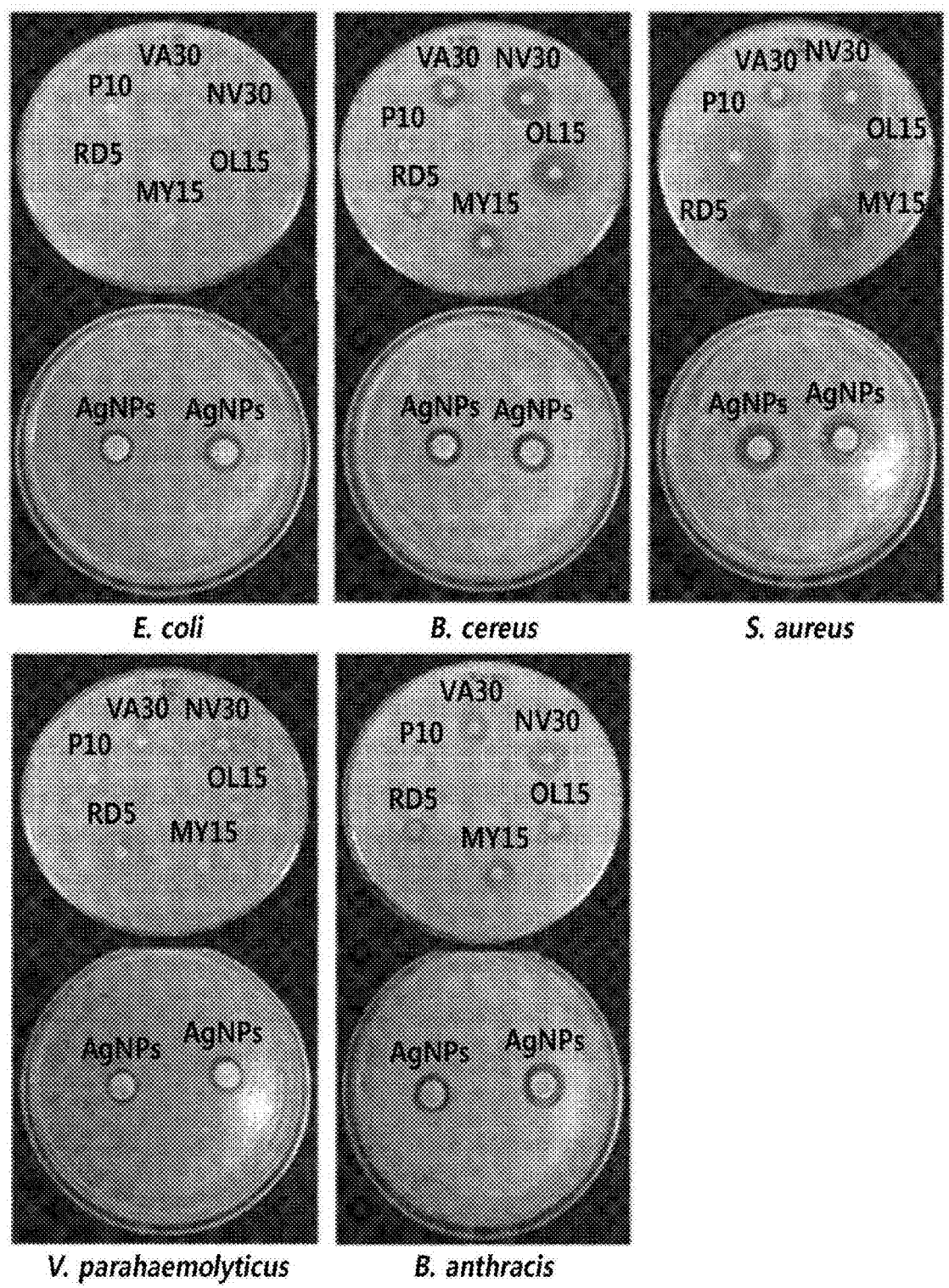

[FIGS. 21A-D]
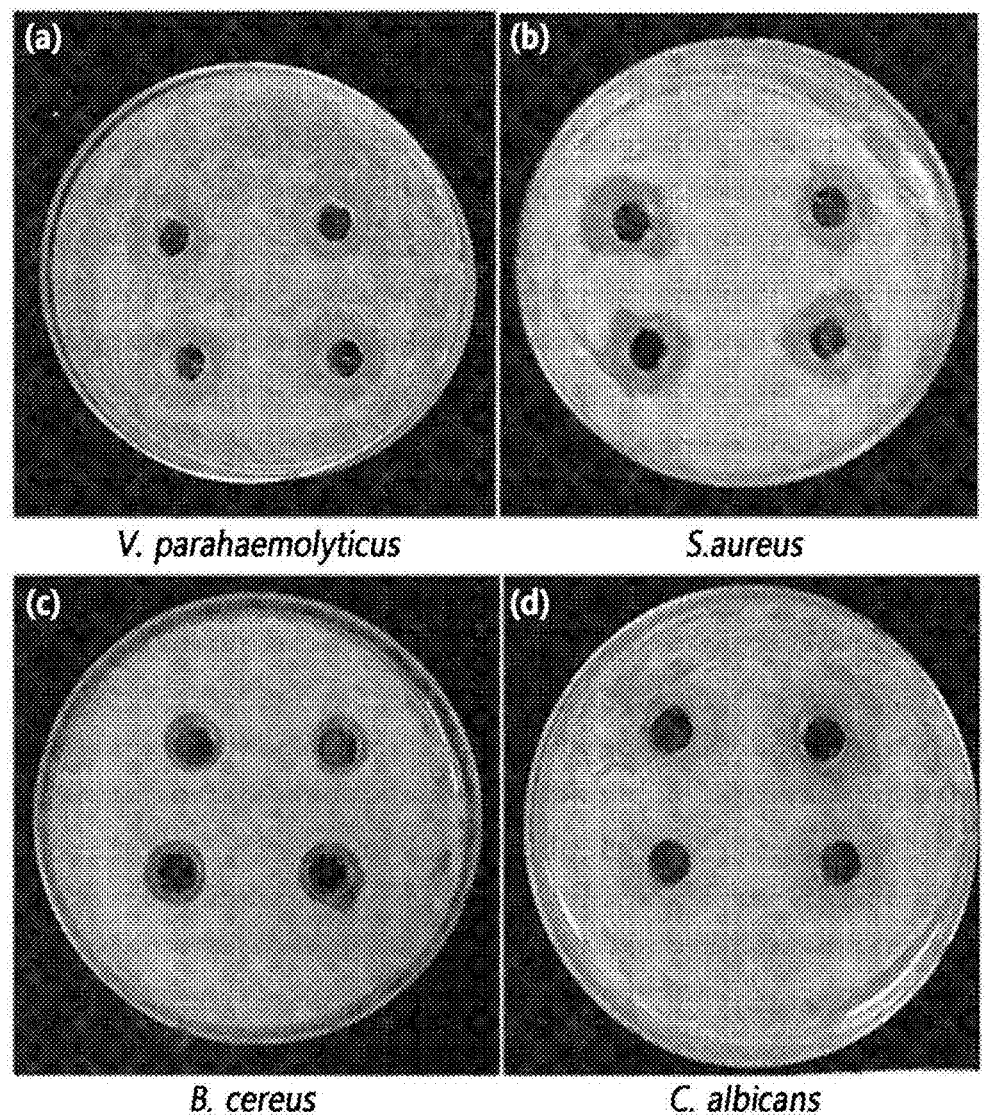

[FIG. 22]
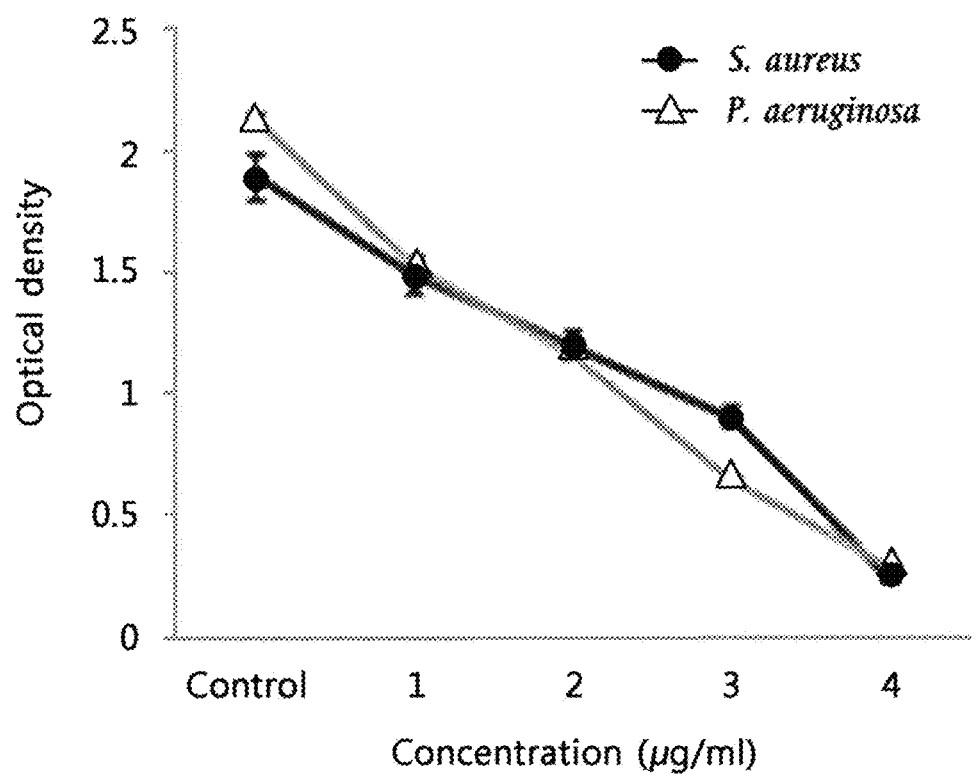

[FIG. 23]
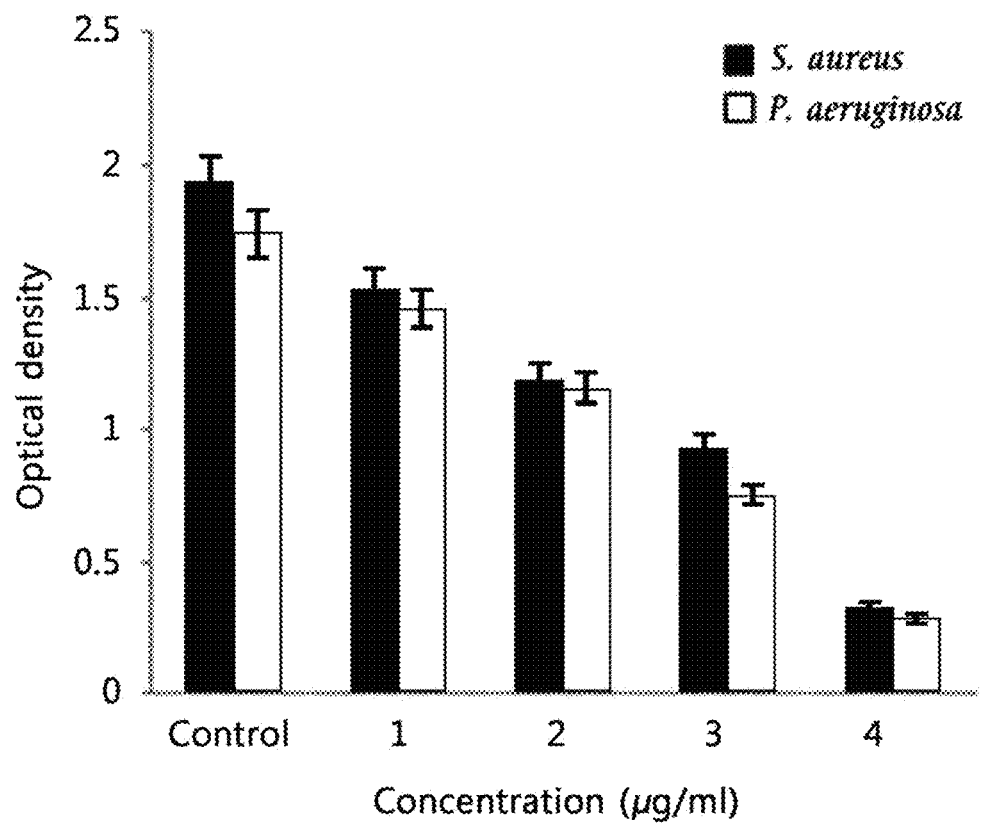
[FIGS. 24A-B]
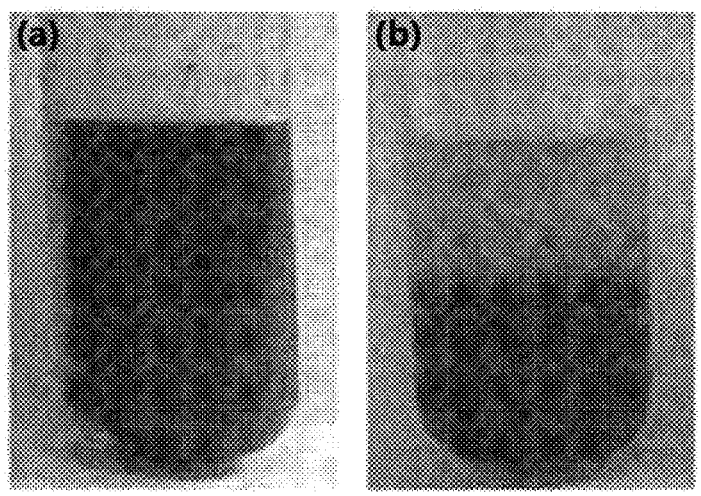

[FIG. 25]
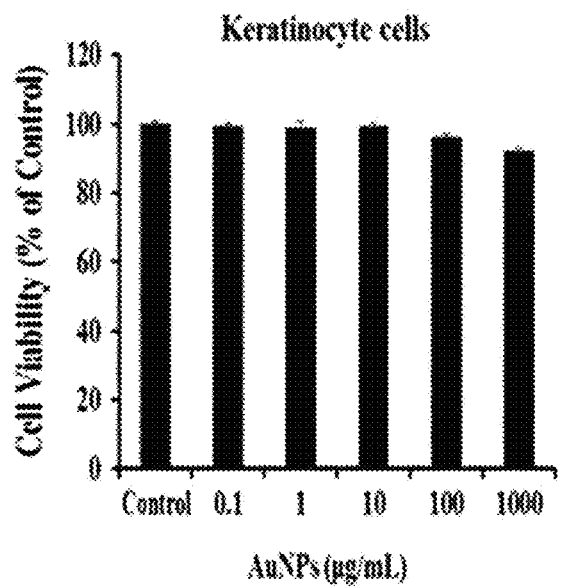
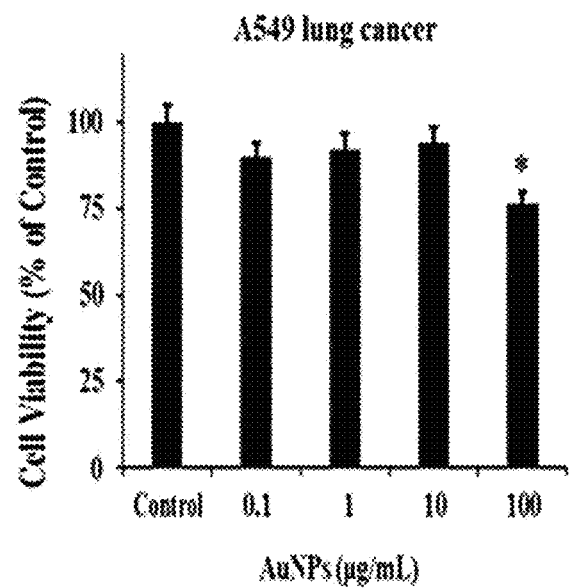
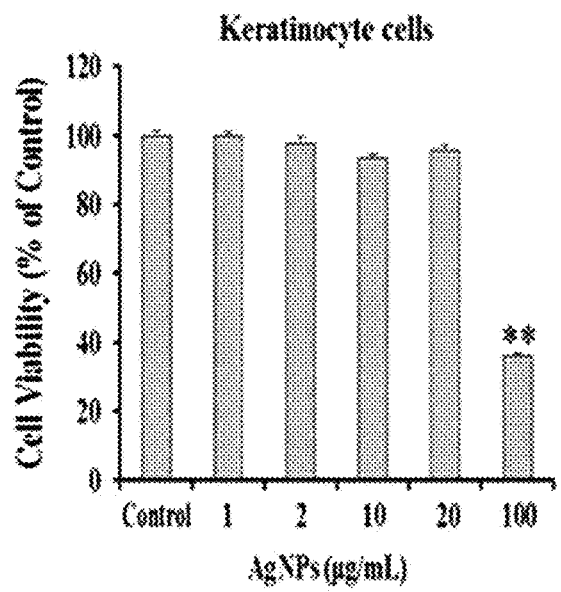
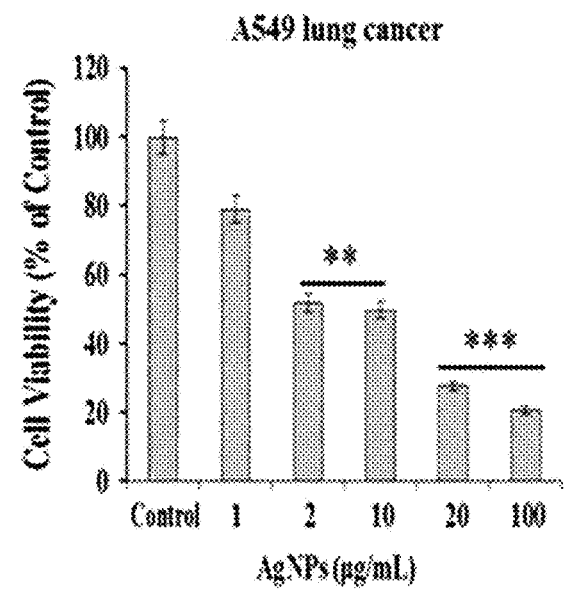

[FIG. 26]
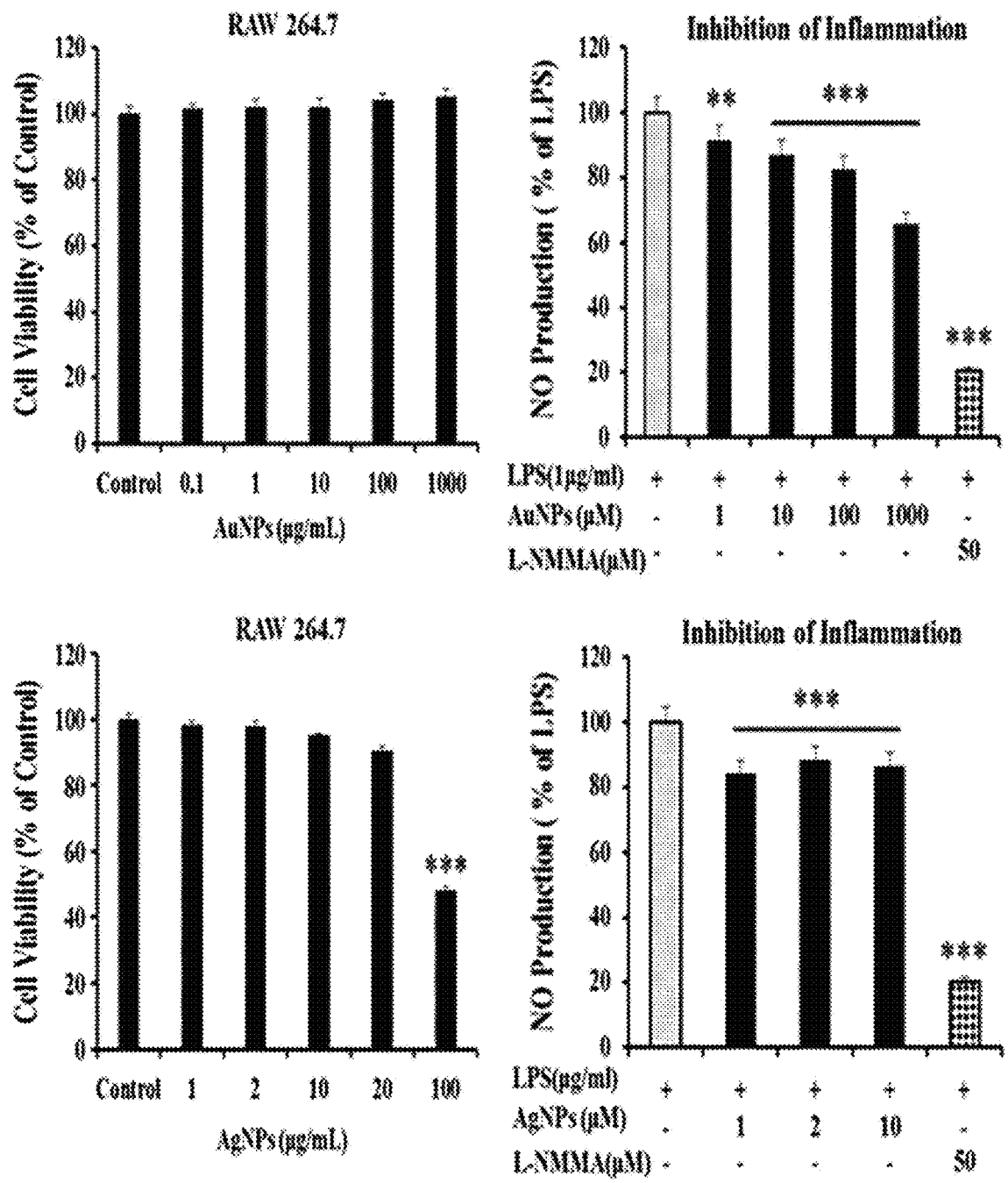

[FIGS. 27A-F]
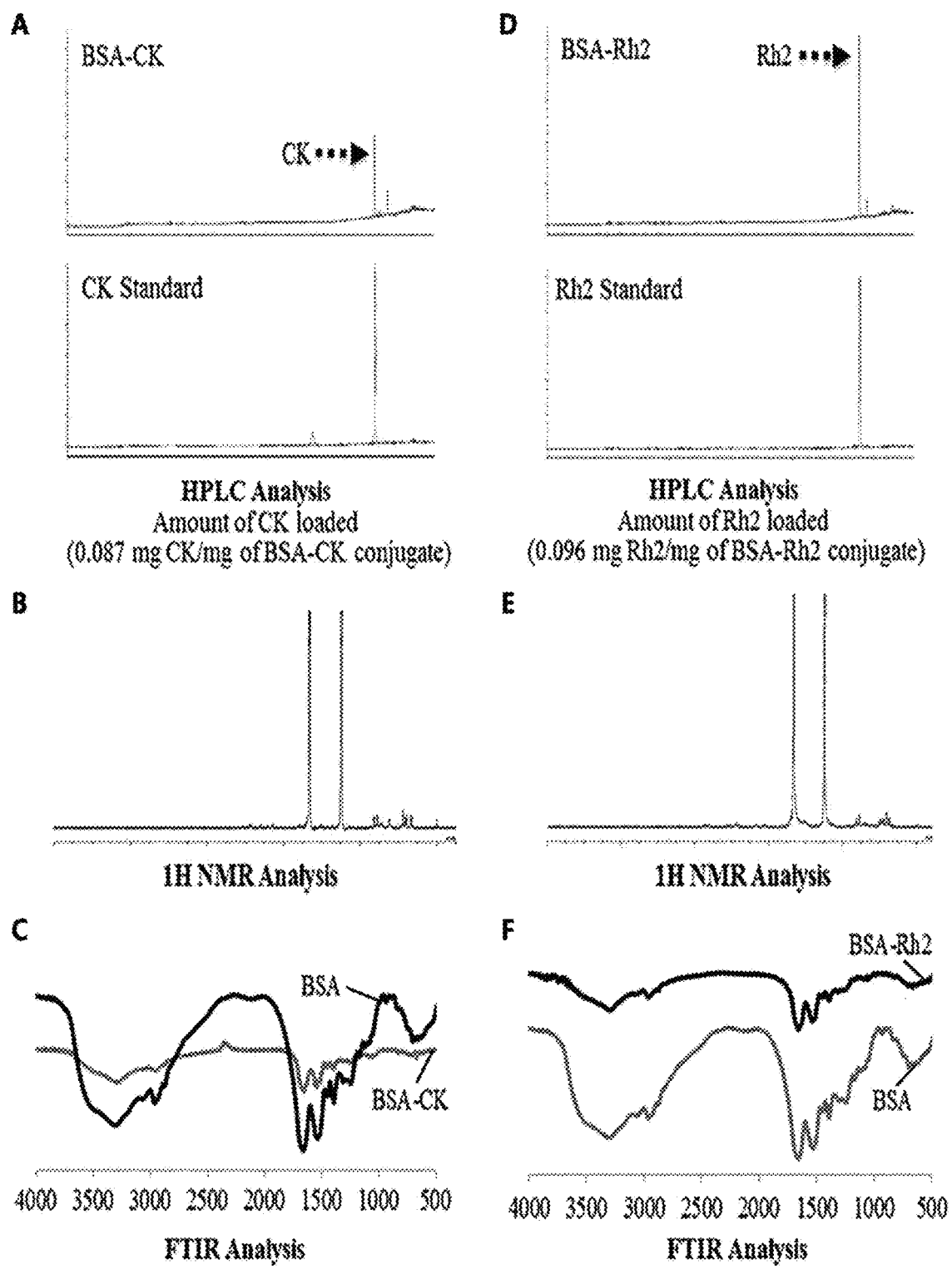

[FIGS. 28A-F]
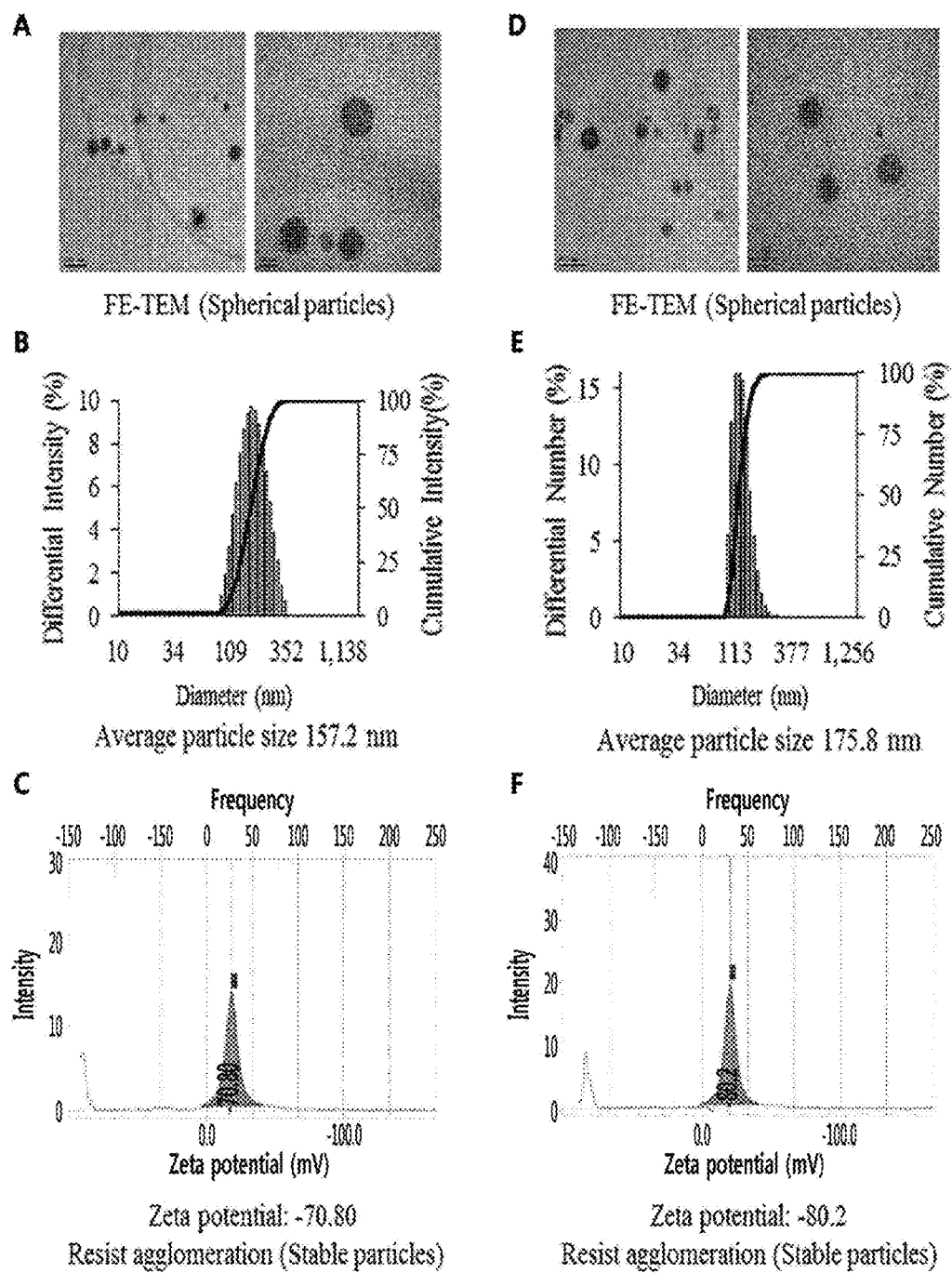

[FIGS. 29A-B]
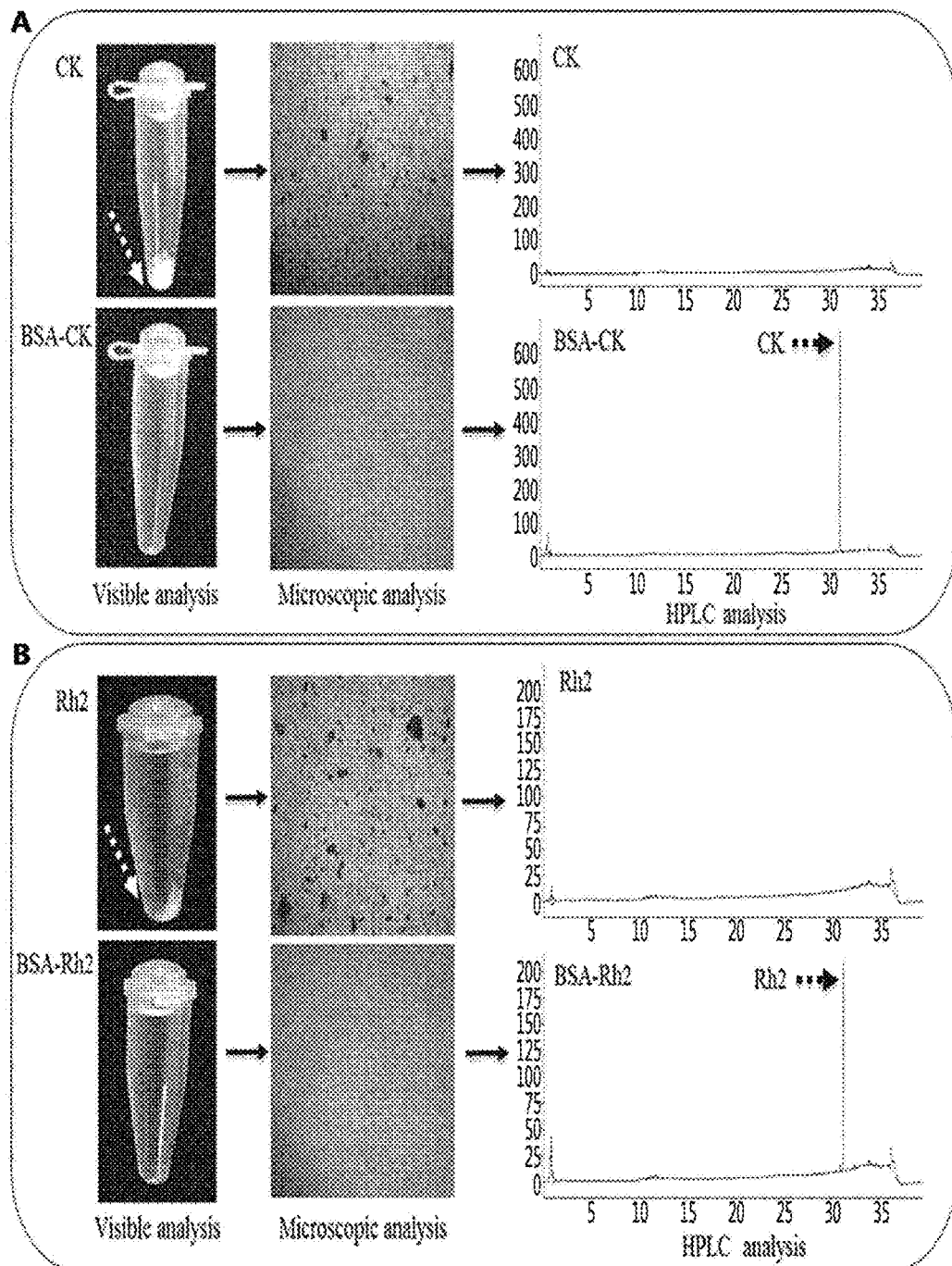

[FIGS. 30A-D]
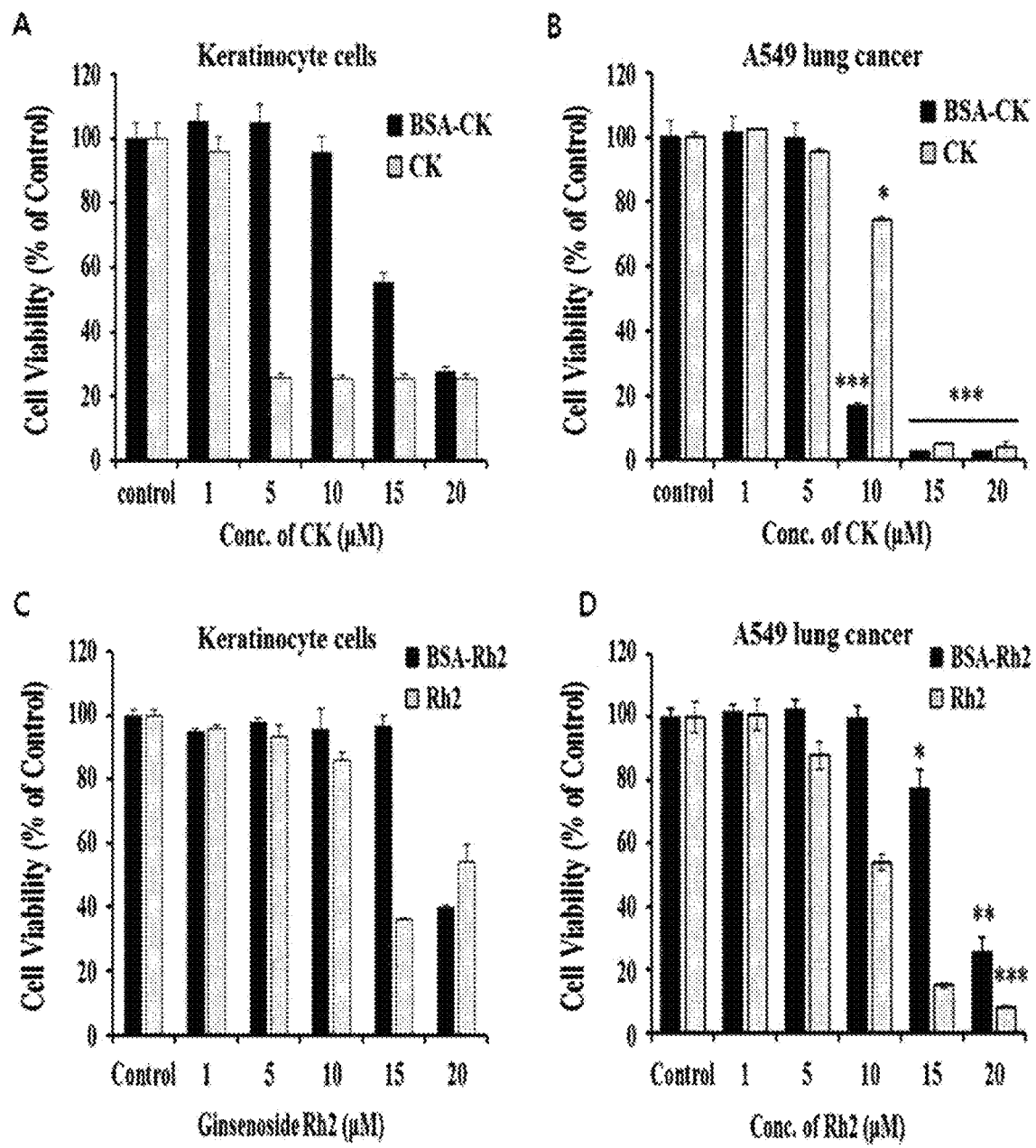

[FIGS. 31A-D]
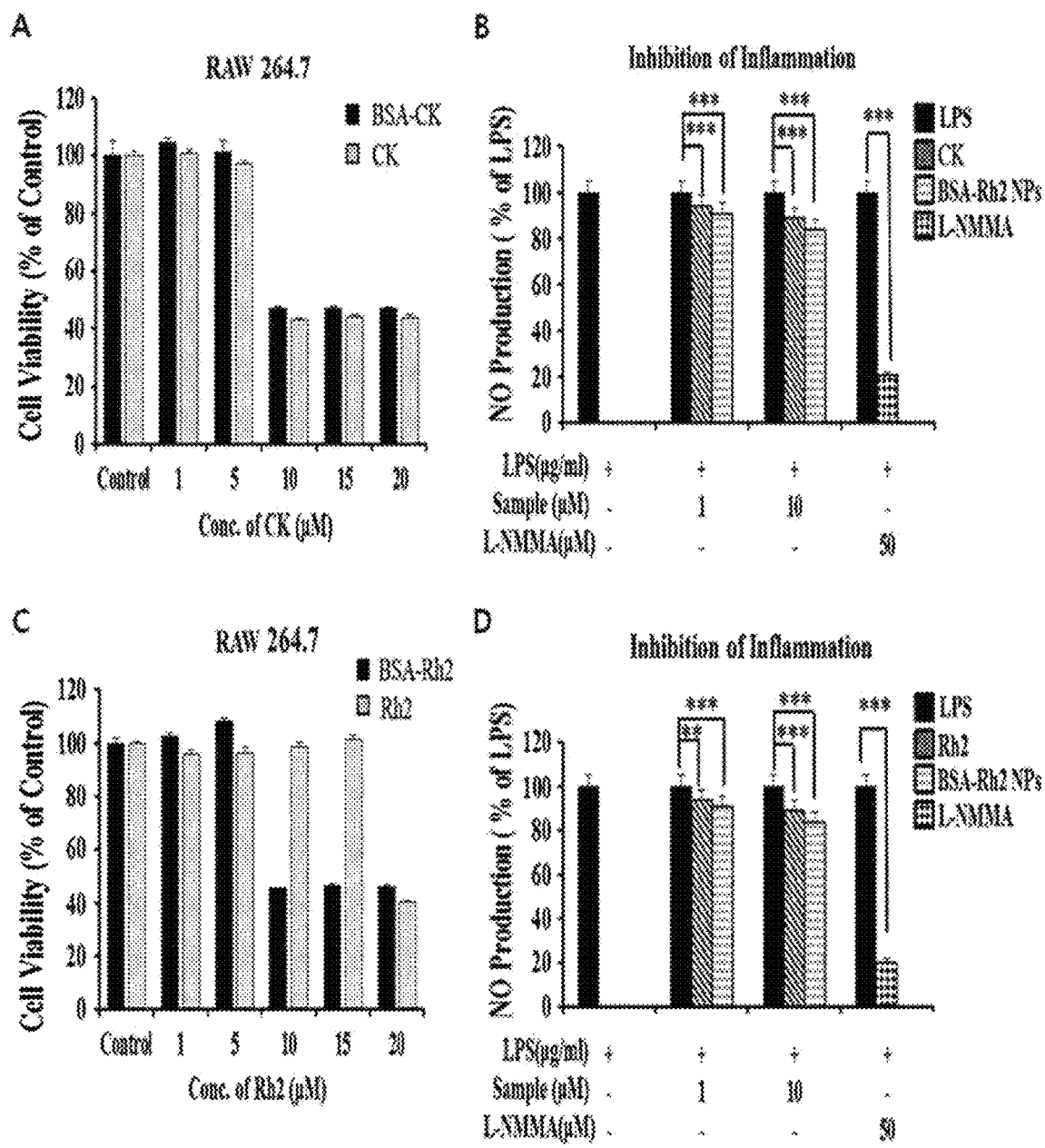

[FIGS. 32A-F]
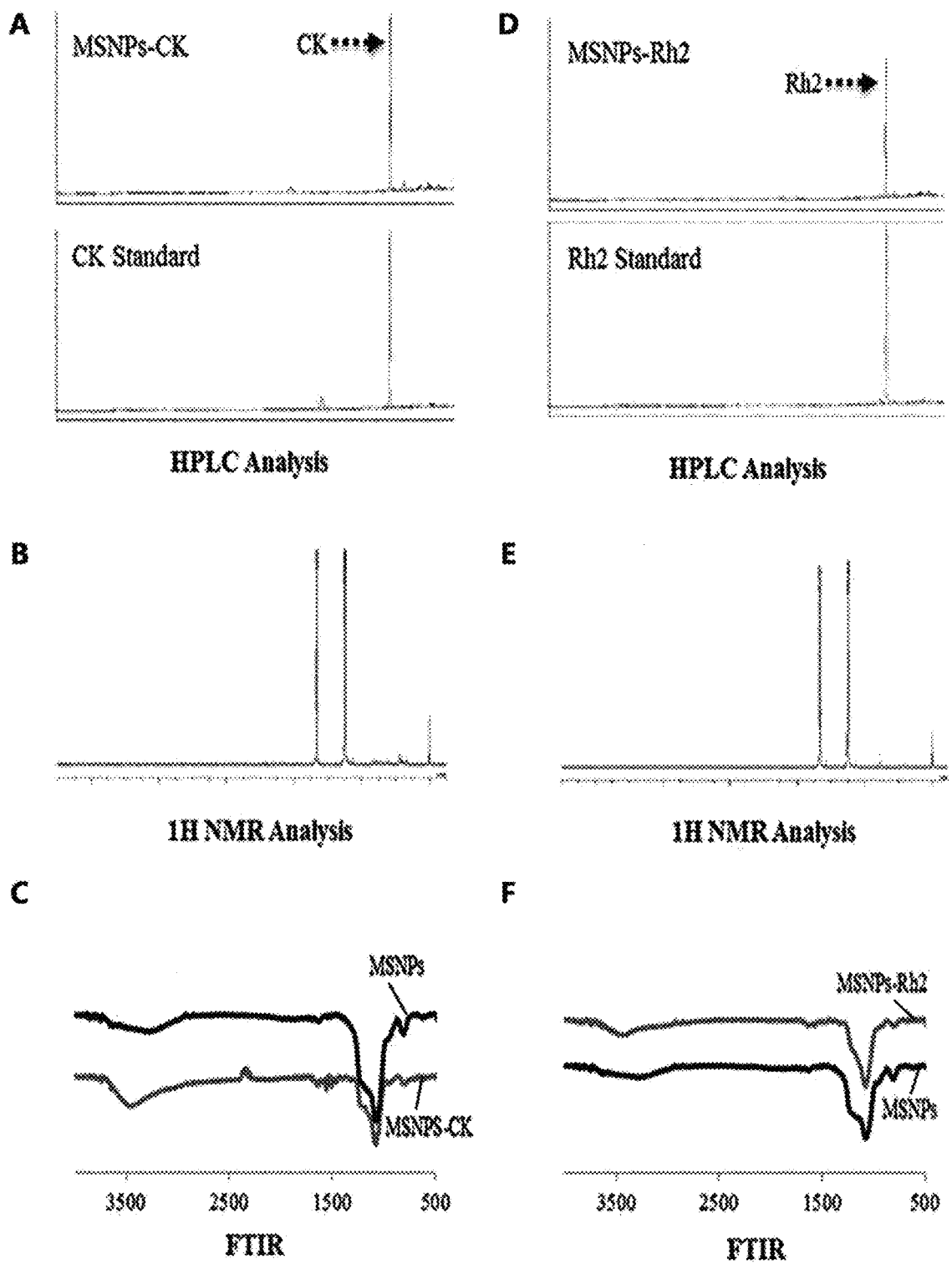

[FIGS. 33A-B]
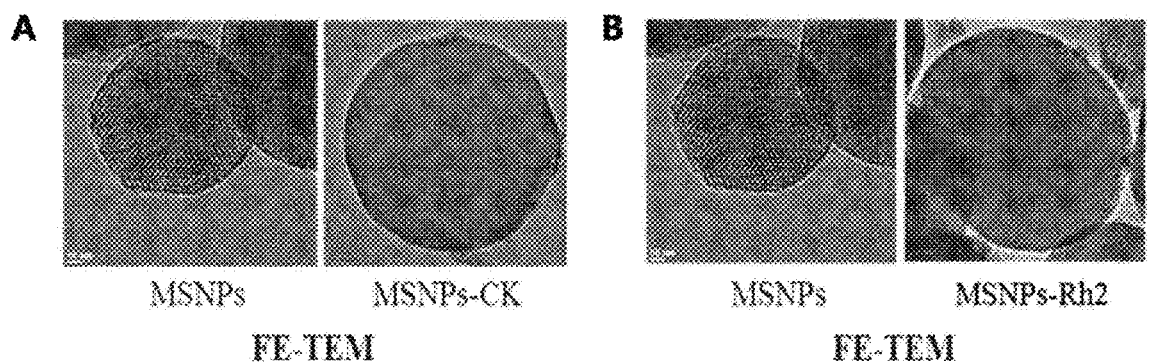

[FIGS. 34A-D]
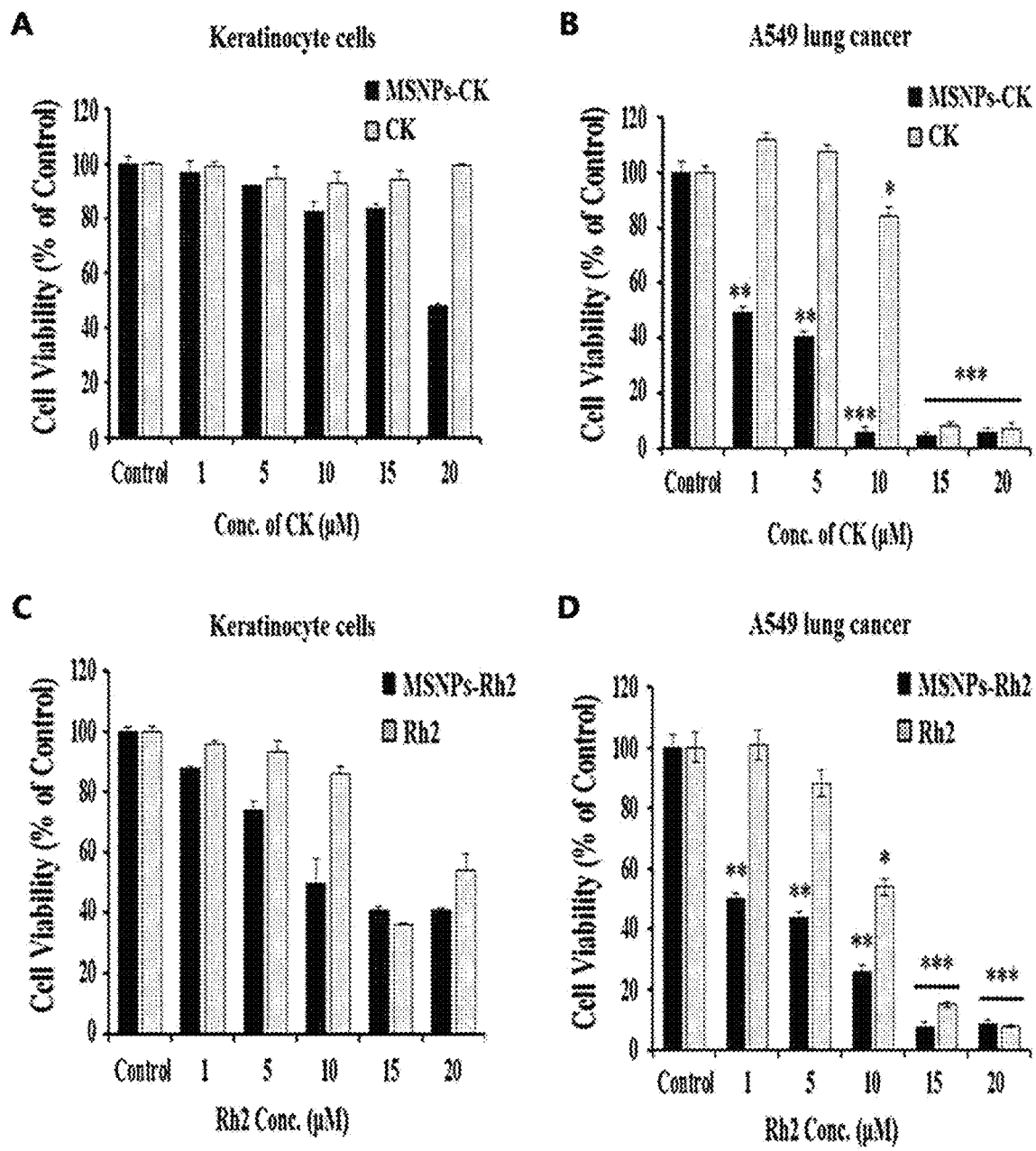

[FIGS. 35A-D]
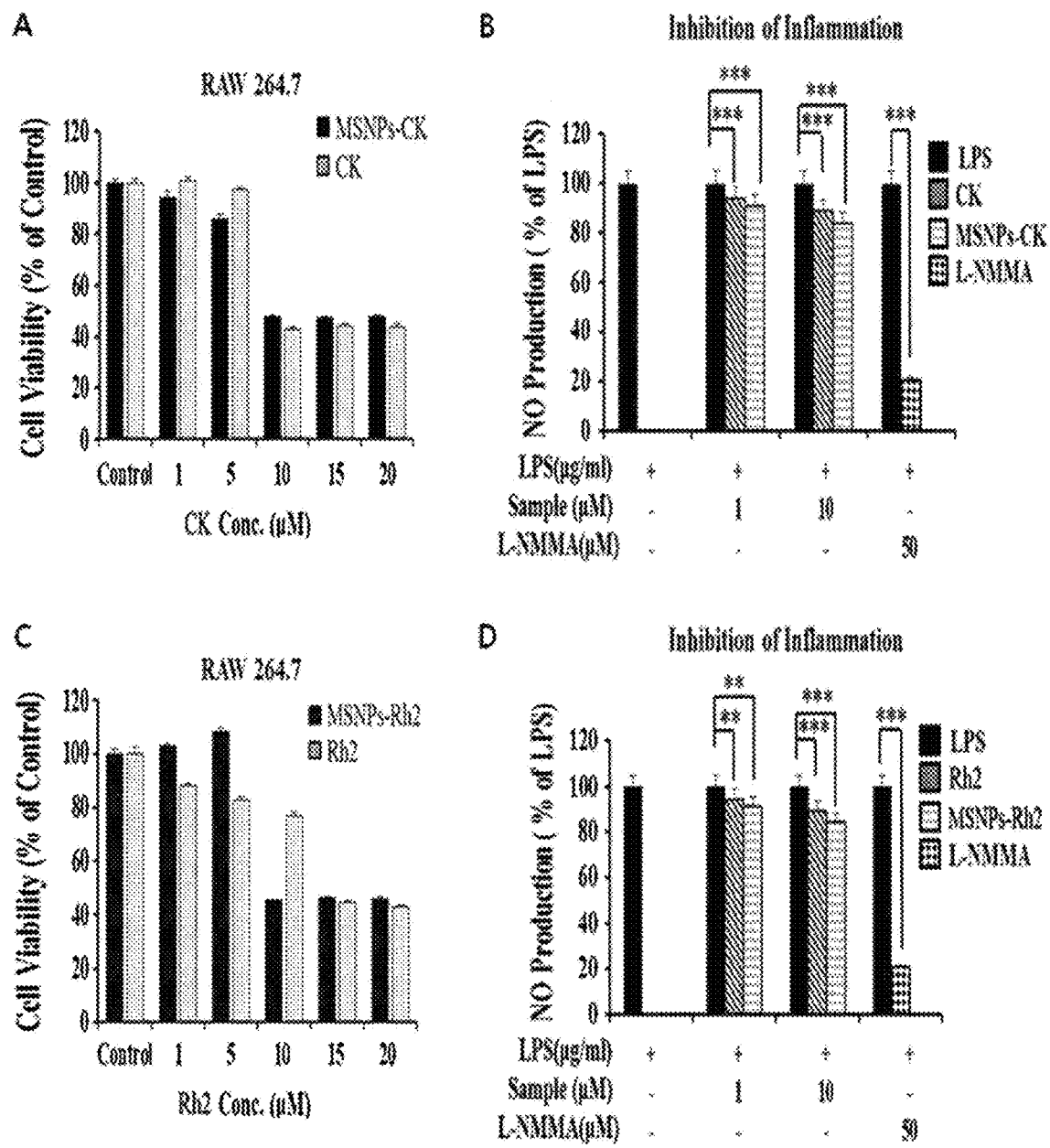

NANO COMPLEX COMPRISING A NANO DRUG DELIVERY MATRIX; AND A GINSENG EXTRACT OR A GINSENOSIDE ISOLATED THEREFROM

This application is a national phase application under 35 U.S.C. § 371 of International Application No. PCT/KR2017/000489, filed Jan. 13, 2017, which claims priority to Korean Application Nos. 10-2016-0004875, filed Jan. 14, 2016, and 10-2016-0043664 and 10-2016- 0043668 both filed Apr. 8, 2016. The entire text of each of the above referenced disclosures is specifically incorporated herein by reference.

BACKGROUND OF THE INVENTION

1. Field of the Invention

The present invention relates to a nanocomposite including a nano-drug delivery system; and a ginseng extract or a ginsenoside isolated therefrom.

2. Description of the Related Art

Ginseng (*Panax ginseng*) is a perennial plant belonging to the Araliaceae family that grows very slowly compared to other plants, and is mostly found in Korea, northeast China, or far eastern Siberia. Ginseng has been cultured and used for many years as a traditional medicinal product such as a tonic, restorative, or anti-aging agent, and its major active ingredient is ginsenoside. It is known that there are more than 40 kinds of ginsenosides, and most ginsenosides have biological and pharmacological activities such as anti-cancer, anti-diabetic, anti-oxidant, and anti-inflammatory activities, alteration and control of immune function, radiation protection, anti-amnesia, anti-apoptosis or anti-stress, etc. Other studies have also reported that some components of ginseng are effective against aging, central nervous system disorders, or neurodegenerative diseases.

Of the various parts of ginseng, the roots or berries are mainly used, as ginseng roots are known to contain a large amount of ginsenosides. In contrast, although ginseng leaves occupy a greater proportion of the entirety of ginseng than the roots, preparation frequency of medicinal products using ginseng leaves is significantly low compared with the use of its roots or berries. However, it has recently been reported that ginseng leaves contain numerous active ingredients such as flavonoids, triterpenoids, polyacetylenic alcohols, ginsenosides, amino acids, peptides, polysaccharides, volatile oils, and fatty acids, and these active ingredients exhibit important pharmacological effects on central nervous system disorders as well as cardiovascular, reproductive, and metabolic systems, and they also have anti-fatigue, anti-hyperglycemia, anti-diabetic, anti-cancer, anti-oxidant, and anti-aging properties (Biomaterials, 2009, 30(10), 1857-69), and therefore, the number of studies on ginseng leaves is gradually increasing. However, there has been no report about the preparation of metal nanoparticles using a ginseng leaf extract.

Further, ginsenosides, which are triterpene saponins, are major active compounds of ginseng (*P. ginseng*), a medicinal herb used in traditional medicines in Korea, China, and Japan. Ginsenosides exhibit a broad range of pharmacological effects, such as anti-tumor, anti-inflammatory, and anti-obesity activities, and protection against Alzheimer's disease, etc. Accordingly, development of therapeutic compositions, such as a composition for promoting angiogenesis, including ginsenoside Rg5 as an active ingredient (Korean Patent Publication No. 2016-0018974), use of ginsenoside F2 in the prevention or treatment of liver diseases (Korean Patent Publication No. 2016-0029894), etc., and development of ginsenoside-related technologies, such as a method of preparing a fermented ginseng or red ginseng extract with enhanced ginsenoside Rd (Korean Patent Publication No. 2016-0018147), a red ginseng preparation with an increased ginsenoside content by using *Metarhizium anisopliae* and a preparation method thereof (Korean Patent Publication No. 2015-0125785), etc., are being actively conducted. However, despite these various pharmacological activities, the efficiency of delivery to target cells is remarkably low, and solubility is also low. Accordingly, there have been many problems in developing ginsenosides as drugs.

Nanotechnology is a rapidly growing field of modern science with potential applications in electrical engineering and biotechnology. Further, in order to overcome the above problems, use of nanocarriers as drug delivery systems has been actively studied.

Among these, metal nanocomposites are considered important because of their unique physicochemical and biological properties in particle size and shape (Colloids Surf B Biointerfaces, 2013, 107, 227-34), and due to their unique electromagnetic, magnetic, catalytic, and optical properties, metal nanocomposites have been widely applied in the biomedical and optical fields, and their importance is gradually increasing.

Among various metals, silver has long been used for the medical treatment of diseases to treat many bacterial infections due to its antimicrobial properties, and silver nanocomposite in a nanoparticle form is known to be less cytotoxic than its ionic form and to enhance the antibacterial effect, and therefore, silver is applied in many fields for anti-bacterial action, anti-inflammation, or prevention of infections. Gold has also been applied to various fields including drug delivery, tissue or tumor imaging, photo thermal therapy, and immune chromatographic identification of pathogens in clinical specimens, biosensor, DNA labeling, vapor sensing, etc. because of its unique and tunable surface plasmon resonance.

In order to prepare these metal nanocomposites, a chemical, physical, or biological synthetic method is generally used. The chemical synthetic method is a relatively simple process. However, it requires high costs and has a problem of side effects of chemical reagents. Further, the physical method has drawbacks in that size control of nanoparticles is difficult and expensive manufacturing equipment is required, and therefore, it is difficult to effectively prepare metal nanocomposites.

For this reason, a method of preparing metal nanocomposites by using a bacterium or a microbial strain or a method of preparing eco-friendly metal nanocomposites including a natural extract as an active ingredient has recently been studied. However, the method of synthesizing metal nanocomposites by using a bacterium or a microbial strain has disadvantages in that a long period of time of one to several days is required for the synthesis, and a reducing agent or a capping agent such as a stabilizing agent is additionally needed for stabilization of synthesized nanoparticles. Accordingly, there is a continuous demand for developing metal nanocomposites which are eco-friendly and stable at the same time and overcome the limit of preparation time, as compared with the chemical or physical synthetic method.

Further, many different nanocarriers have been developed based on organic platforms (liposomes, polymers, dendrimers, etc.) and inorganic systems (gold, semiconductor nanocrystals, magnetic NP, silica particles, etc.). Among these, mesoporous silica nanoparticle (MSNP), which is a nanocarrier based on an inorganic material, has notable characteristics as a drug carrier.

Specifically, abundant silanol groups (Si—OH) present on the surface of MSNPs facilitate post-synthesis modifications, thus simplifying the design of a drug delivery system, and MSNPs are resistant to hydrolysis and enzymatic degradation, and can thereby load a drug at a high level. Since most enzymatic proteins have diameters considerably greater than the nanopores of MSNPs, the narrow boundaries of the nanopores provide a physical barrier to inhibit enzyme entry. Hence, drugs trapped in or conjugated to the inner walls of MSNPs may be protected from in vivo hydrolysis and premature release.

Polymeric proteins have attracted attention as a promising drug delivery system to overcome the above-mentioned problems of anti-cancer agents, because drugs conjugated to the proteins are preferentially absorbed by cancer cells or inflammatory tissue. Further, charged groups of proteins aid in the physical capture of drug molecules by the proteins, and these characteristics of proteins make it possible to use proteins as candidates for ideal drug delivery.

Recently, many studies have been conducted for clinical application of albumin-based nanoparticles. Albumin is a plasma protein and contributes to various biological processes. Plasma albumin has a unique ligand-delivery property that imparts enhanced solubility for serum albumin-conjugated hydrophobic drugs and helps improve the pharmacokinetic properties of drug molecules in biological environments. Thus, many drugs have been developed by using albumin, and specifically, Abraxane (paclitaxel-albumin NPs) developed by Nab™ as a therapeutic agent for non-small-cell lung cancer and breast cancer has been approved by the U.S. FDA. In addition, about seven albumin-based drugs or imaging agents have been introduced to the market, and about ten products have been clinically applied for the treatment of cancer, diabetes, hepatitis C, and rheumatoid arthritis (Yu et al., 2014; Zhao et al., 2015).

With this background, the present inventors developed a method of preparing metal nanocomposites using a ginseng extract, wherein the metal nanocomposites may be stably prepared in a uniform size without using an additional reducing agent or stabilizing agent in a significantly shortened time, as compared with the known methods, and they found that a composition including the metal nanocomposites prepared by the method has anti-microbial activity, biofilm-degrading activity, anti-coagulant activity, anti-cancer activity, and anti-inflammatory activity.

Further, the present inventors have made extensive efforts to develop a ginsenoside drug substance which is improved in targeting ability for cancer cells and half-life, and as a result, they found that nanocomposites in which ginsenosides are conjugated to nanoparticles have a high solubility for water or selective drug release patterns depending on pH, and have high anti-cancer and anti-inflammatory activities, thereby completing the present invention.

SUMMARY OF THE INVENTION

An object of the present invention is to provide a nanocomposite including a nano-drug delivery system; and a ginseng extract or a ginsenoside isolated therefrom.

Another object of the present invention is to provide a pharmaceutical composition for preventing or treating cancer, including the nanocomposites.

Still another object of the present invention is to provide a pharmaceutical composition for preventing or treating an inflammatory disease, including the nanocomposites.

Still another object of the present invention is to provide a method of treating cancer, the method including the step of administering the nanocomposites to a patient.

Still another object of the present invention is to provide a method of treating an inflammatory disease, the method including the step of administering the nanocomposites to a patient.

Still another object of the present invention is to provide a method of preparing the nanocomposites, the method including the step of mixing and reacting the nano-drug delivery system; and the ginseng extract or the ginsenoside isolated therefrom.

BRIEF DESCRIPTION OF THE DRAWINGS

FIGS. 1A-G show color changes after reacting ginseng leaf extracts (A to C), ginseng root extracts (D and E), or red ginseng extracts (F and G) with a gold (III) chloride trihydrate ($HAuCl_4.3H_2O$) or silver nitrate solution (control: control group, AgNPs: silver nanocomposite, AuNPs: gold nanocomposite);

FIGS. 2A-B show UV-vis spectra to confirm whether or not gold or silver nanocomposites prepared using the ginseng leaf extract were formed;

FIGS. 3A-B show UV-vis spectra to confirm whether or not gold or silver nanocomposites prepared using the ginseng root extract were formed;

FIGS. 4A-B show UV-vis spectra to confirm whether or not gold or silver nanocomposites prepared using the red ginseng root extract were formed;

FIGS. 5A-H show FE-TEM images to confirm structural characteristics of gold or silver nanocomposites prepared using the ginseng leaf extract;

FIGS. 6A-D show FE-TEM images to confirm structural characteristics of gold or silver nanocomposites prepared using the ginseng root extract;

FIGS. 7A-F show FE-TEM images to confirm monodispersity of the structural characteristics of gold or silver nanocomposites prepared using the ginseng root extract and fringe spacing of the nanocomposites;

FIGS. 8A-B show FE-TEM images to confirm the structural characteristics of gold or silver nanocomposites prepared using the red ginseng root extract;

FIGS. 9A-B show EDAX analysis to confirm purity of gold or silver nanocomposites prepared using the ginseng leaf extract;

FIGS. 10A-B show EDAX analysis to confirm purity of gold or silver nanocomposites prepared using the ginseng root extract;

FIGS. 11A-B show EDAX analysis to confirm purity of gold or silver nanocomposites prepared using the red ginseng leaf extract;

FIGS. 12A-D show TEM images to analyze elemental mapping results of gold or silver nanocomposites prepared using the ginseng leaf extract;

FIGS. 13A-D show TEM images to analyze elemental mapping results of gold or silver nanocomposites prepared using the ginseng root extract;

FIGS. 14A-D show TEM images to analyze elemental mapping results of gold or silver nanocomposites prepared using the red ginseng root extract;

FIGS. 15A-B show X-ray diffraction to confirm diffraction patterns of gold or silver nanocomposites prepared using the ginseng leaf extract;

FIGS. 16A-B show X-ray diffraction to confirm diffraction patterns of gold or silver nanocomposites prepared using the ginseng root extract;

FIGS. 17A-F show dynamic light scattering analysis to confirm size distribution profiles based on volume, intensity, and number of gold or silver nanocomposites prepared using the ginseng leaf extract;

FIGS. 18A-F show dynamic light scattering analysis to confirm size distribution profiles based on volume, intensity, and number of gold or silver nanocomposites prepared using the red ginseng root extract;

FIGS. 19A-D shows antimicrobial activities of gold or silver nanocomposites prepared using the ginseng leaf extract;

FIG. 20 shows antimicrobial activities of silver nanocomposites prepared using the ginseng root extract;

FIGS. 21A-D shows antimicrobial activities of silver nanocomposites prepared using the red ginseng root extract;

FIG. 22 shows biofilm-degrading activities of silver nanocomposites prepared using the ginseng leaf extract;

FIG. 23 shows biofilm-degrading activities of silver nanocomposites prepared using the red ginseng root extract;

FIGS. 24A-B show anticoagulant activities of gold or silver nanocomposites prepared using the ginseng leaf extract;

FIG. 25 shows cytotoxicity of gold or silver nanocomposites prepared using the ginseng leaf extract on keratinocyte cells and lung cancer cells (A549 cells);

FIG. 26 shows anti-inflammatory activities of gold or silver nanocomposites prepared using the ginseng leaf extract;

FIGS. 27A-F show preparation results of BSA-CK and BSA-Rh2, in which A to C are for BSA-CK and D to F are for BSA-Rh2, and specifically, A and D show HPLC analysis results of the two nanocomposites, B and E show $^1$H NMR spectra, and C and F show FTIR spectra;

FIGS. 28A-F show physicochemical properties of BSA-CK and BSA-Rh2, in which A to C are for BSA-CK and D to F are for BSA-Rh2, and specifically, A and D show FE-TEM images, B and E show results of particle size distribution analysis, and C and F show results of zeta potential analysis;

FIGS. 29A-B show microscopic images and results of HPLC analysis of supernatants to analyze solubilities of BSA-CK and BSA-Rh2 for water, in which A represents solubility of CK alone or BSA-CK, and B represents solubility of Rh2 alone or BSA-Rh2;

FIGS. 30A-D show cytotoxicity graphs of BSA-CK and BSA-Rh2 on A549 lung cancer cells or keratinocyte cells, in which A and B represent results of BSA-CK, C and D represent results of BSA-Rh2, statistical significance was determined by student's t-test, and values of P<0.05 were considered statistically significant, marked with an asterisk (*);

FIGS. 31A-D show anti-inflammatory activities of BSA-CK and BSA-Rh2, confirmed by cytotoxicity on murine macrophage cell line RAW 264.7 and inhibitory effect on LPS-induced NO production, in which in the analysis of a NO production-inhibitory effect, a NO synthase inhibitor, L-NMMA (N$^G$-monomethyl L-arginine), was used as a positive control, and A and B represent results of BSA-CK, C and D represent results of BSA-Rh2, statistical significance was determined by student's t-test, and values of P<0.05 were considered statistically significant, marked with an asterisk (*);

FIGS. 32A-F show preparation results of MSNP-CK and MSNP-Rh2, in which A to C are for MSNP-CK and D to F are for MSNP-Rh2, and specifically, A and D show HPLC analysis results of the two nanocomposites, B and E show $^1$H NMR spectra, and C and F show FTIR spectra;

FIGS. 33A-B show FE-TEM images of MSNP-CK and MSNP-Rh2, in which A is for MSNP-CK and B is for MSNP-Rh2;

FIGS. 34A-D show cytotoxicity graphs of MSNP-CK and MSNP-Rh2 on A549 lung cancer cells or keratinocyte cells, in which A and B represent results of MSNP-CK, C and D represent results of MSNP-Rh2, statistical significance was determined by student's t-test, and values of P<0.05 were considered statistically significant, marked with an asterisk (*); and FIGS. 35A-D show anti-inflammatory activities of MSNP-CK and MSNP-Rh2, confirmed by cytotoxicity on murine macrophage cell line RAW 264.7 and an inhibitory effect on LPS-induced NO production, in which in the analysis of a NO production-inhibitory effect, a NO synthase inhibitor, L-NMMA (N$^G$-monomethyl L-arginine), was used as a positive control, and A and B represent results of MSNP-CK, C and D represent results of MSNP-Rh2, statistical significance was determined by student's t-test, and values of P<0.05 were considered statistically significant, marked with an asterisk (*).

DETAILED DESCRIPTION OF THE PREFERRED EMBODIMENTS

In order to achieve the above objects, an aspect of the present invention provides a nanocomposite including a nano-drug delivery system; and a ginseng extract or a ginsenoside isolated therefrom.

As used herein, the term "ginseng" refers to perennial a plant belonging to the Araliaceae family that grows very slowly compared to other plants, which is mostly found in Korea, northeast China, or far eastern Siberia. Specifically, the ginseng may be selected from panax ginseng or red ginseng, but is not limited thereto.

As used herein, the term "ginseng extract" refers to a component or substance in ginseng which is obtained from ginseng by using a solvent according to a common method.

The ginseng extract may be prepared by a preparation method including the following steps, but is not limited thereto:

1) the step of extracting ginseng by adding an extraction solvent thereto;

2) the step of cooling and filtering the extract of the step 1); and 3) the step of concentrating the extract filtered in the step 2) under reduced pressured, followed by drying.

In the above method, the ginseng of step 1) may be cultured or commercially available ginseng without limitation, and specifically, panax ginseng or red ginseng may be used, but the ginseng is not limited thereto. Further, parts of ginseng may include all organs, for example, aerial parts such as roots, branches, stems, leaves, flowers and fruits of natural, hybrid, or variant types thereof. More preferably, roots or leaves may be used, but the parts are not limited thereto.

In an embodiment of the present invention, the collected roots or leaves of ginseng (panax ginseng) were washed and dried, and then cut into pieces, which were heated in sterilized water to leach components of ginseng, thereby preparing an extract or a root extract of red ginseng.

In the above method, the extract may be extracted by using water, $C_1$ to $C_4$ alcohols, or a mixture thereof, and specifically, the alcohol may be ethanol or methanol, but is not limited thereto. More specifically, the extract may be extracted by using distilled water as the solvent.

As the extraction method, a common method in the art such as filtration, hot water extraction, immersion extraction, reflux cold extraction, and ultrasonic extraction may be used. The hot water extraction may be performed once to five times, and specifically, three times, but is not limited thereto. The extraction solvent may be added to dried ginseng 0.1- to 10-fold, and specifically, 0.3- to 5-fold, but is not limited thereto. Further, an extraction temperature may be specifically 20° C. to 40° C., but is not limited thereto, and an extraction time may be specifically 12 hours to 48 hours, but is not limited thereto.

In the above method, the concentrating under reduced pressure of step 3) may be performed by using a vacuum concentrator or a vacuum rotary evaporator, but is not limited thereto. The drying may be specifically drying under reduced pressure, vacuum drying, boiling drying, spray drying, or freeze drying, but is not limited thereto.

Meanwhile, as used herein, the term "ginsenoside" refers to a saponin in ginseng. Ginseng saponin has a specific chemical structure which is different from that of saponins found in other plants, and has unique pharmacological efficacies, and thus is also called ginsenoside, which means ginseng glycoside.

In the present invention, the ginsenoside may be purchased from a commercially available source or may be isolated from ginseng cultured or collected in nature, or the ginsenoside may be synthesized by a synthetic method, but is not limited thereto.

In the present invention, the ginsenoside may be ginsenoside Compound K or ginsenoside Rh2.

As used herein, the term "ginsenoside Compound K" refers to a saponin, which is not present in ginseng itself but is converted from saponins such as ginsenosides Rb1, Rb2, Rc, Rd, etc., which are present in ginseng or red ginseng, into a form to be absorbed in the body by the action of intestinal microorganisms such as Bifidus bacteria or soil microorganisms. Ginsenoside Compound K may be represented by the following Formula 1. In the present invention, ginsenoside Compound K may be used interchangeably with 'ginsenoside CK' or 'CK'.

[Formula 1]

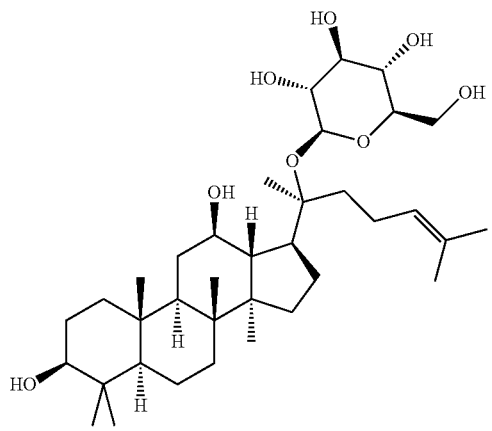

As used herein, the term "ginsenoside Rh2" refers to a PPD (protopanaxadiol)-type saponin isolated from ginseng. The ginsenoside Rh2 is also called 20(S)-protopanaxdiol-3-O-β-D-glucopyranoside, and has a chemical formula of $C_{36}H_{62}O_8$, represented by the following Formula 2. In the present invention, the ginsenoside Rh2 may be used interchangeably with 'Rh2'.

[Formula 2]

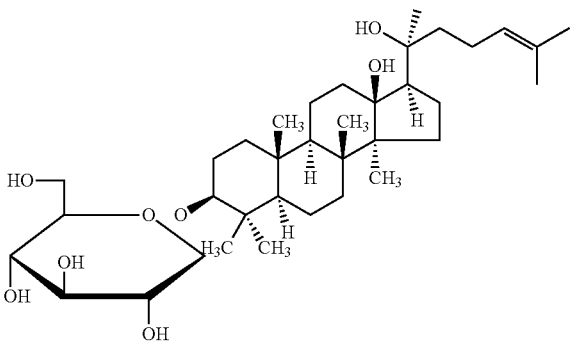

According to what has been studied so far, ginsenoside CK is known to exhibit apoptotic action on nasopharyngeal carcinoma (Law C K, Chin Med., 2014, 2, 9(1):11.), anti-allergic action (Choo M K, et al., Planta Med., 69:518-522, 2003), prophylactic action on neurodegenerative diseases (Tohda C., et al., Neuropsychopharmacology, 29:860-868, 2004), skin-protecting action (Shin Y W, et al., J. Pharmacol. Sci., 99:83-88, 2005), etc., and ginsenoside Rh2 is known to exhibit inhibitory effects on liver cancer (Xiao-Xi Guo, Int. J. Mol. Sci., 2012, 13, 15523-15535), pancreatic cancer (Xi-Ping Tang, World J Gastroenterol., 2013, 19(10), 1582-1592), osteoclast formation (He L., Bone., 2012, 50(6), 1207-13.), etc.

However, ginsenoside CK or Rh2 have low water solubility and toxicity towards cancer cells as well as normal cells, which limit its use in anticancer drugs. Therefore, in the present invention, nanocomposites were prepared to increase the water solubility of ginsenosides and to impart cancer-specific activity, thereby completing the present invention. Although ginsenoside CK or Rh2 has low water solubility and no cancer cell specificity, and the drug delivery system has no anti-cancer activities, the above disadvantages have been overcome by conjugation of the two compounds. It was also confirmed that the nanocomposites exhibit not only excellent anti-cancer activities but also excellent anti-inflammatory activities which may not be inferred from use of ginsenoside CK or Rh2 alone, thereby completing the present invention.

As used herein, the term "nanocomposite" refers to a chemical linkage of the drug delivery system; and the ginseng extract or ginsenoside isolated therefrom.

In the present invention, the nanocomposite may be nanocomposite of metal nanoparticles, BSA (Bovine serum albumin), or mesoporous silica nanoparticles with the ginseng extract or ginsenoside CK and Rh2 isolated therefrom, and for example, it may be used interchangeably with 'gold nanocomposite', 'silver nanocomposite', 'BSA-CK', 'BSA-CK nanocomposite', 'MSNP-CK', 'MSNP-CK nanocomposite', etc.

When the nano-drug delivery system is metal nanoparticles, a ginseng root or leaf extract or a red ginseng root extract which is a natural extract may be used as an active ingredient, thereby preparing nanocomposites which are uniform in size without using an additional reducing agent or stabilizing agent in a significantly shortened time, as compared with the known methods. In particular, when the leaf extract is used, nanocomposites which are uniform and small in size may be prepared, and the nanocomposites have excellent stability. Further, a composition including the nanocomposites prepared by the above method may have anti-microbial activity, biofilm-degrading activity, anti-coagulant activity, anti-cancer activity, and anti-inflammatory activity, and therefore, it may be applied to a variety of industrial fields.

As used herein, the term "metal nanoparticle" refers to an ultra-fine particle which is composed of metals and has a size of at least 1 nm to 100 nm, and exhibits unique and diverse properties due to its small size. In particular, those prepared by using the ginseng root or leaf extract or the red ginseng root extract of the present invention are "metal nanocomposites" including physiologically active substances. Therefore, the metal nanocomposites may have very excellent anti-microbial activity, biofilm-degrading activity, anti-coagulant activity, anti-cancer activity, and anti-inflammatory activity, as compared with metal nanoparticles prepared by other methods, but are not limited thereto.

Specifically, the "metal" may be one or more selected from the group consisting of gold (Au), silver (Ag), copper (Cu), palladium (Pd), platinum (Pt), and rhodium (Rd), and more specifically, gold (Au) or silver (Ag), but is not limited thereto.

In the present invention, gold nanoparticles, gold nanocomposites, and AuNP(s) may be used interchangeably with one another, and silver nanoparticles, silver nanocomposites, and AgP(s) may be used interchangeably with one another.

In an embodiment of the present invention, a reduction reaction of the ginseng root or leaf extract or the red ginseng root extract and the liquid extract with a gold(III) chloride trihydrate or silver nitrate solution was allowed, and color changes in the reaction mixture were examined with the naked eye to confirm synthesis of gold or silver nanocomposites.

Therefore, nanocomposites may be prepared by using the ginseng extract as an active ingredient, and in particular, gold or silver nanocomposites may be prepared by using the ginseng leaf or root extract or the red ginseng root extract.

In this case, the nanocomposite may be specifically 3 nm to 80 nm, more specifically 5 nm to 50 nm, and most specifically 10 nm to 40 nm in size, but is not limited thereto. Known gold nanocomposites are generally 2 nm to 40 nm in size, and known silver nanocomposites are generally 100 nm in size, whereas the gold or silver nanocomposite prepared by using the ginseng extract of the present invention is small in size and shows uniform distribution, as compared with the known metal nanoparticles. In particular, the silver nanocomposite of the present invention is very small in size, as compared with the known nanocomposites.

In a specific embodiment of the present invention, it was confirmed that the metal nanocomposites prepared by using the ginseng extracts were formed as nanocomposites having a uniform size of 10 nm to 40 nm. Specifically, the gold nanocomposite prepared by using the ginseng leaf extract was 10 nm to 30 nm in size, the gold nanocomposite prepared by using the ginseng root extract was 10 nm to 40 nm in size, and the gold nanocomposite prepared by using the red ginseng root extract was 10 nm to 30 nm in size, indicating that the gold nanoparticles were very uniform in size.

Further, the silver nanocomposite prepared by using the ginseng leaf extract was 10 nm to 20 nm in size, the silver nanocomposite prepared by using the ginseng root extract was 10 nm to 30 nm in size, and the silver nanocomposite prepared by using the red ginseng root extract was 10 nm to 30 nm in size, indicating that the silver nanoparticles were also very uniform in size.

When the nano-drug delivery system is BSA (Bovine serum albumin), "BSA (Bovine serum albumin)" refers to bovine serum albumin, which is a kind of protein contained in the plasma in a large amount of about 60%. BSA is added to be used as a nutrient for cells during cell culture, and used as a standard to obtain a calibration curve in protein quantification, or used to prevent non-specific binding in various biochemical experiments (Western blot, Immunocytochemistry, ELISA, etc.).

In this case, 0.05 mg to 0.15 mg of ginsenoside per 1 mg of the nanocomposite may be included.

In a specific embodiment of the present disclosure, the amount of ginsenoside loaded in BSA-CK or BSA-Rh2 nanocomposites was calculated by HPLC, and as a result, it was confirmed that the amount of CK loaded in 1 mg of BSA-CK was 0.087 mg, and the amount of Rh2 loaded in 1 mg of BSA-Rh2 was 0.096 mg.

Further, morphology of the BSA-CK or BSA-Rh2 nanocomposite was examined by FE-TEM, and as a result, it was confirmed that all of the nanocomposites had spherical morphology; the size of the BSA-CK or BSA-Rh2 nanocomposite was examined by dynamic light scattering (DLS), and as a result, it was confirmed that they have an average hydrodynamic size of 157.2 nm or 175.8 nm, respectively; zeta potential of the BSA-CK or BSA-Rh2 nanocomposite was measured, and as a result, it was confirmed that they have a zeta potential of −70.80 mV or −80.2 mV, respectively.

In a specific embodiment of the present invention, it was confirmed that lung cancer cell-killing ability of BSA-CK was significantly higher than that of CK alone.

When the nano-drug delivery system is mesoporous silica nanoparticles, the "mesoporous silica nanoparticle" refers to a particle in which silica has a mesoporous form and its size is 1 nm to 100 nm, and the term 'mesoporous' refers to a plurality of pores having a diameter of 2 nm to 50 nm. In the present invention, the mesoporous silica nanoparticles may be used interchangeably with 'MSNP'.

In this case, the nanocomposite may include 0.05 mg to 0.15 mg of ginsenoside per 1 mg of nanocomposite.

In a specific embodiment of the present invention, the amount of ginsenoside loaded in MSNP-CK or MSNP-Rh2 nanocomposite was calculated by HPLC, and as a result, it was confirmed that the amount of CK loaded in 1 mg of MSNP-CK was 0.087 mg, and the amount of Rh2 loaded in 1 mg of MSNP-Rh2 was 0.096 mg.

In another specific embodiment of the present invention, to characterize the MSNP-CK or MSNP-Rh2 nanocomposite, $^1$H NMR and FTIR were used to perform analysis, and as a result, it was confirmed that the nanocomposites showed a characteristic peak of ginsenoside, and morphology of the MSNP-CK or MSNP-Rh2 nanocomposite was examined by FE-TEM, and as a result, it was confirmed that all of the nanocomposites had a spherical morphology.

In a specific embodiment of the present invention, it was confirmed that lung cancer cell-killing ability of MSNP-CK was significantly higher than that of CK alone.

Another aspect of the present invention provides a pharmaceutical composition for preventing or treating cancer including the nanocomposites, and also provides a method of treating cancer including the step of administering the nanocomposites to a patient.

As used herein, the term "nanocomposite" is the same as described above.

As used herein, the term "cancer" refers to a disease which causes malignant tumors due to unlimited proliferation of cells in a biological tissue, and the cancer is not particularly limited, as long as symptoms may be alleviated, relieved, improved, or treated by the pharmaceutical composition of the present invention. A specific example may be lung cancer.

The cancer may be lung cancer, non-small cell lung cancer, colon cancer, bone cancer, pancreatic cancer, skin cancer, head or neck cancer, skin or intraocular melanoma, uterine cancer, ovarian cancer, rectal cancer, stomach cancer, anal cancer, colon cancer, breast cancer, fallopian tube carcinoma, endometrial carcinoma, cervical cancer, vaginal cancer, vulvar carcinoma, Hodgkin's disease, esophageal cancer, small bowel cancer, endocrine cancer, thyroid cancer, parathyroid carcinoma, adrenal cancer, soft tissue sarcoma, urethral cancer, penile carcinoma, prostate cancer, chronic or acute leukemia, lymphocytic lymphoma, bladder cancer, renal or ureteral cancer, renal cell carcinoma, renal pelvis carcinoma, CNS (central nervous system) tumor, primary central nervous system lymphoma, spinal cord tumor, brainstem glioma, pituitary adenoma, etc., but is not limited thereto.

As used herein, the term "prevention" refers to all of the actions by which occurrence of a disease is restrained or retarded by administration of the pharmaceutical composition including the nanocomposites of BSA and ginsenoside of the present invention as an active ingredient. In the present invention, the 'disease' may be a cancer or an inflammatory disease.

As used herein, the term "treatment" refers to all of the actions by which symptoms of a subject having or being suspected of having a disease improve or are modified favorably by administration of the pharmaceutical composition. In the present invention, the 'disease' may be a cancer or an inflammatory disease.

The pharmaceutical composition of the present invention may include the nanocomposites of BSA and ginsenoside in an amount of 0.0001% by weight to 50% by weight, specifically 0.01% by weight to 10% by weight, based on the total weight of the composition, but is not limited thereto.

The pharmaceutical composition may further include a pharmaceutically acceptable carrier, excipient, or diluent commonly used in the preparation of pharmaceutical compositions, and the carrier may include a non-naturally occurring carrier.

Specifically, the pharmaceutical composition may be formulated in oral dosage forms, including powders, granules, tablets, capsules, suspensions, emulsions, syrup, aerosol, etc., preparations for external application, suppositories, and sterile injectable solutions. In the present invention, the carriers, excipients, and diluents that may be included in the pharmaceutical composition may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil. The pharmaceutical composition of the present invention may be formulated with commonly used diluents or excipients, such as fillers, extenders, binders, wetting agents, disintegrants, surfactants, etc. Solid formulations for oral administration may include tablets, pills, powders, granules, capsules, etc., and such solid formulations may be prepared by mixing with at least one excipient, for example, starch, calcium carbonate, sucrose, lactose, gelatin, etc. In addition to simple excipients, lubricants such as magnesium stearate or talc may also be used. Liquid formulations for oral administration may include suspensions, solutions for internal use, emulsions, syrup, etc., and may include various excipients, for example, wetting agents, flavoring agents, aromatics, preservatives, etc., in addition to water and liquid paraffin, which are frequently used simple diluents. Formulations for parenteral administration may include sterilized aqueous solutions, non-aqueous solutions, suspensions, emulsions, lyophilized preparations, and suppositories. As non-aqueous solvents or suspending agents, propylene glycol, polyethylene glycol, plant oils such as olive oil, injectable esters such as ethyl oleate, etc. may be used. As a base of suppositories, witepsol, Macrogol, Tween 61, cacao butter, laurin butter, glycerogelatin, etc. may be used.

In a specific embodiment of the present invention, it was confirmed that silver or gold nanocomposites at a concentration of 100 µg/mL or 2 µg/mL showed cytotoxicity on human lung cancer (A549), respectively, indicating that the silver or gold nanocomposites biosynthesized by using the ginseng leaf extract have anti-cancer activities.

In another specific embodiment of the present invention, it was confirmed that BSA-CK or BSA-Rh2 nanocomposites showed high cytotoxicity on an A549 lung cancer cell line, and no cytotoxicity on a normal keratinocyte cell line at the same concentration, indicating that the nanocomposites of BSA and ginsenoside of the present invention exhibit cancer cell-specific cytotoxicity without cytotoxicity on normal cells, and therefore, the nanocomposites may be usefully applied to cancer treatment.

In still another specific embodiment of the present invention, it was confirmed that MSNP-CK or MSNP-Rh2 nanocomposites showed high cytotoxicity on an A549 lung cancer cell line, and no cytotoxicity on a normal keratinocyte cell line at the same concentration (FIG. 3), indicating that the nanocomposites of MSNP and ginsenoside of the present invention exhibit cancer cell-specific cytotoxicity without cytotoxicity on normal cells, and therefore, the nanocomposites may be usefully applied to cancer treatment.

As used herein, the term "administration" means introducing a predetermined material into a subject by any suitable method.

As used herein, the term "subject" means all animals of rats, mice, and livestock, including humans, which have developed or are at risk of developing a disease. A specific example may be a mammal including a human. In the present invention, the 'disease' may be a cancer or an inflammatory disease.

Specifically, the method of preventing or treating cancer of the present invention may include the step of administering to a subject a pharmaceutically effective amount of the pharmaceutical composition for preventing or treating cancer including the nanocomposites of MSNP and ginsenoside as an active ingredient.

The term 'pharmaceutically effective amount' means an amount which is sufficient to treat diseases at a reasonable benefit/risk ratio applicable to any medical treatment and does not cause any adverse effect. The effective dosage level may be readily determined by those skilled in the art, depending on factors, including the patient's sex, age, body weight, and health conditions, the kind and severity of the disease, the activity of the drug, drug sensitivity, administration method, administration time, administration route, excretion rate, the duration of treatment, drugs used in combination or used concurrently, and other factors known in the medical field.

Specifically, the composition of the present invention may be administered in a daily dosage of 0.0001 mg/kg to 100 mg/kg (body weight), and more specifically 0.001 mg/kg to 100 mg/kg (body weight), based on the solid components. The recommended dose may be administered once per day or in several divided doses per day.

In the method of preventing or treating cancer of the present invention, the administration route and administration mode of the composition are not particularly limited, and the method may be performed according to any administration route and administration mode as long as the composition reaches a desired site. Specifically, the composition may be administered via various routes including oral or parenteral routes. Non-limiting examples of the administration routes may include an oral, rectal, topical, intravenous, intraperitoneal, intramuscular, intraarterial, transdermal, or intranasal route, or inhalation.

Still another aspect of the present invention provides a pharmaceutical composition for preventing or treating an inflammatory disease including the nanocomposites, and also provides a method of treating an inflammatory disease including the step of administering the nanocomposites to a patient.

As used herein, the terms "nanocomposite", "prevention", and "treatment" are the same as described above.

As used herein, the term "inflammatory disease" refers to a disease caused by inflammation. The inflammatory disease may be, but is not particularly limited to, a disease of which symptoms may be alleviated, relieved, improved, or treated by the pharmaceutical composition of the present invention. A specific example thereof may be Crohn's disease, erythema, atopic dermatitis, rheumatoid arthritis, Hashimoto's thyroiditis, pernicious anemia, Addison's disease, type 1 diabetes, lupus, chronic fatigue syndrome, fibromyalgia, hypothyroidism and hyperthyroidism, scleroderma, Behcet's disease, inflammatory bowel disease, multiple sclerosis, myasthenia gravis, Meniere's syndrome, Guillain-Barre syndrome, Sjogren's syndrome, vitiligo, endometriosis, psoriasis, vitiligo, systemic scleroderma, or ulcerative colitis, but is not limited thereto.

The pharmaceutical composition of the present invention may include the nanocomposites in an amount of 0.0001% by weight to 50% by weight, specifically 0.01% by weight to 10% by weight, based on the total weight of the composition, but is not limited thereto.

The pharmaceutical composition may further include a pharmaceutically acceptable carrier, excipient, or diluent commonly used in the preparation of pharmaceutical compositions, and the carrier may include a non-naturally occurring carrier.

In a specific embodiment of the present invention, it was confirmed that the silver nanocomposite did not show any cytotoxicity on RAW264.7 cells until a concentration of 1,000 μM and inhibited NO production in a concentration-dependent manner (FIG. 26), and it was also confirmed that the gold nanocomposite did not show any cytotoxicity on RAW264.7 cells until a concentration of 100 μM and inhibited NO production in a concentration-dependent manner, indicating that silver and gold nanocomposites biosynthesized by using the ginseng leaf extract have anti-inflammatory activities without cytotoxicity.

In another specific embodiment of the present invention, it was confirmed that the BSA-CK or BSA-Rh2 nanocomposite did not show any significant cytotoxicity on a macrophage cell line RAW264.7 and inhibited NO production of the macrophage cell line RAW 264.7 at a low concentration, indicating that the nanocomposites of BSA and ginsenoside of the present invention selectively inhibit NO production without showing direct cytotoxicity on normal macrophages, and are thereby usefully applied to treatment of inflammatory diseases without side effects.

In still another specific embodiment of the present invention, it was confirmed that the MSNP-CK or MSNP-Rh2 nanocomposite did not show any significant cytotoxicity on a macrophage cell line RAW264.7 and inhibited NO production of the macrophage cell line RAW 264.7 at a low concentration, indicating that the nanocomposites of MSNP and ginsenoside of the present invention selectively inhibit NO production without showing direct cytotoxicity on normal macrophages, and are thereby usefully applied to treatment of inflammatory diseases without side effects.

The method of preventing or treating an inflammatory disease of the present invention may include the step of administering to a subject a pharmaceutically effective amount of the pharmaceutical composition for preventing or treating an inflammatory disease, the composition including the nanocomposites as an active ingredient. Specifically, the composition of the present invention may be administered in a daily dosage of 0.0001 mg/kg to 100 mg/kg (body weight), and more specifically 0.001 mg/kg to 100 mg/kg (body weight), based on the solid components. The recommended dose may be administered once per day or in several divided doses per day.

In the method of preventing or treating an inflammatory disease of the present invention, the administration route and administration mode of the composition are not particularly limited, and the method may be performed according to any administration route and administration mode as long as the composition reaches a desired site. Specifically, the composition may be administered via various routes including oral or parenteral routes. Non-limiting examples of the administration routes may include an oral, rectal, topical, intravenous, intraperitoneal, intramuscular, intraarterial, transdermal, or intranasal route, or inhalation.

Still another aspect of the present invention provides a food composition for improving cancer including the nanocomposites as an active ingredient.

As used herein, the term "improving" means all of the actions by which parameters associated with conditions under treatment, for example, symptoms, are at least lessened.

As used herein, the term "food" may include meats, sausages, bread, chocolate, candies, snack, confectionery, pizza, ramen, other noodles, gum, dairy products including ice cream, a variety of soups, beverages, teas, drinks, alcoholic beverages, multi-vitamin preparations, health functional foods, health foods, etc., and may include all foods in the usual sense.

The functional food, being the same term as food for special health use (FoSHU), refers to a food with high medicinal and medical effects to efficiently exhibit a bio-regulatory function in addition to a function of nutrient supply. Here, "function(al)" means controlling nutrients for the structure or functions of the human body or providing beneficial effects to health purposes, such as physiological effects. The food of the present invention may be prepared by a method commonly used in the art, and during the preparation, raw materials and ingredients commonly added in the art may be added to prepare the food. Further, the food may be prepared in any formulation without limitation, as long as it is acceptable as a food. The food composition of the present invention may be prepared in various formulations, and unlike general drugs, it has an advantage that there is no side effect that may occur when a drug is taken for a long time, because of using the food as a raw material, and the food of the present invention may be ingested as a supplement to enhance the disease-preventing or improving effects, because of excellent portability.

The health food refers to a food that has an effect of positively maintaining or improving health, as compared with general foods, and the health supplement food refers to a food to be used for health supplement. In some cases, the terms "health functional food", "health food", and "health supplement food" are used interchangeably with one another.

Specifically, the health functional food may be a food prepared by adding the nanocomposites to food materials such as beverages, teas, flavors, gum, snacks, etc., or prepared as a capsule, powder, suspension, etc. When this health functional food is ingested, it brings about a specific effect on health, and unlike other common drugs, the health functional food composition has an advantage of avoiding side effects associated with long-term administration of drugs, because of being prepared by using foods as raw materials.

Since the food composition of the present invention may be ingested routinely, high cancer-preventing or improving effects may be expected, and therefore, it is very useful.

The composition may further include a physiologically acceptable carrier. A kind of the carrier is not particularly limited, and any carrier may be used as long as it is a carrier commonly used in the art.

The composition may further include an additive which is commonly used in food compositions to enhance flavor, taste, color, etc. For example, the composition may include vitamin A, C, D, E, B1, B2, B6, or B12, niacin, biotin, folate, pantothenic acid, etc. The composition may also include minerals such as zinc (Zn), iron (Fe), calcium (Ca), chromium (Cr), magnesium (Mg), manganese (Mn), copper (Cu), chromium (Cr), etc. The composition may also include amino acids such as lysine, tryptophan, cysteine, valine, etc.

The composition may also be supplemented with food additives, including antiseptics (e.g., potassium sorbate, sodium benzoate, salicylic acid, sodium dehydroacetate, etc.), disinfecting agents (e.g., bleaching powder and high-test bleaching powder, sodium hypochlorite, etc.), antioxidants (e.g., butylhydroxyanisole (BHA), butylhydroxytoluene (BHT), etc.), colorants (e.g., tar dye, etc.), color fixing agents (e.g., sodium nitrate, sodium nitrite, etc.), bleaching agents (e.g., sodium sulfite), seasoning agents (e.g., MSG, sodium glutamate, etc.), sweeteners (e.g., dulcin, cyclamate, saccharine, sodium, etc.), flavoring agents (vanillin, lactones, etc.), blowing agents (alum, potassium D-bitartrate, etc.), fortifying agents, emulsifying agents, thickening agents, coating agents, gum bases, antifoaming agents, solvents, improving agents, etc. The additives may be selected according to food type, and they may be used in suitable amounts.

The nanocomposite of BSA and ginsenoside may be added as it is or together with other foods or food components, and appropriately used according to a common method. A mixed amount of the active ingredients may be suitably determined according to the intended use (preventive, health, or therapeutic purposes). Generally, the food composition of the present invention may be added in an amount of 50 parts by weight or less, and specifically 20 parts by weight of less with respect to a food or drink, upon preparing the food or drink. When consumed for a long period of time for health and sanitary purposes, the composition may be used in an amount below the range. Also, it is apparent that the active ingredients may be used in an amount above the range, because the active ingredient carries no safety risk.

The food composition of the present invention may be used as, for example, a health beverage composition. In this case, the health beverage composition may include various flavoring agents or natural carbohydrates, like common beverages. The above-described natural carbohydrates may include monosaccharides such as glucose and fructose; disaccharides such as maltose and sucrose; polysaccharides such as dextrin and cyclodextrin; sugar alcohols such as xylitol, sorbitol, erythritol, etc. As a sweetening agent, a natural sweetening agent such as thaumatin or stevia extract; a synthetic sweetening agent such as saccharin and aspartame, etc. may be used. A content of the natural carbohydrate is generally in a range of about 0.01 g to about 0.04 g, specifically about 0.02 g to 0.03 g per 100 mL of the composition of the present invention.

In addition, the health beverage composition may further include various nutritional supplements, vitamins, electrolytes, flavorings, coloring agents, pectic acid and salts thereof, alginic acid and salts thereof, organic acids, protective-colloidal thickeners, pH regulators, stabilizing agents, preservatives, glycerin, alcohols or carbonating agents, etc. Furthermore, the health beverage composition may include fruit flesh used for natural fruit juices, fruit juice drinks, or vegetable drinks. These components may be used alone or in a mixture thereof. A ratio of these additives may not be important, but it is generally selected in the range of 0.01 parts by weight to 0.1 parts by weight per 100 parts by weight of the composition of the present invention.

The food composition of the present invention may include the nanocomposite in many different ranges of % by weight, as long as the cancer-preventing or improving effects may be obtained. Specifically, the nanocomposite may be included in an amount of 0.00001% by weight to 100% by weight or 0.01% by weight to 80% by weight, based on the total weight of the food composition.

Still another aspect provides a food composition for improving an inflammatory disease including the nanocomposites as an active ingredient.

Since the food composition of the present invention may be ingested routinely, high inflammatory disease-preventing or improving effects may be expected, and therefore, it is very useful.

The composition may further include a physiologically acceptable carrier. A kind of the carrier is not particularly limited, and any carrier may be used as long as it is a carrier commonly used in the art.

The nanocomposites may be added as it is or together with other foods or food components, and appropriately used according to a common method. A mixed amount of the active ingredients may be suitably determined according to the intended use (preventive, health, or therapeutic purposes). Generally, the food composition of the present invention may be added in an amount of 50 parts by weight or less, and specifically 20 parts by weight of less with respect to a food or drink, upon preparing the food or drink. When consumed for a long period of time for health and sanitary purposes, the composition may be used in an amount below the range. Also, it is apparent that the active ingredients may be used in an amount above the range, because the active ingredient carries no safety risk.

The food composition of the present invention may include the nanocomposite in many different ranges of % by weight, as long as the inflammatory disease-preventing or improving effects may be obtained. Specifically, the nanocomposite may be included in an amount of 0.00001% by weight to 100% by weight or 0.01% by weight to 80% by weight, based on the total weight of the food composition.

Still another aspect provides a quasi-drug composition for preventing or improving cancer or an inflammatory disease including the nanocomposite as an active ingredient.

In the present invention, the ginsenoside may be ginsenoside Compound K or ginsenoside Rh2.

As used herein, the term "quasi-drug" refers to fibers, rubber products, or similar articles used for the purpose of treating, alleviating, handling, or preventing diseases in humans or animals; non-appliance, non-machinery or similar articles which have insignificant influences on or do not directly act upon human bodies; preparations used for the purpose of disinfection or pest control, and similar purpose thereto for the prevention of infectious diseases, and the quasi-drug refers to articles used for the purposes of diagnosis, treatment, alleviation, handling, or prevention of diseases of human beings or animals, excluding appliances, machinery, or equipment; or articles, other than appliances, machinery, or equipment, used for the purpose of exerting pharmacological effects upon the structure or functions of human beings or animals. Specifically, the quasi-drug may be a formulation for external application, but is not limited thereto.

When the nanocomposite is added to the quasi-drug composition for the purpose of preventing or improving inflammatory diseases, the nanocomposite of BSA and ginsenoside may be added as it is or together with other quasi-drug components, and appropriately used according to a common method. The mixing amount of the active ingredient may be properly determined according to the purpose of use.

The formulation for external application may be used after being prepared, for example, in a form of ointment, lotion, spray, patch, cream, powder, suspension, gel preparation, or gel, but is not particularly limited thereto.

The quasi-drug composition of the present invention may include the nanocomposite in many different ranges of % by weight, as long as the inflammatory disease-preventing or improving effects may be obtained. Specifically, the nanocomposite may be included in an amount of 0.01% by weight to 100% by weight, more specifically, 1% by weight to 80% by weight, based on the total weight of the quasi-drug composition.

Still another aspect provides a cosmetic composition for preventing or improving an inflammatory disease including the nanocomposite as an active ingredient.

The cosmetic composition of the present invention may include the nanocomposite in an amount of 0.0001% by weight to 50% by weight, specifically 0.01% by weight to 10% by weight, based on the total weight of the composition. There are advantages that within the above range, the excellent effect of preventing or improving inflammatory diseases may be obtained and the formulation of the composition may be stabilized.

The cosmetic composition may be prepared in a formulation selected from the group consisting of a solution, a topical ointment, a cream, a foam, a nourishing toner, a softening toner, a pack, a softening water, a milky liquid, a makeup base, an essence, a soap, a liquid cleanser, a bath preparation, a sunscreen cream, a sun oil, a suspension, an emulsion, a paste, a gel, a lotion, a powder, a soap, a surfactant-containing cleansing, an oil, a powder foundation, an emulsion foundation, a wax foundation, a patch, and a spray, but is not limited thereto.

The cosmetic composition of the present invention may further include one or more cosmetically acceptable carrier which is blended with the general chemical skin cosmetic composition, for example, oil, water, surfactants, humectants, lower alcohols, thickeners, chelating agents, dyes, preservatives, fragrances, but is not limited thereto.

The cosmetically acceptable carrier included in the cosmetic composition may vary depending on the formulation of the cosmetic composition.

When the formulation of the present invention is an ointment, a paste, a cream, or a gel, animal oil, vegetable oil, wax, paraffin, starch, tragacanth, a cellulose derivative, polyethylene glycol, silicon, bentonite, silica, talc, zinc oxide, etc. may be used as the carrier component, but is not limited thereto. These components may be used alone or in a mixture of two or more thereof.

When the formulation of the present invention is a powder or a spray, it may include, as the carrier component, lactose, talc, silica, aluminum hydroxide, calcium silicate, polyamide powder, etc. Particularly, when the formulation of the present invention is a spray, it may additionally include a propellant, such as chlorofluorohydrocarbon, propane/butane, or dimethyl ether, but is not limited thereto. These components may be used alone or in a mixture of two or more thereof.

When the formulation of the present invention is a solution or an emulsion, it may include, as the carrier component, a solvent, a solubilizing agent, or an emulsifying agent, and for example, water, ethanol, isopropanol, ethyl carbonate, ethyl acetate, benzyl alcohol, benzyl benzoate, propylene glycol, 1,3-butyl glycol oil, etc. may be used, and in particular, cottonseed oil, peanut oil, corn germ seed oil, olive oil, castor oil and sesame oil, glycerol fatty ester, polyethylene glycol, or sorbitan fatty acid ester may be used, but the carrier is not limited thereto. These components may be used alone or in a mixture of two or more thereof.

When the formulation of the present invention is a suspension, it may include, as the carrier component, a liquid diluent, such as water, ethanol, or propylene glycol, and a suspending agent, such as ethoxylated isostearyl alcohol, polyoxyethylene sorbitol ester, polyoxyethylene sorbitan ester, microcrystalline cellulose, aluminum metahydroxide, bentonite, agar, or tragacanth, but is not limited thereto. These components may be used alone or in a mixture of two or more thereof.

When the formulation of the present invention is a soap, it may include, as the carrier component, alkali metal salts of fatty acids, salts of fatty acid hemiesters, fatty acid protein hydrolysates, isethionate, lanolin derivatives, aliphatic alcohol, vegetable oil, glycerol, sugars, etc., but is not limited thereto. These components may be used alone or in a mixture of two or more thereof.

When the formulation of the present invention is a surfactant-containing cleansing, it may include, as the carrier component, aliphatic alcohol sulfate, aliphatic alcohol ether sulfate, sulfosuccinic monoester, isethionate, imidazolium derivatives, methyl taurate, sarcosinate, fatty acid amide ether sulfate, alkyl amido betaine, aliphatic alcohol, fatty acid glyceride, fatty acid diethanolamide, vegetable oil, lanoline derivatives, ethoxylated glycerol fatty acid ester, etc., but is not limited thereto. These components may be used alone or in a mixture of two or more thereof.

Still another aspect of the present invention provides an antimicrobial composition including the nanocomposite.

Since the nanocomposite of the present invention is prepared by using the ginseng root or leaf extract or the red ginseng root extract and includes a physiologically active material of each extract, the nanocomposite has very excellent antimicrobial activity, as compared with metal nanoparticles prepared by other methods.

The antimicrobial composition of the present invention may have antimicrobial activity against bacteria, fungi, or yeasts, and specifically, the antimicrobial composition may have antimicrobial activity against one or more selected from the group consisting of a microorganism of the genus *Vibrio*, the genus *Salmonella*, the genus *Staphylococcus*, the genus *Escherichia*, the genus *Bacillus*, and the genus *Candida*, and more specifically, the antimicrobial composition may have antimicrobial activity against one or more selected from the group consisting of *Vibrio parahaemolyticus*, *Salmonella enterica*, *Staphylococcus aureus*, *Escherichia coli*, *Bacillus anthracis*, *Bacillus cereus*, and *Candida albicans*, but is not limited thereto.

Specifically, since the silver nanocomposite or the composition including the silver nanocomposite of the present invention has very excellent antimicrobial activity against pathogenic microorganisms, as compared with general silver nanocomposites, it may be widely used in a variety of fields such as cosmetics, quasi-drugs, drugs, foods, etc.

In a specific embodiment of the present invention, it was confirmed that the gold nanocomposite using the ginseng leaf extract had antimicrobial activity against *Vibrio parahaemolyticus*, *Salmonella enterica*, *Escherichia coli*, and *Staphylococcus aureus*, and the silver nanocomposite using the ginseng root extract had antimicrobial activity against *Escherichia coli*, *Bacillus cereus*, *Staphylococcus aureus*, *Vibrio parahaemolyticus*, and *Bacillus anthracis*. It was also confirmed that the silver nanocomposite using the red ginseng root extract had antimicrobial activity against *Vibrio parahaemolyticus*, *Staphylococcus aureus*, *Bacillus cereus*, and *Candida albicans*, the highest antimicrobial activity against *Candida albicans*, and the next highest antimicrobial activity against *Vibrio parahaemolyticus*, *Staphylococcus aureus*, and *Bacillus cereus*. These results suggest that the silver nanocomposites of the present invention have antimicrobial activity against microorganisms.

Still another aspect of the present invention provides a composition for degrading biofilms including the metal nanocomposite.

Since the nanocomposite of the present invention is prepared by using the ginseng root or leaf extract or the red ginseng root extract and thus includes a physiologically active material of each extract, the nanocomposite has very excellent biofilm-degrading activity, as compared with metal nanoparticles prepared by other methods.

As used herein, the term "biofilm" refers to an aggregation of microorganisms that attach to a surface like a thin film. That is, the biofilm is produced by microorganisms, and provides habitats for the microorganisms, causing acceleration of cell proliferation.

The composition for degrading biofilms of the present invention has biofilm-degrading activity to inhibit biofilm-related infections, and thus plays a role in cost reduction or in alleviating a patient's pain. Therefore, the composition for degrading biofilms may be used in a variety of fields, specifically including industry for protecting a surface, such as plastic, metal, etc., from corrosion, dental appliance market, piping industry, etc., but is not limited thereto.

In a specific embodiment of the present invention, the biofilm-degrading activity of the present invention against *Staphylococcus aureus* and *Pseudomonas aeruginosa* was examined by a colorimetric method, and as a result, it was confirmed that the silver nanocomposite prepared using the ginseng leaf extract showed the maximum biofilm-degrading activity against *Staphylococcus aureus* and *Pseudomonas aeruginosa* at a concentration of 4 μg/mL, and the silver nanocomposite prepared using the red ginseng root extract showed the biofilm-degrading activity against *Staphylococcus aureus* and *Pseudomonas aeruginosa* at the same concentration.

Accordingly, it was confirmed that the nanocomposite prepared using the ginseng extract has biofilm-degrading activity against the strains to inhibit biofilm-related infections, and thus plays a role in cost reduction or in alleviating a patient's pain.

Still another aspect of the present invention provides an anticoagulant composition including the nanocomposite.

Since the metal nanocomposite of the present invention is prepared by using the ginseng root or leaf extract or the red ginseng root extract and thus includes a physiologically active material of each extract, the nanocomposite has very excellent anticoagulant activity, as compared with metal nanoparticles prepared by other methods.

As used herein, the term "anticoagulant" refers to inhibition of normal blood coagulation in the body, and is also called "anti-blood clotting". Specifically, there are anticoagulant agents which are added to the blood to inhibit coagulation, antithrombin III or heparin, which are physiological anticoagulins of blood against active blood coagulation factors present in the blood and inhibit actions of various blood coagulation factors, and anticoagulant drugs which inhibit activities of coagulation factors by oral administration, and anticoagulants which are acquired under pathological conditions to reversibly and irreversibly inhibit the activities of blood coagulation factors.

Since the anticoagulant composition of the present invention includes the nanocomposite prepared using the ginseng extract, specifically, the ginseng leaf or root extract or the red ginseng root extract, thereby inhibiting blood coagulation, it may be specifically used in the medical field or biotechnology, and more specifically, used after being modified as a drug or gene carrier that is in direct contact with blood, a biosensor, or an in vivo nanocarrier, but is not limited thereto. Further, it may also be used for the purpose of in vitro experiments.

In the present invention, the anticoagulant composition may be used as a pharmaceutical, quasi-drug, cosmetic, food, or feed composition.

In a specific embodiment of the present invention, blood was collected from each of healthy male and female volunteers aged between 25 and 45, and put in two evacuated blood collection tubes, which were marked as A and B, and then anticoagulant effects of the synthesized gold nanocomposite were examined. As a result, in the presence of the gold nanocomposite prepared using the ginseng leaf extract, coagulation was inhibited, whereas in the control group without the gold nanocomposite, complete blood coagulation was observed, indicating that the gold nanocomposite biosynthesized by using the ginseng leaf extract have the anticoagulant activity.

Still another aspect of the present invention provides a method of preparing the nanocomposites including the step of mixing and reacting the nano-drug delivery system; and the ginseng extract or the ginsenoside isolated therefrom.

In the method of preparing the nanocomposites, when the drug delivery system is metal nanoparticles, the nanocomposites may be prepared by using the ginseng extract which is a natural extract. Therefore, it is possible to prepare the metal nanocomposites in an eco-friendly way and a significantly shortened time, as compared with chemical and physical synthetic methods, while maintaining its stability without using an additional reducing agent or stabilizing agent. Accordingly, the nanocomposites may be very usefully applied to a variety of industrial fields.

The preparation method of the present invention may be used to prepare many different metal nanoparticles depending on metal precursors to be used, and specifically, one or more selected from the group consisting of gold (Au), silver (Ag), copper (Cu), palladium (Pd), platinum (Pt), and rhodium (Rd), but is not limited thereto. More specifically, gold (Au) or silver (Ag) may be selected.

As used herein, the term "metal precursor" refers to a compound that is added to prepare metal nanoparticles. Specifically, the metal precursor may be selected from many different kinds of compounds according to the kind of metal of nanoparticles to be prepared. For example, in the preparation of gold nanoparticles, one or more selected from the group consisting of gold(III) chloride trihydrate ($HAuCl_4$), $NaAuCl_3$, and $AuCl_3$ may be used. More specifically, gold (III) chloride trihydrate ($HAuCl_4$) may be used, but the metal precursor is not limited thereto.

Further, in the preparation of silver nanoparticles, one or more selected from the group consisting of $AgBF_4$, $AgCF_3SO_3$, $AgClO_4$, $AgNO_3$, $AgPF_6$, and $Ag(CF_3COO)$ may be used. More specifically, silver nitrate ($AgNO_3$) may be used, but the silver nanoparticle is not limited thereto.

Further, in the preparation of copper nanoparticles, one or more selected from the group consisting of $CuCl_2$, $CuF_2$, $CuBr_2$, $CuI_2$, $(CH_3COO)_2Cu$, $Cu(ClO_4)_2$, $Cu(NO_3)_2$ and $CuSO_4$ may be used, but the copper nanoparticles are not limited thereto.

In the preparation method of the present invention, a concentration of the metal precursor used in the reaction may influence the preparation of metal nanoparticles. The concentration of the metal precursor of the present invention is not limited, as long as the metal nanoparticles may be prepared by using the composition for preparing the metal nanoparticles. The concentration of the metal precursor may be specifically 0.01 mM to 100 mM, more specifically 0.01 mM to 50 mM, and most specifically 0.01 mM to 10 mM.

In the preparation method of the present invention, a reaction temperature may influence the preparation of metal nanoparticles. The reaction temperature of the present invention is not limited, as long as the metal nanoparticles may be prepared by using the composition for preparing the metal nanoparticles. The reaction temperature may be specifically 10° C. to 100° C., and more specifically 50° C. to 100° C.

In the preparation method of the present invention, a reaction time may influence the preparation of metal nanoparticles. The reaction time of the present invention is not limited, as long as the metal nanoparticles may be prepared by using the composition for preparing the metal nanoparticles. The reaction time may be specifically 1 minute to 1 hour, and more specifically 1 minute to 50 minutes when the metal is gold, and specifically 30 minutes to 5 hours, and more specifically 30 minutes to 2 hours when the metal is silver.

In a specific embodiment of the present invention, when the ginseng (panax ginseng) leaf extract was used to prepare gold or silver nanoparticles, a reaction mixture to which gold(III) chloride trihydrate was added turned dark purple within 3 minutes (FIG. 1A), and a reaction mixture to which silver nitrate was added completely turned brown within 45 minutes (FIG. 1B). Further, when the ginseng (panax ginseng) root extract was used, a color change from white to brown in a reaction mixture to which silver nitrate was added took 2 hours (FIG. 1D), and a color change in a reaction mixture to which tetrachloroauric(III) acid was added took 5 minutes (FIG. 1E). Further, when the red ginseng root extract was used, reaction mixtures in the preparation of silver nanoparticles and gold nanoparticles turned brown and ruby red within 1 hour and 10 minutes, respectively (FIGS. 1F and 1G).

These results indicate that the gold or silver nanoparticles prepared by using the ginseng leaf or root extract or the red ginseng root extract may be synthesized within a very short time, as compared with nanoparticles prepared by using other natural extracts or extracts of other parts of ginseng. In particular, it can be seen that when the ginseng leaf extract is used, stable metal nanoparticles may be synthesized in a quick, economical, and eco-friendly manner.

When the drug delivery system is the metal nanoparticle, the preparation method of the present invention may further include the step of recovering the metal nanoparticles by centrifuging the reaction mixture.

In a specific embodiment of the present invention, the composition for preparing the metal nanoparticles including the ginseng extract was added to 1 mM gold(III) chloride trihydrate and silver nitrate solutions, respectively and the mixture was maintained at 80° C., and centrifuged at 16,000 rpm for 20 minutes to prepare metal nanoparticles (Example 3).

Still another aspect of the present invention provides the metal nanoparticles prepared by the above preparation method.

Since the metal nanocomposite of the present invention is prepared by using the ginseng root or leaf extract or the red ginseng root extract and thus includes a physiologically active material of each extract, the nanocomposite has very excellent anticoagulant activity, biofilm-degrading activity, anticoagulant activity, anti-cancer activities, and anti-inflammatory activity, as compared with metal nanoparticles prepared by other methods. Therefore, the nanocomposite may be usefully applied to a variety of fields.

The metal nanoparticles of the present invention may be used for medical applications, biological analysis, fuels, electronic component materials, and specifically, the gold nanoparticles may be used in organic solar cells, sensor probes, biological drug delivery, conductive materials, and catalyst materials due to their intrinsic light transmission property, and the silver nanoparticles may be used in antimicrobial agents, biosensors for quantitative detection, spectroscopic analysis, etc. due to their optical, conductive, and antimicrobial properties. Further, optical and electronic properties of the metal nanoparticles are tunable by changing the size, shape, surface chemistry, or aggregation state.

The shape of the metal nanoparticles prepared by the preparation method of the present invention may generally have a spherical shape, but is not limited thereto.

Further, the size of the metal nanoparticles prepared by the preparation method of the present invention may be specifically 3 nm to 80 nm, more specifically 5 nm to 50 nm, and most specifically 10 nm to 40 nm, but is not limited thereto. As compared with known gold nanoparticles and silver nanoparticles which are reported to generally have a size of 2 nm to 40 nm and a size of 100 nm, respectively, the size of the gold or silver nanoparticles prepared by using the ginseng extract of the present invention is smaller than those of the known metal nanoparticles and the size distribution is uniform, and in particular, the size of the silver nanoparticles of the present invention is much smaller than that of the known metal nanoparticles.

In a specific embodiment of the present invention, it was confirmed that the metal nanoparticles prepared by using the ginseng extract had a uniform size ranging from 10 nm to 40 nm (Example 3). Specifically, the gold nanoparticles had a size of 10 nm to 30 nm when prepared by using the ginseng leaf extract, a size of 10 nm to 40 nm when prepared by using the ginseng root extract, and a size of 10 nm to 30 nm when prepared by using the red ginseng root extract, indicating that the gold nanoparticles are very uniform in size.

Further, the silver nanoparticles had a size of 10 nm to 20 nm when prepared by using the ginseng leaf extract, a size of 10 nm to 30 nm when prepared by using the ginseng root extract, and a size of 10 nm to 30 nm when prepared by using the red ginseng root extract, indicating that the silver nanoparticles are also very uniform in size.

In the method of preparing the nanocomposites, when the drug delivery system is BSA (Bovine serum albumin), the nanocomposites may be specifically prepared by the steps of (a) dissolving BSA (Bovine serum albumin) in water to prepare a mixture; (b) adding ginsenoside to the mixture to prepare a reaction mixture; and (c) performing dialysis of the reaction mixture.

Step (a) is to prepare a BSA aqueous solution by which BSA is allowed to react with ginsenoside, and this step is a process to improve reactivity of BSA. Further, the BSA aqueous solution may be further treated, specifically, sonicated, but is not limited thereto.

Step (b) is to conjugate BSA with ginsenoside, and this step may be performed by adding ginsenoside to the BSA aqueous solution prepared in step (a). Specifically, the ginsenoside may be in a state where ginsenoside is dissolved in a solvent, and a kind of the solvent may be specifically a polar solvent such as water, $C_1$ to $C_4$ alcohols, ethyl acetate, or acetone, etc., a non-polar solvent such as hexane or dichloromethane, and more specifically ethanol, but is not limited thereto. Further, the ginsenoside may be added dropwise to the BSA aqueous solution, but is not limited thereto.

Step (c) is to purify the prepared nanocomposites of BSA and ginsenoside, and this step is a process to remove unreacted materials or impurities. This step may be performed by using a dialysis membrane or a solvent, but is not limited thereto.

In a specific embodiment of the present invention, the BSA aqueous solution was sonicated, and then added dropwise to ginsenoside CK or Rh2 dissolved in ethanol. This reaction mixture was transferred to a dialysis membrane, and then an additional dialysis process was performed by using methanol/distilled water and distilled water to prepare the nanocomposites of BSA and ginsenoside.

In the method of preparing the nanocomposites, when the drug delivery system is mesoporous silica nanoparticles, the nanocomposite may be specifically prepared by steps of (a) functionalizing the mesoporous silica nanoparticles with free amine group; and (b) conjugating ginsenoside to the functionalized mesoporous silica nanoparticles.

Step (a) is to modify MSNP for efficient conjugation of MSNP and ginsenoside, and this step is a process to conjugate amine groups on the surface of MSNP. In particular, the amination may be induced by using $NH_4OH$, but is not limited thereto.

Step (b) is to conjugate MSNP with ginsenoside, and this step is a process to react the amine group of MSNP with ginsenoside to form a covalent bond. The ginsenoside may be in a state where ginsenoside is dissolved in a solvent, and a kind of the solvent may be specifically a polar solvent such as water, $C_1$ to $C_4$ alcohols, ethyl acetate, or acetone, etc., a non-polar solvent such as hexane or dichloromethane, and more specifically ethanol, but is not limited thereto.

In a specific embodiment of the present invention, MSNP was functionalized with free amine groups by using $NH_4OH$, and ginsenoside was added to the MSNP, followed by stirring, and as a result, the nanocomposites of MSNP and ginsenoside were prepared.

Hereinafter, the present invention will be described in more detail with reference to Examples. However, these Examples are for illustrative purposes only, and the scope of the present invention is not intended to be limited by these Examples.

PREPARATION EXAMPLE 1

Preparation of Metal-Ginseng Extract Nanocomposite

PREPARATION EXAMPLE 1-1

Materials

Gold(III) chloride trihydrate ($HAuCl_4 \cdot 3H_2O$) and silver nitrate ($AgNO_3$) were purchased from Sigma-Aldrich Chemicals (USA), and all media were purchased from Difco (MB cell, Seoul, Republic of Korea). Further, roots and leaves of ginseng were collected from 4-year-old ginseng in Gochang, Republic of Korea.

30 μg/disk of vancomycin (VA30), 5 μg/disk of rifampicin (RD5), 15 μg/disk of oleandomycin (OL15), 10 μg/disk of penicillin G (P10), 30 μg/disk of novobiocin (NV30), 15 μg/disk of lincomycin (MY15), and 30 μg/disk of tetracycline (TE30), which are commercially available standard antibiotic disks, were purchased (Oxoid Ltd., England).

Pathogenic bacterial strains were selected from the group consisting of *Vibrio parahaemolyticus* [ATCC 33844], *Salmonella enteric* [ATCC 13076], *Escherichia coli* [ATCC 10798], *Staphylococcus aureus* [ATCC 6538], *Bacillus anthraces* [NCTC 10340], *Bacillus cereus* [ATCC 14579], *Candida albicans* [KACC 30062], and *Pseudomonas aeruginosa* [ATCC 27853]. These bacterial strains were cultured on nutrient agar media at 37° C. and preserved at −0° C. in glycerol stock vials.

In addition, human blood was collected from healthy male and female volunteers and stored in evacuated blood collection tubes (Greiner Bio-One).

PREPARATION EXAMPLE 1-2

Preparation of Ginseng Extract

PREPARATION EXAMPLE 1-2-1

Preparation of Ginseng Leaf Extract 15 g of the ginseng leaf collected in Preparation Example 1-1 was cleaned and then washed with distilled water several times to remove dust or dirty materials, and dried in the shade at room temperature for 6 hours to 8 hours. Thereafter, the leaves were cut into small pieces and ground with mortar and pestle. Next, the pieces were heated in 100 mL of sterile water for 20 minutes so that ginseng components leached out into the water. The liquid extract was filtered using a Whatman filter paper and centrifuged at 10,000 rpm for 15 minutes. The filtrate was stored in 100 mL of sterile water at 4° C.

PREPARATION EXAMPLE 1-2-2

Preparation of Ginseng Root Extract 25 g of the ginseng root collected in Preparation Example 1-1 was cleaned and then washed with distilled water several times to remove dust or dirty materials. Thereafter, the roots were cut into small pieces and ground with mortar and pestle. Next, the pieces were heated in 100 mL of sterile water for 30 minutes so that ginseng components leached out into the water. The liquid extract was filtered using a Whatman filter paper and centrifuged at 10,000 rpm for 10 minutes. The filtrate was stored in 100 mL of sterile water at 4° C.

PREPARATION EXAMPLE 1-2-3

Preparation of Red Ginseng Root Extract

Red ginseng roots were ground to obtain red ginseng root powder. Then, 10 g of the root powder was mixed with 100 mL of sterile water and heated for 30 minutes so that red ginseng components leached out into the water. The liquid was filtered using a Whatman filter paper and centrifuged at 10,000 rpm for 10 minutes. The filtrate was stored in 100 mL of sterile water at 4° C.

PREPARATION EXAMPLE 1-3

Synthesis of Gold or Silver Nanocomposites

PREPARATION EXAMPLE 1-3-1

Synthesis of Gold or Silver Nanocomposites Using Ginseng Leaf Extract

From 100 mL of the ginseng leaf filtrate prepared in Preparation Example 1-2-1, 5 mL of the filtrate was taken and mixed with 25 mL of sterile water. To this reaction mixture, gold(III) chloride trihydrate and silver nitrate solutions were each added to a final concentration of 1 mM. The reaction mixtures were then kept at 80° C. for reduction of $Au^{3+}$ to $Au^0$ and $Ag^+$ to $Ag^0$. The change in color was observed continuously, which indicated the formation of nanoparticles. Each of the reaction mixtures was centrifuged at 2,000 rpm for 10 minutes to remove any other unwanted components, and centrifuged at 16,000 rpm for 15 minutes to prepare a pellet, which was washed several times with sterile water. Then, the pellet was air-dried overnight. Here, the color change of the reaction mixture was observed with the naked eye to confirm synthesis of gold or silver nanocomposites (AuNP, AgNP).

As confirmed in FIGS. 1A to 1C, the reaction mixture to which gold(III) chloride trihydrate was added turned dark purple within 3 minutes (FIG. 1A), and the reaction mixture to which silver nitrate was added completely turned brown within 45 minutes (FIG. 1B). In contrast, no color change was observed in a control group in which the ginseng leaf extract and sterile water were present at the same ratio under similar conditions to the above reaction mixtures (FIG. 1C). The color change is attributed to surface plasmon, which is generated by formation of gold or silver nanocomposites in the reaction mixture.

That is, these results indicate that the gold or silver nanocomposites prepared by using the ginseng leaf extract may be synthesized within a very short time, as compared with nanocomposites prepared by using other natural extracts or extracts of other parts of ginseng. Thus, it can be seen that when the ginseng leaf extract is used, stable metal nanocomposites may be synthesized in an economical and eco-friendly manner within a very short time, and phenolic acids, flavonoids, ginsenosides, and polysaccharides present in the ginseng leaf may indirectly influence formation of the metal nanocomposites.

PREPARATION EXAMPLE 1-3-2

Synthesis of Gold and Silver Nanocomposites Using Ginseng Root Extract

From 100 mL of the ginseng root filtrate prepared in Preparation Example 1-2-2, 5 mL of the filtrate was taken and mixed with 25 mL of sterile water. To this reaction mixture, gold(III) chloride trihydrate and silver nitrate solutions were each added to a final concentration of 1 mM. The reaction mixtures were then kept at 80° C. Each of the reaction mixtures was centrifuged at 2,000 rpm for 10 minutes to remove any other unwanted components, and centrifuged at 16,000 rpm for 20 minutes to prepare a pellet, which was washed several times with sterile water. Then, the pellet was air-dried overnight. Here, the color changes of the reaction mixtures were observed with the naked eye to confirm synthesis of gold and silver nanocomposites.

As confirmed in FIGS. 1D and 1E, the color change from white to brown in the reaction mixture to which silver nitrate was added took 2 hours, and the reaction mixture to which gold(III) chloride trihydrate was added completely turned pink after 5 minutes. In contrast, no color change was observed in a control group. The color change is also attributed to surface plasmon, which is generated by formation of gold or silver nanocomposites in the reaction mixtures. Accordingly, it was confirmed that the time taken for the synthesis of these gold or silver nanocomposites was slow, as compared with the time taken for synthesis using the ginseng leaf extract, but the gold or silver nanocomposites may be synthesized in a short time, as compared with gold or silver nanocomposites prepared by using other natural extracts.

PREPARATION EXAMPLE 1-3-3

Synthesis of Gold and Silver Nanocomposites Using Red Ginseng Root Extract

From 100 mL of the red ginseng root filtrate prepared in Preparation Example 1-2-3, 5 mL of the filtrate was taken and mixed with 25 mL of sterile water. To this reaction mixture, gold(III) chloride trihydrate and silver nitrate solutions were each added to a final concentration of 1 mM. The reaction mixtures were then kept at 80° C. to allow a reduction reaction. Each of the reaction mixtures was centrifuged at 2,000 rpm for 10 minutes to remove any other unwanted components, and centrifuged at 16,000 rpm for 15 minutes to prepare a pellet, which was washed several times with sterile water. Then, the pellet was air-dried overnight. Here, the color changes of the reaction mixtures were observed with the naked eye to confirm synthesis of gold and silver nanocomposites.

As confirmed in FIGS. 1F to 1G, the reaction mixtures turned brown and ruby red within 1 hour and 10 minutes, respectively. Accordingly, it was confirmed that the time taken for the synthesis of the gold or silver nanocomposites by using the red ginseng root extract was slow, as compared with the time taken for synthesis using the ginseng leaf extract, but the gold or silver nanocomposites may be synthesized within a remarkably short time, as compared with metal nanocomposites prepared by using other natural extracts.

EXAMPLE 1

Characterization of Metal Nanocomposite Prepared by Using Ginseng Extract

EXAMPLE 1-1

Analytical Method

The size, shape, composition, and characteristics of the nanocomposites prepared by using the ginseng extract were analyzed by ultraviolet/visible spectroscopy (UV-vis), field-emission transmission electron microscopy (FE-TEM), energy dispersive X-ray analysis (EDX spectra), elemental mapping, dynamic light scattering (DLS), and stability analysis.

Specifically, to verify the reduction of silver and gold ions, absorbance of each solution was scanned in the range of 300 nm to 800 nm in a UV-vis spectrophotometer (Ultrospec 2100 Pro, Amersham Biosciences). Further, the size, shape, morphology, and distribution of the prepared nanocomposites were analyzed using field emission transmission electron microscopy (FE-TEM), energy dispersive X-ray spectroscopy (EDAX), and elemental mapping with a JEM-2100F (JEOL) instrument operated at 200 kV.

For FM-TEM, EDAX, and elemental mapping, the sample was prepared by placing a drop of the purified nanocomposites on a carbon-coated copper grid and subsequently drying in an oven at 60° C. Structural characteristics of the nanocomposites were analyzed by FE-TEM of the prepared sample, and distribution of elements was analyzed by EDX and elemental mapping.

Further, the size distribution profile of the nanocomposites was analyzed using dynamic light scattering (DLS), a particle size analyzer (Photal, Otsuka Electronics, Japan). Specifically, the hydrodynamic diameters and polydispersity index (PDI) were analyzed at 25° C. As a reference dispersive medium, pure water with a refractive index of 1.3328, viscosity of 0.8878, and dielectric constant of 78.3 was used.

The X-ray diffraction (XRD) analyses of the prepared nanocomposites were performed on X-ray diffractometer (D8 Advance, Bruker, Germany) operated at 40 kV, 40 mA with CuKα radiation, at a scanning rate of 6°/min, step size of 0.02, over the 2θ range of 20° to 80°.

Further, stability of the nanocomposites was observed before and after the addition of sodium hydroxide to the nanocomposites. The effect of the change in pH on the stability of the nanocomposites was studied over the pH range of 3 to 12.

EXAMPLE 1-2

Results of Characterization of Gold or Silver Nanocomposites Prepared by Using Ginseng Extract

EXAMPLE 1-2-1

Ultraviolet/Visible Spectroscopy (UV-Vis)

Preparation of gold or silver nanocomposites using the ginseng leaf and root extracts and the red ginseng root extract prepared in Preparation Examples 1-3-1 to 1-3-3 was analyzed by UV-vis spectroscopy, and as a result, when the ginseng leaf extract was used, the gold nanocomposites and the silver nanocomposites showed a main absorption peak at 578 nm and 420 nm, respectively, indicating that the gold or silver nanocomposites were prepared by using the ginseng leaf extract (FIGS. 2A and 2B). Further, when the ginseng root extract was used, the silver nanocomposites and the gold nanocomposites showed a main absorption peak at 412 nm and 534 nm, respectively, also indicating that the gold and silver nanocomposites were prepared by using the ginseng root extract (FIGS. 3A and 3B).

Lastly, when the red ginseng root extract was used, the silver nanocomposites and the gold nanocomposites showed a main absorption peak at 410 nm and 560 nm, respectively, also indicating that the gold and silver nanocomposites were prepared by using the red ginseng root extract (FIGS. 4A and 4B).

Such main absorption peaks are the characteristic peaks of gold or silver nanocomposites, corresponding to surface plasmon resonance of nanocomposites. Although the gold or silver nanocomposites prepared by using the ginseng leaf or root extract or the red ginseng root extract were stored at 20° C., no apparent difference was observed in the UV-vis spectrum even after several months, indicating stability of the metal nanocomposites in water for a long period of time.

EXAMPLE 1-2-2

Field-Emission Transmission Electron Microscopy (FE-TEM)

Structural characteristics of the gold or silver nanocomposites prepared by using the ginseng leaf or root extract or the red ginseng root extract prepared in Preparation Examples 1-3-1 to 1-3-3 were analyzed by FE-TEM.

As a result, the gold nanocomposite prepared by using the ginseng leaf extract had a size of 10 nm to 30 nm and a spherical shape (FIGS. 5A and 5B), and a fringe spacing of 0.23 nm (FIG. 5C). Further, FIG. 5D shows selected electron diffraction pattern (SEAD) of the purified spherical gold nanocomposite having rings corresponding to [111], [200], [220], [311], and [222] (FIG. 5D). The silver nanocomposite had a size of 10 nm to 20 nm and a spherical shape (FIGS. 5E and F), and a fringe spacing of 0.24 nm (FIG. 5G). Further, SEAD image of the silver nanocomposite having rings corresponding to [111], [200], [220], [311], and [222] was confirmed (FIG. 5H).

The silver nanocomposite prepared by using the ginseng root extract had a size of 10 nm to 30 nm and a spherical shape (FIGS. 6A and 6B), and the gold nanocomposite prepared thereby had a size of 10 nm to 40 nm and a spherical shape (FIGS. 6C and 6D). Further, the silver and gold nanocomposites were uniform and monodisperse (FIG. 7A), and had a fringe spacing of 0.23 nm (FIGS. 7B and 7C). Ring-like diffraction patterns showing that particles are crystalline were confirmed in SEAD image of silver and gold nanocomposites corresponding to [111], [200], [220], and [311] (FIGS. 7D to 7F).

It was confirmed that all of the gold and silver nanocomposites prepared by using the red ginseng root extract had a size of 10 nm to 30 nm and a spherical shape and were uniform and monodisperse (FIGS. 8A and 8B).

These results further confirmed that the gold and silver nanocomposites were prepared by the ginseng leaf or root extract or the red ginseng root extract. Further, it was confirmed that the size of the prepared gold and silver nanocomposites was uniform in the distribution and small, as compared with the known metal nanocomposites, and in particular, the size of the silver nanocomposite was remarkably reduced, as compared with the known size of 100 nm.

EXAMPLE 1-2-3

Enemy Dispersive X-Ray Analysis (EDAX)

Purities of the gold and silver nanocomposites prepared in Preparation Example 1-3 were measured by EDAX analysis, respectively.

As a result, with regard to the gold or silver nanocomposites prepared by using the ginseng leaf extract, as confirmed in FIGS. 9A and 9B, the optical absorbance of gold nanocomposites was observed at 2.15 keV, and the optical absorbance of silver nanocomposites was observed at 3 keV (FIGS. 9A and 9B). With regard to the nanocomposites prepared by using the ginseng root extract, the optical absorbance of silver nanocomposites was observed at 3 keV, and the optical absorbance of gold nanocomposites was observed at 2.2 keV (FIGS. 10A and 10B). Further, with regard to the nanocomposites prepared by using the red ginseng root extract, the optical absorbance of silver nanocomposites was observed at 3 keV, and the optical absorbance of gold nanocomposites was observed at 2.3 keV (FIGS. 11A and 11B). These results indicate that due to gold and silver nanocrystalline nature, gold and silver nanocomposites were prepared.

EXAMPLE 1-2-4

Transmission Electron Microscopy (TEM)

Distributions of the gold and silver nanocomposites prepared in Preparation Example 1-3 were analyzed by TEM, and results of the elemental mapping were confirmed through electron microscopy of the synthesized nanocomposite pellet solution.

As a result, it was confirmed that distributions of the gold and silver nanocomposites prepared by using the ginseng leaf extract were 54.73% (FIGS. 12A and 12B) and 47.70% (FIGS. 12C and 12D), respectively. It was confirmed that distributions of the silver and gold nanocomposites prepared by using the ginseng root extract were 54.73% (FIGS. 13C and 13D) and 52.16% (FIGS. 13C and 13D), respectively. The elemental mapping results of the nanocomposites prepared by using the red ginseng root extract were confirmed through FIGS. 14A to 14D. The above results obtained from elemental mapping indicate that the gold and silver nanocomposites of the present invention are excellent particles in respective materials.

EXAMPLE 1-2-5

X-Ray Diffraction Analysis (XRD)

Diffraction patterns of the gold and silver nanocomposites prepared in Preparation Example 1-3 were analyzed by XRD analysis.

As a result, the gold nanocomposites prepared by using the ginseng leaf extract showed an intense peak in the entire spectrum of 2θ values ranging from 20° to 80° corresponding to [111], [200], [220], [311], and [222], and the XRD spectrum of the silver nanocomposites showed a peak in 2θ values corresponding to [111], [200], [331], [241], and [311] (FIGS. 15A and 15B). In the case of using the ginseng root extract, an intense peak was observed in the entire spectrum of 2θ values corresponding to [111], [200], [331], [241], and [311] (FIGS. 16A and 16B), indicating the values similar to Bragg's reflection of the gold and silver nanocrystals. Accordingly, from these results, it was confirmed that the gold and silver nanocomposites were prepared.

EXAMPLE 1-2-6

Dynamic Light Scattering Analysis (DLS)

Particle size distribution profiles based on volume, number, and intensity of the gold and silver nanocomposites prepared in Preparation Example 1-3 were confirmed through the dynamic light scattering analysis.

As a result, the size of the gold nanocomposite prepared by using the ginseng leaf extract was in the range of 50 nm to 150 nm with a polydispersity index (PDI) of 0.191 (FIGS. 17A to 17C), and the size of the silver nanocomposite prepared thereby was in the range of 70 nm to 140 nm with a polydispersity index (PDI) of 0.13 (FIGS. 17D to 17F), and the average particle sizes of the gold and silver nanocomposites, that is, hydrodynamic diameters of the nanocomposites, were 97 nm and 80 nm, respectively. Further, the average diameter of the silver nanocomposite prepared by using the red ginseng root extract was 83 nm with a polydispersity index (PDI) of 0.190 (FIGS. 18A to 18C), and the average diameter of the gold nanocomposite prepared thereby was 183 nm with a polydispersity index (PDI) of 0.159 (FIGS. 18D to 18F).

EXAMPLE 1-2-7

Stability Test

Lastly, for stability test of the gold and silver nanocomposites prepared in Preparation Example 1-3, 0.1 M sodium hydroxide was added to reaction mixtures for the synthesis of nanocomposites at pH 5.6 and pH 6, respectively.

As a result, the gold or silver nanocomposites prepared by using the ginseng leaf or root extract showed no major shift, even though sodium hydroxide was added, indicating that they are stable. In particular, there was no major shift in absorbance at pH 3 to pH 12. Further, UV-vis spectra of the reaction mixtures were examined at 3 weeks after synthesis, and as a result, no changes were observed. Further, when the gold or silver nanocomposites were synthesized by using the red ginseng root extract, no major shift was observed in the above pH range, indicating that they are stable. Further, UV-vis spectra of the reaction mixtures were examined at 3 weeks after synthesis, and as a result, no changes were observed.

These results indicate that the gold and silver nanocomposites synthesized by using the ginseng leaf or root extract or the red ginseng extract have stability even without an additional reducing agent or stabilizing agent. In particular, the results indicate that components such as phenolic acids and flavonoids having antioxidant activity and ginsenosides such as Rb1, Rb2, Rc, Rd, Re, Rg1, F1, F2, and F4 present in the ginseng leaf play an important role in the stability of the gold and silver nanocomposites synthesized by using the ginseng leaf extract, and accordingly, the ginseng leaf extract as it is may function as a reducing agent and a stabilizing agent without other reducing agents and stabilizing agents, and the gold and silver nanocomposites prepared by using the ginseng leaf extract of the present invention may be applied to drug delivery systems in a wide range of pH.

EXAMPLE 2

Test of Antimicrobial Activity of Nanocomposites

EXAMPLE 2-1

Measurement Method

Antimicrobial activities of nanocomposites was measured on Muller-Hinton agar (MHA) plates using a disk diffusion method. Pathogenic microorganisms used in the antimicrobial activity test were selected from the group consisting of *Vibrio parahaemolyticus*, *Salmonella enterica*, *Staphylococcus aureus*, *Escherichia coli*, *Bacillus anthraces*, *Bacillus cereus*, and *Candida albicans*.

100 μL of each of the strains was spread evenly on the MHA medium plates, and incubated overnight. 30 μL (100 mg/L) or 50 μL (100 mg/L) of the prepared silver or gold nanocomposite reaction mixture was applied and incubated at 37° C. for 24 hours. After incubation, the inhibition zones around silver and gold nanocomposites were measured, and compared with the inhibition zone of each antibiotic disk. As a control group, one or more standard antibiotics selected from the group consisting of vancomycin, novobiocin, tetracycline, rifampicin, oleandomycin, penicillin, and lincomycin were used.

EXAMPLE 2-2

Results of Antimicrobial Activity Test

As confirmed in FIG. 19, the gold nanocomposite prepared by using the ginseng leaf extract prepared in Preparation Example 1-3-1 had an antimicrobial activity against *Vibrio parahaemolyticus*, *Salmonella enterica*, *Escherichia coli*, and *Staphylococcus aureus*, and the silver nanocomposite prepared thereby had an antimicrobial activity against *Vibrio parahaemolyticus*, *Salmonella enterica*, and *Escherichia coli*. These results are shown in the following Table 1.

TABLE 1

| Strain name | Zone of inhibition | | | | |
|---|---|---|---|---|---|
| | AgNPs | AuNPs | Tetracyclin | Vancomycin | Novobiocin |
| E. coli | 14 ± 0.7 | — | 20 ± 0.1 | — | — |
| S. enterica | 15 ± 0.5 | — | 30 ± 0.3 | — | — |
| V. parahaemolyticus | 14 ± 1 | — | 25 ± 0.6 | — | — |
| S. aureus | 16 ± 1.2 | — | — | — | — |

Further, the antimicrobial activities of the gold and silver nanocomposites prepared by using the ginseng root extract prepared in Preparation Example 1-3-2 were measured, and as a result, as confirmed in FIG. 20, the silver nanocomposite showed an antimicrobial activity against *Escherichia coli*, *Bacillus cereus*, *Staphylococcus aureus*, *Vibrio parahaemolyticus*, and *Bacillus anthraces*, whereas the gold nanocomposite did not show any activity at the same concentrations.

Lastly, as confirmed in FIG. 21, the silver nanocomposite prepared by using the red ginseng root extract prepared in Preparation Example 1-3-3 had an antimicrobial activity against *Vibrio parahaemolyticus*, *Staphylococcus aureus*, *Bacillus cereus*, and *Candida albicans*, and in particular, the silver nanocomposite showed a maximum antimicrobial activity against *Candida albicans*, followed by *Vibrio parahaemolyticus*, *Staphylococcus aureus*, and *Bacillus cereus*. These results are shown in the following Table 2. The above results indicate that the gold or silver nanocomposites of the present invention have antimicrobial activities against microorganisms.

TABLE 2

| Pathogenic microorganism | Zone of inhibition (mm) † |
|---|---|
| Candida albicans [KACC 30062] | 27 ± 0.9 |
| Vibrio parahaemolyticus [ATCC 33844] | 25 ± 0.6 |
| Staphylococcus aureus [ATCC 6538] | 23 ± 1 |
| Bacillus cereus [ATCC 14579] | 16 ± 0.3 |

EXAMPLE 3

Test of Biofilm-Degrading Activity of Nanocomposites

EXAMPLE 3-1

Measurement Method

The biofilm-degrading activity of silver nanocomposites was determined by a colorimetric method against *Staphylococcus aureus* and *Pseudomonas aeruginosa*. Specifically, the wells of 96-well micro-titer plates were filled with 100 μL of overnight-grown log phase of *Staphylococcus aureus* and *Pseudomonas aeruginosa*, followed by incubation for 24 hours. Thereafter, the silver nanocomposites ranging from 1 μg to 4 μg were added. The cell culture plates were then incubated for 4 hours at 37° C. Thereafter, the media were removed and the wells were washed three times with 200 μL of sterile water. Then, the microtiter plate was air-dried for 45 minutes. Then, 200 μL of a 0.1% crystal violet solution in water was added to each well and kept for 4 minutes. The wells were then washed three times with 300 μL of sterile water to remove excess stain. The dye incorporated by the adherent cells was solubilized with 200 μL of 95% ethanol. The absorbance of each well was measured at 595 nm, using a microtiter ELISA reader. The percentage inhibition of biofilm activity was calculated using the following equation: [1−(A595 of test/A595 of control)]×100 (Gurunathan et al., 2014). The experiments were repeatedly performed, and data were interpreted in terms of mean±SD.

EXAMPLE 3-2

Results of Biofilm-Degrading Activity Test

As confirmed in FIG. 22, the silver nanocomposite of Preparation Example 1-3-1, prepared by using the ginseng leaf extract, showed the maximum biofilm-degrading activity against *Staphylococcus aureus* and *Pseudomonas aeruginosa* at a silver nanocomposite concentration of 4 μg/mL. As confirmed in FIG. 23, the silver nanocomposite of Preparation Example 3-3, prepared by using the red ginseng root extract, showed the biofilm-degrading activity against *Staphylococcus aureus* and *Pseudomonas aeruginosa* at a silver nanocomposite concentration of 4 μg/mL.

Accordingly, it was confirmed that the nanocomposites prepared by using the ginseng extracts have biofilm-degrading activities against the strains to inhibit biofilm-related infections, and thus, they play a role in cost reduction or alleviating a patient's pain.

EXAMPLE 4

Test of Anticoagulant Activity of Nanocomposites

EXAMPLE 4-1

Measurement Method

Human blood was collected from each of healthy male and female volunteers (aged between 25 and 45), and put in two evacuated blood collection tubes, which were marked as A and B. After the elapse of time, the anticoagulant effect of the synthesized gold nanocomposites was examined.

EXAMPLE 4-2

Results of Anticoagulant Activity Test

As shown in FIG. 24, the gold nanocomposites of Preparation Example 1-3-1, prepared by using the ginseng leaf extract, were confirmed to inhibit coagulation (FIG. 24A). In contrast, a control group containing no anticoagulant agent showed complete coagulation (FIG. 24B). Further, even after 24 hours, no specific change in the stability of the gold nanocomposites was observed.

These results indicate that the gold nanocomposites biosynthesized by the ginseng leaf extract have anticoagulant activity, and also indicate that the gold nanocomposites may be used after being modified as a drug or gene carrier that is in direct contact with blood, a biosensor, or an in vivo nanocarrier.

EXAMPLE 5

Test of Cytotoxicity of Nanocomposites Against Keratinocytes and Cancer Cells

In order to measure anti-cancer activities of the nanocomposites of Preparation Example 1-3-1, prepared by using the ginseng leaf extract, cytotoxicities of the gold nanocomposite and the silver nanocomposites on the human lung cancer cell (A549) and keratinocyte (HaCaT Skin) were measured by MTT assay. As a result, the silver nanocomposites showed no cytotoxicity on keratinocytes even at a concentration of 1,000 μg/mL, indicating biocompatibility (FIG. 25). However, the silver nanocomposites showed cytotoxicity on A549 lung cancer cells even at a concentration of 100 μg/mL. Further, the gold nanocomposites showed no cytotoxicity on keratinocytes even at a concentration of 20 μg/mL, indicating biocompatibility (FIG. 25). However, the gold nanocomposites showed cytotoxicity on A549 lung cancer cells even at a concentration of 2 μg/mL. Accordingly, it can be seen that the silver nanocomposites have biocompatibility for drug delivery and the gold nanocomposites may be used as an anti-cancer agent.

EXAMPLE 6

Test of Anti-Inflammatory Activity of Nanocomposites

RAW264.7 cells were treated with the silver or gold nanocomposites of Preparation Example 1-3-1, prepared by using the ginseng leaf extract, and then cell viability was measured. RAW264.7 cells were treated with LPS (1 μg/mL) together with the silver or gold nanocomposites, and then NO production was measured. In this regard, L-NMMA (monomethyl arginine) was used as a positive control. As a result, it was confirmed that the silver nanocomposites showed no cytotoxicity on RAW264.7 cells until 1,000 μM, and inhibited NO production in a concentration-dependent manner (FIG. 26). It was also confirmed that the gold nanocomposites showed no cytotoxicity on RAW264.7 cells until 100 μM, and inhibited NO production in a concentration-dependent manner (FIG. 26). Accordingly, it was confirmed that the silver and gold nanocomposites biosynthesized by the ginseng leaf extract have anti-inflammatory activity without cytotoxicity.

PREPARATION EXAMPLE 2

Method of Preparing BSA-CK and BSA-Rh2

To improve solubility of ginsenoside CK or Rh2, BSA-CK or BSA-Rh2 nanocomposite was prepared by conjugating BSA to the ginsenoside.

Specifically, to prepare nanocomposites, the following reagents were used. Bovine serum albumin (BSA, $M_w$=66,000) was purchased from Sigma Aldrich (St. Louis, Mo., USA), ginsenoside CK and Rh2 were purchased from Ginseng Genetic Resource Bank (Kyung Hee University, Yongin, South Korea). All other chemicals were of analytical grade.

Synthesis of BSA-CK was performed by a desolvation method. Specifically, BSA was dissolved in water, and sonicated for 5 minutes to 10 minutes. Thereafter, the BSA-water mixture was vigorously stirred, and ginsenoside CK dissolved in ethanol was added dropwise to the BSA-water mixture. The BSA-ginsenoside reaction mixture was stored at room temperature for 24 hours. Then, the reaction mixture was transferred to a dialysis membrane ($M_w$ cut-off: 3,000), which was subjected to dialysis in methanol/distilled water (75:25, v/v) overnight, and further subjected to dialysis in distilled water for 2 days, followed by freeze-drying.

The BSA-Rh2 nanocomposite was also prepared by using ginsenoside Rh2 in the same manner as above.

EXAMPLE 7

Analysis of BSA-CK and BSA-Rh2 Synthesis

EXAMPLE 7-1

Examination of Amount of Ginsenoside in BSA-CK and BSA-Rh2

The amount of ginsenoside loaded in the BSA-CK or BSA-Rh2 nanocomposite was calculated by HPLC.

As a result, as shown in FIG. 27A, BSA-CK showed a clear peak consistent with that of CK alone, and the amount of CK loaded in BSA-CK was 0.087 mg per 1 mg of nanocomposite. Furthermore, as shown in FIG. 27D, BSA-Rh2 showed a clear peak consistent with that of Rh2 alone, and the amount of Rh2 loaded in BSA-Rh2 was 0.096 mg per 1 mg of nanocomposite.

EXAMPLE 7-2

Examination of Intrinsic Characteristics of Ginsenosides of BSA-CK and BSA-Rh2

In order to examine whether the BSA-CK and BSA-Rh2 nanocomposites of the present invention were prepared well, structures of BSA-CK, BSA-Rh2, and intermediates thereof were examined by $^1$H NMR and FT-IR.

Specifically, $^1$H NMR spectra were recorded at 300 MHz (JEOL, Tokyo, Japan), and samples were dissolved in $D_2O$ or $CD_3OD$. FT-IR spectra were confirmed by a Perkin-Elmer FT-IR spectrophotometer using KBr pellets.

As a result, as shown in FIGS. 27B and 27C, $^1$H NMR and FTIR results of BSA-CK showed a characteristic peak of CK. Further, as shown in FIGS. 27E and 27F, $^1$H NMR and FTIR results of BSA-Rh2 showed a characteristic peak of Rh2.

These results indicate that the BSA-CK and BSA-Rh2 nanocomposites have intrinsic characteristics of CK and Rh2, respectively.

EXAMPLE 8

Physicochemical Characterization of BSA-CK and BSA-Rh2

EXAMPLE 8-1

Morphological Analysis

In order to examine morphologies of the BSA-CK and BSA-Rh2 nanocomposites of the present invention, FE-TEM (JEM-2000F, JEOL) operated at an acceleration voltage of 200 kV was used.

Specifically, in order to prepare FE-TEM samples, one drop of sample solution was placed onto a 200-mesh carbon-coated copper grid and allowed to air dry. The size distributions and stability of the nanocomposites were determined by a particle analyzer and zeta potential, and the samples were dispersed in phosphate-buffered saline (PBS, pH 7.4) or acetate buffer (pH 5.0).

As a result, as shown in FIGS. 28A and 28D, BSA-CK and BSA-Rh2 were confirmed to have a spherical morphology with a uniform size distribution.

EXAMPLE 8-2

Size Distribution Analysis

In order to examine the size distribution of the BSA-CK and BSA-Rh2 nanocomposites of the present invention, dynamic light scattering (DLS) was performed.

As a result, as shown in FIGS. 28B and 28E, BSA-CK and BSA-Rh2 were confirmed to have an average hydrodynamic size of 157.2 nm and 175.8 nm, respectively.

EXAMPLE 8-3

Stability Analysis

The high electrostatic repulsion between the negative charges on the nanocomposite surface prevents agglomeration in a colloidal state, thereby providing high stability. Therefore, in order to examine stability of BSA-CK or BSA-Rh2 nanocomposites of the present invention in a solution, zeta potentials were measured and compared.

As a result, as shown in FIGS. 28C and 28F, it was confirmed that the zeta potentials of BSA-CK and BSA-Rh2 were −70.80 mV and −80.2 mV, respectively. As compared with the zeta potential of BSA itself of −17.9 mV, BSA-CK and BSA-Rh2 have considerably high zeta potentials, indicating that they fall within a stable range.

Accordingly, it was confirmed that the nanocomposites of the present invention were prepared by forming the stable system.

EXAMPLE 9

Solubility Analysis of BSA-CK and BSA-Rh2

High water solubility advantageously enhances pharmacokinetic properties such as bioavailability, membrane permeability, therapeutic activity, etc. Since solubility for water is the most important physiochemical factor for drug absorption, solubilities of the BSA-CK and BSA-Rh2 nanocomposites of the present invention were analyzed.

As a result, as shown in FIGS. 29A and 29B, it was confirmed that the ginsenoside CK or Rh2 alone was insoluble even at a low concentration, whereas BSA-CK and BSA-Rh2 were readily dissolved in water. These results indicate that the nanocomposites of the present invention may be usefully applied as drugs, because of their high solubility.

EXAMPLE 10

Analysis of Anti-Cancer Activities of BSA-CK and BSA-Rh2

In order to analyze anti-cancer activities of the BSA-CK and BSA-Rh2 nanocomposites of the present invention, cytotoxicity on lung cancer cells was examined through the following Examples 10-1 and 10-2.

EXAMPLE 10-1

Examination of Cytotoxicity of BSA-CK

In order to analyze an anti-cancer activity of the BSA-CK nanocomposites, cytotoxicity on lung cancer cells was examined.

First, human lung cancer cells (A549) were cultured in RPMI 1640 medium supplemented with 10% fetal bovine serum (FBS) and 100 IU/mL penicillin and 100 µg/mL streptomycin (Gibco-Brl. Gaithersburg, Md., USA). Cells were incubated at 37° C. in a humidified atmosphere containing 5% $CO_2$.

Thereafter, cell viability was evaluated by MTT (3-(4,5-dimethylthiazol-2-yl)-2,5-diphenyltetrazolium bromide) assay. Specifically, cells were dispensed in a 96-well plate at a density of $1 \times 10^5$ cells/mL, and cultured for 24 hours. Then, the cells were treated with various concentrations of BSA-Rh2, BSA-CK, ginsenoside CK, or Rh2 for 24 hours. After incubation for a predetermined time, 10 µL of MTT stock solution (5 mg/mL) was added to each well, and incubated for 4 hours. Thereafter, the supernatant was removed and 100 µL of DMSO was added to each well. The amount of formazan formed by living cells was measured at 570 nm using a multi-model plate reader, and a reference wavelength was 630 nm. Additionally, cytotoxicity on a keratinocyte cell line was measured in the same manner as above.

As a result, as shown in FIGS. 30A and 30B, 5 µg/mL of the BSA-CK nanocomposite showed about 80% cell growth inhibition against an A549 lung cancer cell line, indicating considerably high cytotoxicity. The BSA-CK nanocomposite showed remarkably excellent cytotoxicity, as compared with CK alone. In contrast, it was confirmed that the BSA-CK nanocomposite showed no cytotoxicity on a keratinocyte cell line even at a high concentration of 10 µg/mL.

These results indicate that BSA-CK has excellent anti-cancer activity because it shows cytotoxicity on A549, and BSA-CK shows cancer cell-specific cytotoxicity because it does not act on normal cells.

EXAMPLE 10-2

Examination of Cytotoxicity of BSA-Rh2

In order to analyze an anti-cancer activity of the BSA-Rh2 nanocomposites, cytotoxicity on lung cancer cells was examined.

Specifically, culturing of A549 lung cancer cell line and cell viability test were performed according to the method of Example 4-1.

As a result, as shown in FIGS. 30C and 30D, it was confirmed that the BSA-Rh2 nanocomposite showed slightly low cytotoxicity on an A549 lung cancer cell line, as compared with Rh2 alone. It was also confirmed that BSA-Rh2 showed no cytotoxicity on a keratinocyte cell line up to a concentration of 15 μM, but Rh2 alone showed cytotoxicity at the same concentration.

These results indicate that BSA-Rh2 shows cancer cell-specific cytotoxicity.

EXAMPLE 11

Analysis of Anti-Inflammatory Activities of BSA-CK and BSA-Rh2

In order to analyze anti-inflammatory activities of the BSA-CK and BSA-Rh2 nanocomposites of the present invention, cytotoxicity on macrophage cells was examined through the following Examples 5-1 and 5-2, and inhibitory activity on NO production of LPS-induced macrophage cells was examined through the following Examples 5-3 and 5-4.

EXAMPLE 11-1

Analysis of Anti-Inflammatory Activity of BSA-CK

EXAMPLE 11-1-1

Examination of Cytotoxicity of BSA-CK

In order to analyze anti-inflammatory activity of the BSA-CK nanocomposite, cytotoxicity on macrophage cells was examined.

First, a murine macrophage cell line (RAW 264.7) was dispensed in a 96-well microplate at a density of $5 \times 10^3$ cells/well. In this regard, RPMI 1640 medium supplemented with 10% fetal bovine serum (FBS), 100 IU/mL penicillin, and 100 μg/mL streptomycin (Gibco-Brl. Gaithersburg, Md., USA) was used and incubated at 37° C. for 24 hours in a humidified atmosphere containing 5% $CO_2$. Thereafter, cell viability was evaluated by the MTT assay according to Example 4-1.

As a result, as shown in FIG. 31A, it was confirmed that the BSA-CK nanocomposite did not inhibit macrophage growth at a concentration of 5 μg/mL, but inhibited growth at a high concentration of 10 μg/mL.

EXAMPLE 11-1-2

Examination of NO Production Inhibitory Activity of BSA-CK

In order to analyze anti-inflammatory activity of the BSA-CK nanocomposite, inhibitory activity on NO production of macrophage cells was examined.

Specifically, to measure the amount of produced nitric oxide (NO), RAW 264.7 cells were pre-treated with BSA-Rh2, BSA-CK, ginsenoside CK alone, or Rh2 alone for 1 hour, and then stimulated with 1 μg/μL of lipopolysaccharide (LPS) in the presence of the samples. Cells were incubated for 24 hours, and 100 μL of the cell culture supernatant was mixed with an equal volume of the Griess reagent. The resultant absorbance at 540 nm was measured using a microplate reader (BioTek Instruments, Inc.). A standard sodium nitrite curve was included for each experiment.

As a result, as shown in FIG. 31B, it was confirmed that BSA-CK nanocomposite significantly inhibited NO production of macrophage at a low concentration of 1 μg/mL showing no cytotoxicity. It was also confirmed that BSA-CK nanocomposite showed slight but more excellent inhibition of NO production of macrophage, as compared with CK alone. This effect was confirmed to improve with increasing concentration of the BSA-CK nanocomposite.

These results indicate that BSA-CK shows excellent anti-inflammatory activity, because it selectively inhibits NO production without direct cytotoxicity against a normal macrophage cell line.

EXAMPLE 11-2

Analysis of Anti-Inflammatory Activity of BSA-Rh2

EXAMPLE 11-2-1

Examination of Cytotoxicity of BSA-Rh2

In order to analyze anti-inflammatory activity of the BSA-Rh2 nanocomposite, cytotoxicity on macrophage cells was examined.

Specifically, culturing of RAW 264.7 and a cell viability test were performed according to the method of Example 5-1-1.

As a result, as shown in FIG. 31C, it was confirmed that the BSA-Rh2 nanocomposite did not inhibit macrophage growth at a concentration of 5 μg/mL, but inhibited growth at a high concentration of 10 μg/mL.

EXAMPLE 11-2-2

Examination of NO Production Inhibitory Activity of BSA-Rh2

In order to analyze anti-inflammatory activity of the BSA-Rh2 nanocomposite, inhibitory activity on NO production of macrophage cells was examined.

Specifically, NO production of RAW 264.7 by treatment of BSA-Rh2 was examined according to the method of Example 5-1-2.

As a result, as shown in FIG. 31D, it was confirmed that the BSA-Rh2 nanocomposite significantly inhibited NO production of macrophage at a low concentration of 1 μg/mL showing no cytotoxicity. It was also confirmed that the BSA-Rh2 nanocomposite showed slight but more excellent inhibition of NO production of macrophage, as compared with Rh2 alone. This effect was confirmed to improve with increasing concentration of the BSA-Rh2 nanocomposite.

These results indicate that BSA-Rh2 shows excellent anti-inflammatory activity, because it selectively inhibits NO production without direct cytotoxicity against a normal macrophage cell line.

PREPARATION EXAMPLE 3

Method of Synthesizing MSNP-CK and MSNP-Rh2

To improve targeting ability and half-life of ginsenoside CK or Rh2, MSNP-CK or MSNP-Rh2 nanocomposite was prepared by conjugating mesoporous silica nanoparticles (MSNPs) to the ginsenosides.

Specifically, to prepare nanocomposites, the following reagents were used. The mesoporous silica nanoparticles (MSNP, 200 nm, 4 nm in pore size) were purchased from Sigma Aldrich (St. Louis, Mo., USA). Tetraethyl orthosilicate (TEOS, 98%) as a silica source, 3-aminopropyltriethoxy-silane (APTEOS, 98%) as a coupling agent, and fluorescein isothiocyanate (FITC) as a dye, were purchased from Sigma-Aldrich Chemical (USA). Ginsenosides CK and Rh2 were purchased from Ginseng Genetic Resource Bank (Kyung Hee University, Yongin, South Korea). All other chemicals were of analytical grade.

Synthesis of MSNP-CK was performed by the following three steps. In a first step, 250 mg of FITC and 10 mL of absolute ethanol were added to a long three-neck bottle of 50 mL volume. Thereafter, 2.5 mL of water and $NH_4OH$ were added and stirred at room temperature for 30 minutes. 15 mL of TEOS and 200 µL of APTMS were added to the mixed solution, and stirred for 12 hours under dark conditions to prevent bleaching of the dye. The obtained FITC/APTMS composite was stored under dark conditions to avoid photobleaching. The prepared nanocomposite solution was distilled to remove the ethanol solvent before use.

In a second step, for efficient binding of the ginsenoside, MSNP was functionalized with free amine groups and silica was coated with FITC. Specifically, 100 mg of MSNP was dissolved in 15 mL of toluene, and this mixture was dispersed well, followed by stirring. 10 µL of APTMS was then added thereto dropwise and one drop of HCl (1 M) was added. This reaction mixture was stirred for 24 hours and washed with water several times, followed by drying.

In a last third step, to conjugate MSNP to ginsenoside, activated MSNP (100 mg) was added to 5 mL of water, and ginsenoside CK (30 mg) dissolved in 10 mL of ethanol was added thereto dropwise. 20 mg of FITC dye-coated silica was further added, and then stirred for 48 hours. The obtained nanoparticles were centrifuged at 10,000 rpm for 20 minutes, and then washed with absolute ethanol three times, and washed with water three times in order to remove unreacted chemicals, followed by drying. In order to obtain MSNP-CK and MSNP-Rh2, a dialyzed solution was freeze-dried.

The MSNP-Rh2 nanocomposite was also synthesized using ginsenoside Rh2 in the same manner as above.

EXAMPLE 12

Analysis of MSNP-CK and MSNP-Rh2 Synthesis

EXAMPLE 12-1

Examination of Amount of Ginsenoside in MSNP-CK and MSNP-Rh2

The amount of ginsenoside loaded in the MSNP-CK or MSNP-Rh2 nanocomposite was calculated by HPLC.

As a result, as shown in FIG. 32A, MSNP-CK showed a clear peak consistent with that of CK alone, and the amount of CK loaded in MSNP-CK was 0.066 mg per 1 mg of nanocomposite. Furthermore, as shown in FIG. 32D, MSNP-Rh2 showed a clear peak consistent with that of Rh2 alone, and the amount of Rh2 loaded in MSNP-Rh2 was 0.072 mg per 1 mg of nanocomposite.

EXAMPLE 12-2

Examination of Intrinsic Characteristics of Ginsenosides of MSNP-CK and MSNP-Rh2

In order to examine whether the MSNP-CK and MSNP-Rh2 nanocomposites of the present invention were prepared well, structures of MSNP-CK, MSNP-Rh2, and intermediates thereof were examined by $^1$H NMR and FT-IR.

Specifically, $^1$H NMR spectra were recorded at 300 MHz (JEOL, Tokyo, Japan), and samples were dissolved in $D_2O$ or $CD_3OD$. FT-IR spectra were confirmed by a Perkin-Elmer FT-IR spectrophotometer using KBr pellets.

As a result, as shown in FIGS. 32B and 32C, $^1$H NMR and FTIR results of MSNP-CK showed a characteristic peak of CK. Further, as shown in FIGS. 32E and 32F, $^1$H NMR and FTIR results of MSNP-Rh2 showed a characteristic peak of Rh2.

These results indicate that the MSNP-CK and MSNP-Rh2 nanocomposites have intrinsic characteristics of CK and Rh2, respectively.

EXAMPLE 13

Morphological Analysis of MSNP-CK and MSNP-Rh2

In order to examine morphologies of the MSNP-CK and MSNP-Rh2 nanocomposites of the present invention, FE-TEM (JEM-2000F, JEOL) operated at an acceleration voltage of 200 kV was used.

Specifically, in order to prepare FE-TEM samples, one drop of sample solution was placed onto a 200-mesh carbon-coated copper grid and allowed to air dry. The samples were dispersed in phosphate-buffered saline (PBS, pH 7.4) or acetate buffer (pH 5.0).

As a result, as shown in FIGS. 33A and 33B, MSNP-CK and MSNP-Rh2 were confirmed to have a spherical morphology with a uniform size distribution.

EXAMPLE 14

Analysis of Anti-Cancer Activities of MSNP-CK and MSNP-Rh2

In order to analyze anti-cancer activities of the MSNP-CK and MSNP-Rh2 nanocomposites of the present invention, cytotoxicity on lung cancer cells was examined through the following Examples 3-1 and 3-2.

EXAMPLE 14-1

Examination of Cytotoxicity of MSNP-CK

In order to analyze an anti-cancer activity of the MSNP-CK nanocomposites, cytotoxicity on lung cancer cells was examined.

First, human lung cancer cells (A549) were cultured in RPMI 1640 medium supplemented with 10% fetal bovine serum (FBS) and 100 IU/mL penicillin and 100 µg/mL streptomycin (Gibco-Brl. Gaithersburg, Md., USA). Cells were incubated at 37° C. in a humidified atmosphere containing 5% $CO_2$.

Thereafter, cell viability was evaluated by MTT (3-(4,5-dimethylthiazol-2-yl)-2,5-diphenyltetrazolium bromide) assay. Specifically, cells were dispensed in a 96-well plate at a density of $1 \times 10^5$ cells/mL, and cultured for 24 hours. Then, the cells were treated with various concentrations of MSNP-Rh2, MSNP-CK, ginsenoside CK, or Rh2 for 24 hours. After incubation for a predetermined time, 10 µL of MTT stock solution (5 mg/mL1) was added to each well, and incubated for 4 hours. Thereafter, the supernatant was removed and 100 µL of DMSO was added to each well. The amount of formazan formed by living cells was measured at 570 nm using a multi-model plate reader, and a reference wavelength was 630 nm. Additionally, cytotoxicity on a keratinocyte cell line was measured in the same manner as above.

As a result, as shown in FIGS. 34A and 34B, the MSNP-CK nanocomposite showed about 50% cell growth inhibition against an A549 lung cancer cell line at a low concentration of 1 µg/mL, indicating considerably high cytotoxicity, and showed about 90% or more cytotoxicity at a concentration of 10 µg/mL. The MSNP-CK nanocomposite showed remarkably excellent cytotoxicity, as compared with CK alone. In contrast, it was confirmed that the MSNP-CK nanocomposite showed no cytotoxicity on a keratinocyte cell line even at a high concentration of 15 µg/mL.

These results indicate that MSNP-CK has excellent anti-cancer activity because it shows cytotoxicity on A549, and MSNP-CK shows cancer cell-specific cytotoxicity because it does not act on normal cells.

EXAMPLE 3-2

Examination of Cytotoxicity of MSNP-Rh2

In order to analyze an anti-cancer activity of the MSNP-Rh2 nanocomposites, cytotoxicity on lung cancer cells was examined.

Specifically, culturing of an A549 lung cancer cell line and a cell viability test were performed according to the method of Example 3-1.

As a result, as shown in FIGS. 35C and 35D, the MSNP-Rh2 nanocomposite showed about 50% cell growth inhibition against an A549 lung cancer cell line at a low concentration of 1 µg/mL, indicating considerably high cytotoxicity, and showed about 90% or more cytotoxicity at a concentration of 15 µg/mL. The MSNP-Rh2 nanocomposite showed remarkably excellent cytotoxicity, as compared with Rh2 alone. In contrast, it was confirmed that the MSNP-Rh2 nanocomposite showed no cytotoxicity on a keratinocyte cell line even at a high concentration of 15 µg/mL.

These results indicate that MSNP-Rh2 has excellent anti-cancer activity because it shows cytotoxicity on A549, and MSNP-Rh2 shows cancer cell-specific cytotoxicity because it does not act on normal cells.

EXAMPLE 15

Analysis of Anti-Inflammatory Activities of MSNP-CK and MSNP-Rh2

In order to analyze anti-inflammatory activities of the MSNP-CK and MSNP-Rh2 nanocomposites of the present invention, cytotoxicity on macrophage cells was examined through the following Examples 15-1-1 and 15-2-1, and inhibitory activity on NO production of LPS-induced macrophage cells was examined through the following Examples 15-1-2 and 15-2-2.

EXAMPLE 15-1

Analysis of Anti-Inflammatory Activity of MSNP-CK

EXAMPLE 15-1-1

Examination of Cytotoxicity of MSNP-CK

In order to analyze anti-inflammatory activity of the MSNP-CK nanocomposite, cytotoxicity on macrophage cells was examined.

First, a murine macrophage cell line (RAW 264.7) was dispensed in a 96-well microplate at a density of $5 \times 10^3$ cells/well. In this regard, RPMI 1640 medium supplemented with 10% fetal bovine serum (FBS), 100 IU/mL penicillin, and 100 µg/mL streptomycin (Gibco-Brl. Gaithersburg, Md., USA) was used and incubated at 37° C. for 24 hours in a humidified atmosphere containing 5% $CO_2$. Thereafter, cell viability was evaluated by the MTT assay according to Example 3-1.

As a result, as shown in FIG. 35A, it was confirmed that the MSNP-CK nanocomposite did not inhibit macrophage growth at a concentration of 5 µg/mL, but inhibited growth at a high concentration of 10 µg/mL.

EXAMPLE 15-1-2

Examination of NO Production Inhibitory Activity of MSNP-CK

In order to analyze anti-inflammatory activity of the MSNP-CK nanocomposite, inhibitory activity on NO production of macrophage cells was examined.

Specifically, to measure the amount of produced nitric oxide (NO), RAW 264.7 cells were pre-treated with MSNP-Rh2, MSNP-CK, ginsenoside CK alone, or Rh2 alone for 1 hour, and then stimulated with 1 µg/µL of lipopolysaccharide (LPS) in the presence of the samples. Cells were incubated for 24 hours, and 100 µL of the cell culture supernatant was mixed with an equal volume of the Griess reagent. The resultant absorbance at 540 nm was measured using a microplate reader (BioTek Instruments, Inc.). A standard sodium nitrite curve was included for each experiment.

As a result, as shown in FIG. 35B, it was confirmed that the MSNP-CK nanocomposite significantly inhibited NO production of macrophage at a low concentration of 1 µg/mL showing no cytotoxicity. It was also confirmed that the MSNP-CK nanocomposite showed slight but more excellent inhibition of NO production of macrophage, as compared with CK alone. This effect was confirmed to improve with increasing concentration of the MSNP-CK nanocomposite.

These results indicate that MSNP-CK shows excellent anti-inflammatory activity, because it selectively inhibits NO production without direct cytotoxicity against a normal macrophage cell line.

EXAMPLE 15-2

Analysis of Anti-Inflammatory Activity of MSNP-Rh2

EXAMPLE 15-2-1

Examination of Cytotoxicity of MSNP-Rh2

In order to analyze anti-inflammatory activity of the MSNP-Rh2 nanocomposite, cytotoxicity on macrophage cells was examined.

Specifically, culturing of RAW 264.7 and a cell viability test were performed according to the method of Example 4-1-1.

As a result, as shown in FIG. 35C, it was confirmed that the MSNP-Rh2 nanocomposite did not inhibit macrophage growth at a concentration of 5 µg/mL, but inhibited growth at a high concentration of 10 µg/mL.

EXAMPLE 15-2-2

Examination of NO Production Inhibitory Activity of MSNP-Rh2

In order to analyze anti-inflammatory activity of the MSNP-Rh2 nanocomposite, inhibitory activity on NO production of macrophage cells was examined.

Specifically, NO production of RAW 264.7 by treatment of MSNP-Rh2 was examined according to the method of Example 4-1-2.

As a result, as shown in FIG. 35D, it was confirmed that the MSNP-Rh2 nanocomposite significantly inhibited NO production of macrophage at a low concentration of 1 µg/mL showing no cytotoxicity. It was also confirmed that the MSNP-Rh2 nanocomposite showed slight but more excellent inhibition of NO production of macrophage, as compared with Rh2 alone. This effect was confirmed to improve with increasing concentration of the MSNP-Rh2 nanocomposite.

These results indicate that MSNP-Rh2 shows excellent anti-inflammatory activity, because it selectively inhibits NO production without direct cytotoxicity against a normal macrophage cell line.

Based on the above description, it will be understood by those skilled in the art that the present disclosure may be implemented in a different specific form without changing the technical spirit or essential characteristics thereof. Therefore, it should be understood that the above embodiment is not limitative, but illustrative in all aspects. The scope of the present disclosure is defined by the appended claims rather than by the description preceding them, and therefore all changes and modifications that fall within metes and bounds of the claims, or equivalents of such metes and bounds are therefore intended to be embraced by the claims.

Effect of the Invention

A metal nanocomposite of the present invention may be prepared in a uniform size without using an additional reducing agent or stabilizing agent in a significantly shortened time, as compared with known metal nanoparticles. Further, since the metal nanocomposite has high solubility in water and high targeting ability for cancer cells, it can be advantageously developed as drugs. Further, the metal nanocomposite exhibits high anti-cancer and anti-inflammatory activities, and thus may be usefully applied to prevention or treatment of cancer and inflammatory diseases. Furthermore, the metal nanocomposite exhibits anti-microbial activity, biofilm-degrading activity, and anti-coagulant activity, and thus may be applied to a variety of industrial fields.

What is claimed is:

1. A method of treating lung cancer, the method comprising the step of administering to a patient in need thereof a therapeutically effective amount of a composition comprising a nanocomposite, wherein the nanocomposite comprises nanoparticles that comprise (i) a metal and (ii) a ginseng extract or a ginsenoside isolated therefrom.

* * * * *